US012616771B2

(12) United States Patent
McCarthy et al.

(10) Patent No.: US 12,616,771 B2
(45) Date of Patent: May 5, 2026

(54) TISSUE ADHERENT CHITOSAN MATERIAL THAT RESISTS DISSOLUTION

(71) Applicant: TRICOL BIOMEDICAL, INC., Portland, OR (US)

(72) Inventors: Simon J. McCarthy, Portland, OR (US); Cole Gannett, Portland, OR (US); Mattie R. Jones, Portland, OR (US); Ervelyn Winata, Portland, OR (US)

(73) Assignee: TRICOL BIOMEDICAL, INC., Portland, OR (US)

( * ) Notice: Subject to any disclaimer, the term of this patent is extended or adjusted under 35 U.S.C. 154(b) by 165 days.

(21) Appl. No.: 16/958,311

(22) PCT Filed: Dec. 28, 2018

(86) PCT No.: PCT/US2018/068064
§ 371 (c)(1),
(2) Date: Jun. 26, 2020

(87) PCT Pub. No.: WO2019/133936
PCT Pub. Date: Jul. 4, 2019

(65) Prior Publication Data
US 2021/0060203 A1      Mar. 4, 2021

Related U.S. Application Data

(60) Provisional application No. 62/631,290, filed on Feb. 15, 2018, provisional application No. 62/612,013, filed on Dec. 29, 2017.

(51) Int. Cl.
*A61L 15/28* (2006.01)
*A61F 13/01* (2024.01)
*A61L 15/42* (2006.01)

(52) U.S. Cl.
CPC ........ *A61L 15/28* (2013.01); *A61F 13/01012* (2024.01); *A61L 15/425* (2013.01)

(58) Field of Classification Search
CPC ... A61L 15/28; A61L 15/425; A61F 13/00012
See application file for complete search history.

(56) References Cited

U.S. PATENT DOCUMENTS

| | | | |
|---|---|---|---|
| 7,371,403 B2 | 5/2008 | McCarthy et al. | |
| 7,482,503 B2 | 1/2009 | Gregory et al. | |
| 7,820,872 B2 | 10/2010 | Gregory et al. | |
| 7,897,832 B2 | 3/2011 | McAdams et al. | |
| 8,269,058 B2 | 9/2012 | McCarthy et al. | |
| 8,313,474 B2 | 11/2012 | Campbell et al. | |
| 8,741,335 B2 | 6/2014 | McCarthy | |
| 8,858,883 B2 | 10/2014 | Dowling et al. | |
| 8,920,514 B2 | 12/2014 | Gregory et al. | |
| 9,004,918 B2 | 4/2015 | McAdams et al. | |
| 9,204,957 B2 | 12/2015 | Gregory et al. | |
| 9,205,170 B2 | 12/2015 | Lucchesi et al. | |
| 10,086,105 B2 | 10/2018 | Guo et al. | |
| 10,315,023 B2 | 6/2019 | Mantri et al. | |
| 11,564,673 B2 | 1/2023 | Perry et al. | |
| 11,660,236 B2 | 5/2023 | McCarthy et al. | |
| 2004/0243043 A1 | 12/2004 | McCarthy et al. | |
| 2005/0038369 A1 | 2/2005 | Gregory et al. | |
| 2005/0137512 A1 | 6/2005 | Campbell et al. | |
| 2006/0089584 A1 | 4/2006 | McAdams et al. | |
| 2007/0166387 A1 | 7/2007 | Ahuja et al. | |
| 2008/0114286 A1 | 5/2008 | Hamel et al. | |
| 2008/0287907 A1 | 11/2008 | Gregory et al. | |
| 2009/0214712 A1 | 8/2009 | Kang et al. | |
| 2009/0226391 A1* | 9/2009 | Roberts ................. A61L 15/425 424/78.06 |
| 2012/0065674 A1 | 3/2012 | Levy | |
| 2012/0296313 A1 | 11/2012 | Andreacchi et al. | |
| 2014/0193360 A1 | 7/2014 | Lee et al. | |
| 2015/0361218 A1 | 12/2015 | Lee et al. | |
| 2016/0030625 A1 | 2/2016 | Mrozek et al. | |
| 2018/0085500 A1 | 3/2018 | Lee et al. | |
| 2020/0306248 A1 | 10/2020 | Beeley et al. | |
| 2021/0052261 A1 | 2/2021 | Perry et al. | |
| 2021/0052766 A1 | 2/2021 | Gannett et al. | |

(Continued)

FOREIGN PATENT DOCUMENTS

| CA | 2669780 A1 | 5/2008 |
|---|---|---|
| CN | 101018554 A | 8/2007 |

(Continued)

OTHER PUBLICATIONS

Adler et al., "ASGE guideline: the role of endoscopy in acute non-variceal upper-GI hemorrhage," *Gastrointestinal Endoscopy* 60(4):497-504, 2004.
Banerjee et al., "The role of endoscopy in the management of patients with peptic ulcer disease," *Gastrointestinal Endoscopy* 71(4):663-668, 2010.
Boonpongmanee et al., "The frequency of peptic ulcer as a cause of upper-GI bleeding is exaggerated," *Gastrointestinal Endoscopy* 59(7):788-794, 2004.
Crooks et al., "Upper gastrointestinal haemorrhage and deprivation: a nationwide cohort study of health inequality in hospital admissions," *Gut* 61(4):514-520, 2012.
Elta et al., "Chapter 8: Approach to the patient with gross gastrointestinal bleeding," *Principles of Clinical Gastroenterology*: 122-151, 2008.

(Continued)

*Primary Examiner* — Robert A Wax
*Assistant Examiner* — Olga V. Tcherkasskaya
(74) *Attorney, Agent, or Firm* — Seed IP Law Group LLP

(57) ABSTRACT

The present invention relates to a biocompatible, foldable, thin profile, low mass and high surface area, chitosan dressing, optionally modified with catechol, and suitable for treating bleeding in a physiological environment, e.g., gastrointestinal tract, bladder (in particular in connection with the TURP procedure). The characteristics and structures of the chitosan dressing are provided. Methods of making and using the chitosan dressing are also provided.

17 Claims, 48 Drawing Sheets

(56) References Cited

U.S. PATENT DOCUMENTS

| | | | |
|---|---|---|---|
| 2021/0059867 A1 | 3/2021 | Mccarthy et al. |
| 2021/0059868 A1 | 3/2021 | Gannett et al. |
| 2021/0060203 A1 | 3/2021 | Mccarthy et al. |
| 2023/0355224 A1 | 11/2023 | Perry et al. |
| 2024/0009040 A1 | 1/2024 | McCarthy et al. |

FOREIGN PATENT DOCUMENTS

| | | | | |
|---|---|---|---|---|
| CN | 101289477 A | 10/2008 | | |
| CN | 103189435 A | 7/2013 | | |
| CN | 104013990 A | 9/2014 | | |
| CN | 104619165 A | 5/2015 | | |
| CN | 106334209 A | 1/2017 | | |
| CN | 107118357 A | 9/2017 | | |
| CN | 107375196 A | 11/2017 | | |
| CN | 111632026 A | 9/2020 | | |
| CN | 113209363 A | 8/2021 | | |
| CN | 115895440 A | 4/2023 | | |
| CN | 116540072 A | 8/2023 | | |
| EP | 2700419 A1 | 2/2014 | | |
| EP | 2778179 A2 * | 9/2014 | ............ | A61L 27/20 |
| EP | 3300669 A1 | 4/2018 | | |
| GB | 2 514 592 A | 12/2014 | | |
| JP | 2005503197 A | 2/2005 | | |
| JP | 2007516051 A | 6/2007 | | |
| JP | 2008525112 A | 7/2008 | | |
| JP | 2009502749 A | 1/2009 | | |
| JP | 2009513239 A | 4/2009 | | |
| JP | 2016138166 A | 8/2016 | | |
| JP | 2023516335 A | 4/2023 | | |
| KR | 20220161796 A | 12/2022 | | |
| WO | WO 9736630 A1 | 10/1997 | | |
| WO | WO 02102276 A2 | 12/2002 | | |
| WO | WO 2005062896 A2 | 7/2005 | | |
| WO | WO 2006071649 A2 | 7/2006 | | |
| WO | WO 2007009050 A2 | 1/2007 | | |
| WO | WO 2007139845 A2 | 12/2007 | | |
| WO | WO 2009111282 A2 | 9/2009 | | |
| WO | WO 2013180458 A1 | 12/2013 | | |
| WO | WO 2015175662 A1 | 11/2015 | | |
| WO | WO 2016112342 A1 | 7/2016 | | |
| WO | WO 2016159734 A1 | 10/2016 | | |
| WO | WO 2017161331 A1 | 9/2017 | | |
| WO | WO 2017214201 A1 | 12/2017 | | |
| WO | WO 2018204782 A1 | 11/2018 | | |

OTHER PUBLICATIONS

Halkerston et al., "PWE-046 Early Clinical Experience of Endoclot™ in the Treatment of Acute Gastro-Intestinal Bleeding," *Gut* 62(Suppl 1):A149, 2013.

HCUP, "Diagnoses—Clinical Classification Software (CCS), Principal Diagnosis: # 153 Gastrointestinal hemorrhage," U.S. Department of Health and Human Services, 2014. (1 page).

Holster et al., "Hemospray in the treatment of upper gastrointestinal hemorrhage in patients on antithrombotic therapy," *Endoscopy* 45:63-66, 2013.

Jairath et al., "Mortality from Acute Upper Gastrointestinal Bleeding in the United Kingdom: Does It Display a "Weekend Effect"?," *Am J Gastroenterol* 106:1621-1628, 2011.

Jairath et al., "Prevalence, management, and outcomes of patients with coagulopathy after acute nonvariceal upper gastrointestinal bleeding in the United Kingdom," *Transfusion* 53:1069-1076, 2013.

Jairath et al., "Why do mortality rates for nonvariceal upper gastrointestinal bleeding differ around the world? A systematic review of cohort studies," *Can J Gastroenterol* 26(8):537-543, 2012.

Karaman et al., "Endoscopic Topical Application of Ankaferd Blood Stopper® in Gastrointestinal Bleeding," *The Journal of Alternative and Complementary Medicine* 18(1):65-68, 2012.

Kheirabadi et al., "Safety Evaluation of New Hemostatic Agents, Smectite Granules, and Kaolin-Coated Gauze in a Vascular Injury Wound Model in Swine," *The Journal of Trauma Injury, Infection and Critical Care* 68(2):269-278, 2010.

Peng et al., "Factors Associated With Failure of Initial Endoscopic Hemoclip Hemostasis for Upper Gastrointestinal Bleeding," *J Clin Gastroenterol* 40(1):25-28, 2006.

Peng et al., "Factors Contributing to the Failure of Argon Plasma Coagulation Hemostasis in Patients with Nonvariceal Upper Gastrointestinal Tract Bleeding," *Hepato-Gastroenterology* 57:781-786, 2010.

Rockey, "Gastrointestinal bleeding," *Gastroenterol Clin North Am* 34:581-588, 2005.

Ryu et al., "Catechol-Functionalized Chitosan/Pluronic Hydrogels for Tissue Adhesives and Hemostatic Materials", *Biomacromolecules* 12:2653-2659, 2011.

Saraf et al., "Mechanical properties of soft human tissues under dynamic loading," *Journal of Biomechanics* 40:1960-1967, 2007.

Sheibani et al., "Natural history of acute upper GI bleeding due to tumours: short-term success and long-term recurrence with or without endoscopic therapy," *Aliment Pharmacol Ther* 38:144-150, 2013.

Sung et al., "Causes of Mortality in Patients With Peptic Ulcer Bleeding: A Prospective Cohort Study of 10,428 Cases," *Am J Gastroenterol* 105:84-89, 2010.

Sung et al., "Early clinical experience of the safety and effectiveness of Hemospray in achieving hemostasis in patients with acute peptic ulcer bleeding," *Endoscopy* 43:291-295, 2011.

Yau et al., "Safety and efficacy of Hemospray® in upper gastrointestinal bleeding," *Can J Gastroenterol Hepatol* 28(2):72-76, 2014.

Ryu et al., "Bio-inspired adhesive catechol-conjugated chitosan for biomedical application: A mini review," *Acta Biomaterial* 27:101-115, 2015.

AUA Practice Guidelines Committee, "AUA Guideline on Management of Benign Prostatic Hyperplasia (2003). Chapter 1: Diagnosis and Treatment Recommendations," *The Journal of Urology* 170:530-547, Aug. 2003.

Fitzpatrick JM, M.W., Minimally invasive and endoscopic management of benign prostatic hyperplasia. Campbell's Urology, 2002. 8th edition (Walsh PC editor)(Saunders): p. 1379-1422.

HCUP, NIS 2003 Means on Continuous Fields in Core File. HCUP Summary Statistics Report, 2003: p. 27-8.

Kavanagh et al., "Prevention and management of TURP-related hemorrhage," *Nature Reviews Urology* 8:504-514, Sep. 2011.

Kim et al., "Chitosan-catechol: A polymer with long-lasting mucoadhesive properties," *Biomaterials* 52:161-170, Feb. 2015.

McVary et al., "Update on AUA Guideline on the Management of Benign Prostatic Hyperplasia," *The Journal of Urology* 185:1793-1803, May 2011.

Ryu et al., "Bio-Inspired, Water-Soluble to Insoluble Self-Conversion for Flexible, Biocompatible, Transparent, Catecholamine Polysaccharide Thin Films," *Adv. Funt. Mater.* 24:7709-7716, 2014.

Xu et al., "Mollusk Glue Inspired Mucoadhesives for Biomedical Applications," *Langmuir* 28:14010-14017, 2012.

Zeng et al., "Rapid in situ cross-linking of hydrogel adhesives based on thiol-grafted bio-inspired catechol-conjugated chitosan," *Biomaterials Processing* 32(5):612-621, 2017.

Elixhauser et al., "Hospital Inpatient Statistics, 1996," HCUP-3 Research Note, Rockville, MD, Agency for Health Care Policy and Research (AHCPR) Pub. No. 99-0034, current as of Sep. 1999 (9 pages).

George A.F. Roberts, Chapter 5, "Chemical Behaviour of Chitin and Chitosan," *Chitin Chemistry*, 1992, The Macmillan Press Ltd, pp. 203-207 and 278-281. (10 pages).

Healthcare Cost and Utilization Project (HCUP), "National Statistics Trend Information Transurethral Prostatectomy and Open Prostatectomy," US Department of Health and Human Services, 2015. (Entire Document, 1 page).

Subramanian et al., "Mucus interaction to improve gastrointestinal retention and pharmacokinetics of orally administered nano-drug delivery systems," *Journal of Nanobiotechnology* 20:362, Aug. 6, 2022. (23 pages).

* cited by examiner

Chitosan dressing seals the fossa after tissue removal by resection

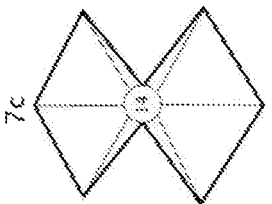
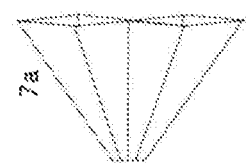
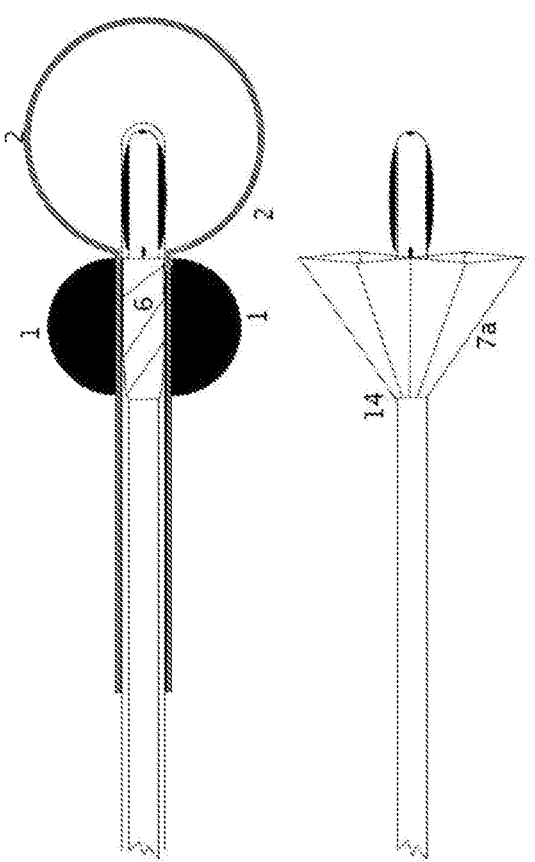
*FIG. 5B*

| Batch # | Catechol CS ID# | CS Used | Starting % CS in soln. | mmol free amine | mmol HCA | mmol EDC HCl | mmol other |
|---|---|---|---|---|---|---|---|
| 1 | N/A | 65010 | ~0.5 | N/A | N/A | N/A | N/A |
| 2 | N/A | 43000 | 0.37 | N/A | N/A | N/A | N/A |
| 3 | N/A | 43000 | 0.48 | N/A | N/A | N/A | N/A |
| 4 | N/A | 65010 | ~0.5 | N/A | N/A | N/A | N/A |
| 5 | N/A | 65010 | ~0.5 | N/A | N/A | N/A | N/A |
| 6 | N/A | 43000 | 0.42 | N/A | N/A | N/A | N/A |
| 7 | N/A | 43000 | ~0.5 | N/A | N/A | N/A | N/A |
| 8 | N/A | 43000 | ~0.5 | N/A | N/A | N/A | N/A |
| 9 | N/A | 43000 | 0.29 | N/A | N/A | N/A | N/A |
| 10 | N/A | 43000 | 0.72 | N/A | N/A | N/A | N/A |
| 11 | N/A | 43000 | 0.51 | N/A | N/A | N/A | N/A |
| 12 | N/A | 43000 | ~0.5 | N/A | N/A | N/A | N/A |
| 13 | N/A | 43000 | 0.69 | N/A | N/A | N/A | NA |
| 14 | N/A | 65010 | 0.46 | N/A | N/A | N/A | NA |
| 15 | N/A | 43000 | 0.42 | N/A | N/A | N/A | N/A |
| 16 | N/A | 43000 | 1.8 | N/A | N/A | N/A | N/A |
| 17 | N/A | 43000 | ~0.5 | N/A | N/A | N/A | N/A |
| 18 | N/A | 43000 | ~0.5 | N/A | N/A | N/A | N/A |
| 19 | N/A | 43000 | ~0.5 | N/A | N/A | N/A | N/A |
| 20 | N/A | 43000 | ~0.5 | N/A | N/A | N/A | N/A |
| 21 | 21 | 43000 | 1.8 | 52.6 | 15.7 | 31.3 | N/A |
| 22 | 22 | 43000 | 0.5 | 2.94 | 2.96 | 5.94 | N/A |
| 23 | 23 | 43000 | 0.5 | 2.94 | 2.95 | 5.92 | N/A |
| 24 | 24 | 43000 | 0.5 | 2.92 | 2.95 | 5.97 | N/A |
| 25 | 25 | 43000 | 0.5 | 2.95 | 2.98 | 6.01 | N/A |
| 26 | 26 | 43000 | 0.5 | 6.20 | 5.91 | 11.82 | N/A |
| 27 | 27 | 43000 | 0.5 | 2.92 | 0.76 | 2.97 | 0.79 mmol NAC, 7.36 mmol NHS |
| 28 | CS-cat, 28 | 43000 | 0.5 | 2.95 | 0.77 | 2.96 | N/A |
| 29 | CS-cat, 29 | 43000 | 0.5 | | | | |

*FIG. 12A*

| Batch # | Catechol CS ID# | CS Used | Starting % CS in soln. | mmol free amine | mmol HCA | mmol EDC HCl | mmol other |
|---|---|---|---|---|---|---|---|
| 30 | CS-cat, 30 | 43000 | 0.5 | 2.93 | 1.48 | 2.93 | N/A |
| 31 | CS-cat, 31 | 43000 | 0.5 | 8.74 | 10.39 | 12.98 | N/A |
| 32 | CS-cat, 32 | 43000 | 0.5 | 8.76 | 10.41 | 12.98 | N/A |
| 33 | CS-cat, 33 | 43000 | 0.5 | 2.95 | 1.49 | 2.94 | N/A |
| 34 | CS-cat, 34 | 43000 | 0.5 | 2.96 | 0.85 | 2.97 | 0.81 mmol NAC |
| 35 | CS-cat, 35 | 43000 | 0.5 | 8.75 | 2.39 | 8.76 | 2.36 mmol NAC |
| 36 | CS-cat, 36 | 43000 | 0.5 | 8.74 | 1.48 | 2.95 | N/A |
| 37 | CS-cat, 37 | 43000 | 0.5 | 8.73 | 10.41 | 12.99 | N/A |
| 38 | CS-cat, 38 | 43000 | 0.5 | 8.74 | 1.47 | 2.96 | N/A |
| 39 | CS-cat, 39 | 43000 | 0.5 | 8.74 | 2.39 | 8.75 | 2.40 mmol NAC |
| 40 | CS-cat, 40 | 43000 | 0.5 | 8.75 | 1.47 | 2.95 | N/A |
| 41 | CS-cat, 41 | 43000 | 0.5 | 8.79 | 1.48 | 2.96 | N/A |

*FIG. 12B*

| Dressing Preparation # | Formulation type | CS | CAT %Deg Subst. | %solute (w/w) in soln. | Mold pour depth (mm) | Estimated compress (mm) | Compressed Dressing ρ (g/cm2) | Compressed dressing information |
|---|---|---|---|---|---|---|---|---|
| 1 | 2% CS, 2% acetic acid (Control) | 65010 | N/A | 2 | 5 | 0.2 | 0.63 | |
| 2 | 100% CS-Cat, 1 | 65010 | NA | - | 5 | 0.1 | - | |
| 3 | 100% CS-Cat, 1 | 65010 | NA | - | 5 | 0.2 | - | |
| 4 | 100% CS-Cat, 2 | 43000 | 21.8 | 0.4 | 5 | 0.1 | 0.21 | |
| 5 | 25:75 CS-Cat, 2 | 43000 | 21.8 | - | 5 | 0.1 | | |
| 6 | 50:50 CS-Cat, 2 | 43000 | 21.8 | - | 5 | 0.1 | | |
| 7 | 75:25 CS-Cat, 2 | 43000 | 21.8 | - | 5 | 0.1 | | |
| 8 | 100% CS-Cat, 3 | 43000 | 11.5 | 0.5 | 5 | 0.1 | 0.25 | |
| 9 | 50:50 CS-Cat, 3 | 43000 | 11.5 | - | 5 | 0.1 | | |
| 10 | 75:25 CS-Cat, 3 | 43000 | 11.5 | - | 5 | 0.1 | | |
| 11 | 100% CS-Cat, 3 | 43000 | 11.5 | 0.5 | 5 | 0.1 | 0.25 | |
| 12 | 50:50 CS-Cat, 3 | 43000 | 11.5 | - | 5 | 0.1 | | |
| 13 | 75:25 CS-Cat, 3 | 43000 | 11.5 | - | 5 | 0.1 | | |
| 14 | Chitosan Lactate/Acetate | 65010 | - | 2.8 | 3 | 0.15 | 0.56 | |
| 15 | Chitosan, HPMC (90/10) | 65010 | - | 2.6 | 3 | 0.15 | 0.6 | |
| 16 | 2% CS, 2% acetic acid | 65010 | - | 2 | 3 | 0.1 | 0.6 | |
| 17 | 2% CS, 0.2% acetic acid | 65010 | - | 2 | 3 | 0.1 | 0.6 | > 98% dry |
| 18 | Chitosan, Polaxamer 90/10 | 65010 | - | 2.5 | 3 | 0.12 | 0.63 | |
| 19 | Chitosan: Sucrose 0.05% | 65010 | - | 2.2 | 3 | 0.12 | 0.55 | |
| 20 | Chitosan: Sucrose 0.1% | 65010 | - | 2 | 3 | 0.1 | 0.6 | |

*FIG. 12C*

| Dressing Preparation # | Formulation type | CS | CAT %Deg Subst. | %solute (w/w) in soln. | Mold pour depth (mm) | Estimated compress (mm) | Compressed Dressing ρ (g/cm2) | Compressed dressing information |
|---|---|---|---|---|---|---|---|---|
| 21 | 25:75 CS-Cat, 4:CS lactate/acetate | 43000 | 11.5 | - | 3 | 0.1 | | |
| 22 | 50:50 CS-Cat, 4:CS lactate/acetate | 43000 | 11.5 | - | 3 | 0.1 | | |
| 23 | 75:25 CS-Cat, 4:CS lactate/acetate | 43000 | 11.5 | - | 3 | 0.1 | | |
| 24 | 2% CS, 0.222% HPC | 65010 | - | 2.5 | 3 | 0.12 | 0.63 | |
| 25 | 2% CS, 0.222% HEC | 65010 | - | 2.5 | 3 | 0.12 | 0.63 | |
| 26 | 2% CS Control | 65010 | - | 2 | 3 | 0.1 | 0.6 | |
| 27 | 1% CS, 0.05% Sucrose | 65010 | - | 2 | 2 | 0.05 | 0.8 | |
| 28 | 2% CS, 0.05% Sorbitol | 65010 | - | 2 | 2 | 0.05 | 0.8 | |
| 29 | CS-catechol, batch 6 | 43000 | 7.5 | 0.4 | 3 | 0.05 | 0.24 | |
| 30 | CS-catechol, batch 8 | 43000 | - | - | 3 | 0.05 | | |
| 31 | CS-catechol, batch 9 | 43000 | - | 0.3 | 3 | 0.05 | 0.18 | |
| 32 | CS-catechol, batch 10 | 43000 | 17 | 0.7 | 3 | 0.05 | 0.42 | |
| 33 | CS-catechol, batch 11 | 43000 | 26 | 0.5 | 2 | 0.05 | 0.2 | |
| 34 | CS-catechol, Batch 12 | 43000 | - | - | 2 | 0.05 | | |
| 35 | CS-catechol, batch13 | 43000 | - | 0.7 | 3 | 0.05 | 0.42 | |
| 36 | CS-catechol, batch 14 | 65010 | - | 0.5 | 3 | 0.05 | 0.3 | |
| 37 | CS-catechol, batch 15 | 43000 | - | 0.4 | 3 | 0.05 | 0.24 | |
| 38 | CS-catechol, batch 16 | 43000 | 29 | 0.6 | 3 | 0.05 | 0.36 | |

*FIG. 12D*

| Dressing Preparation # | Formulation type | CS | CAT %Deg Subst. | %solute (w/w) in soln. | Mold pour depth (mm) | Estimated compress (mm) | Compressed Dressing ρ (g/cm2) | Compressed dressing information |
|---|---|---|---|---|---|---|---|---|
| 39 | CS-catechol, batch 16 | 43000 | 26 | 1.8 | 3 | 0.07 | 0.77 | |
| 40 | CS-catechol, batch 17 | 43000 | - | 0.6 | 3 | 0.05 | 0.36 | |
| 41 | CS-catechol, batch 18 | 43000 | - | 0.7 | 2 | 0.05 | 0.28 | |
| 42 | CS-catechol, batch 19 | 43000 | - | 0.5 | 2 | 0.05 | 0.20 | |
| 43 | CS-catechol, batch 20 | 43000 | - | - | 3 | 0.05 | | |
| 44 | CS-catechol, batch 21 | 43000 | - | - | 3 | 0.05 | | |
| 45 | CS-catechol, batch 22-1 | 43000 | 7 | 1.6 | 3 | 0.07 | 0.68 | |
| 46 | CS-catechol, batch 22-2 | 43000 | - | 1.1 | 3 | 0.05 | 0.66 | |
| 47 | CS-catechol, bacth 23 | 43000 | 13 | 0.4 | 3 | 0.05 | 0.24 | |
| 48 | CS-catechol, batch 24 | 43000 | 20 | 0.3 | 3 | 0.05 | 0.18 | |
| 49 | CS-catechol, batch 25 | 43000 | 15 | 0.4 | 3 | 0.05 | 0.24 | |
| 50 | CS-catechol, batch 26 | 43000 | 25 | 0.35 | 10 | 0.05 | 0.7 | |
| 51 | CS-catechol, batch 27 | 43000 | 18 | 0.3 | 10 | 0.05 | 0.6 | |
| 52 | CS-catechol, batch 26 | 43000 | 25 | 1.0 | 4 | 0.05 | 0.8 | |
| 53 | CS-catechol, batch 25 | 43000 | 15 | 2.0 | 2 | 0.05 | 0.8 | |
| 54 | CS-catechol, batch 28 | 43000 | 26 | 0.3 | 5 | 0.05 | 0.3 | |
| 55 | 50/50 CS-cat, 28/CS | 43000 | - | 0.5 | 5 | 0.05 | 0.5 | |
| 56 | 65/35 CS-cat, 28/CS | 43000 | - | 0.5 | 5 | 0.05 | 0.5 | |
| 57 | CS-catechol, batch 29 | 43000 | - | 0.3 | 5 | 0.05 | 0.3 | |
| 58 | CS-catechol, thiolated | 43000 | 21 | 0.35 | 5 | 0.05 | 0.7 | |
| 59 | 50/50 CS-cat, thiolated/CS | 43000 | - | 0.5 | 5 | 0.05 | 0.5 | |

FIG. 12E

| Dressing Preparation # | Formulation type | CS | CAT %Deg Subst. | %solute (w/w) in soln. | Mold pour depth (mm) | Estimated compress (mm) | Compressed Dressing ρ (g/cm2) | Compressed dressing information |
|---|---|---|---|---|---|---|---|---|
| 60 | 65/35 CS-cat, thiolated/CS | 43000 | - | 0.5 | 5 | 0.05 | 0.5 | |
| 61 | 51/49 CS-cat, thiolated/CS | 43000 | - | 0.5 | 5 | 0.05 | 0.5 | |
| 62 | 75/25 CS-cat, thiolated/CS | 43000 | - | 0.5 | 5 | 0.05 | 0.5 | |
| 63 | CS-catechol, batch 30 | 43000 | 21.74 | 0.5 | 5 | 0.05 | 0.5 | |
| 64 | CS-catechol, batch 31a | 43000 | - | 0.4 | 5 | 0.05 | 0.4 | |
| 65 | CS-catechol, batch 31b | 43000 | - | 0.4 | 5 | 0.05 | 0.4 | |
| 66 | CS-catechol, batch 31c | 43000 | - | 0.4 | 5 | 0.05 | 0.4 | |
| 67 | CS-catechol, batch 32 | 43000 | - | 0.5 | 7 | 0.05 | 0.7 | |
| 68 | CS-catechol, batch 32 | 43000 | - | 0.5 | 7 | 0.05 | 0.7 | |
| 69 | CS-catechol, batch 32 | 43000 | - | 0.5 | 7 | 0.05 | 0.7 | |
| 70 | CS-catechol, batch 32 | 43000 | - | 0.5 | 8 | 0.05 | 0.8 | |
| 71 | CS-catechol, batch 32 | 43000 | - | 0.5 | 7 | 0.05 | 0.7 | CS backed |
| 72 | 65/35 CS-cat, 32/CS | 43000 | - | 0.5 | 5 | 0.05 | 0.5 | |
| 73 | 50/50 CS-cat, 32/CS | 43000 | - | 0.5 | 5 | 0.05 | 0.5 | |
| 74 | 70/30 CS-cat, 32/CS | 43000 | - | 0.5 | 5 | 0.05 | 0.5 | |
| 75 | CS-catechol, batch 33 | 43000 | - | 0.5 | 5 | 0.05 | 0.5 | |
| 76 | CS-catechol, batch 34 | 43000 | - | 0.5 | 5 | 0.05 | 0.5 | |
| 77 | CS-catechol, batch 35 | 43000 | - | 0.5 | 5 | 0.05 | 0.5 | |
| 78 | 70/30 CS-cat 35/CS | 43000 | - | 0.5 | 5 | 0.05 | 0.5 | |
| 79 | 70/30 CS-cat 35/CS | 43000 | - | 0.5 | 5 | 0.05 | 0.5 | CS backed |
| 80 | CS-catechol, batch 36 | 43000 | - | 0.5 | 3 | 0.05 | 0.3 | CS backed |

*FIG. 12F*

| Dressing Preparation # | Formulation type | CS | CAT %Deg Subst. | %solute (w/w) in soln. | Mold pour depth (mm) | Estimated compress (mm) | Compressed Dressing ρ (g/cm2) | Compressed dressing information |
|---|---|---|---|---|---|---|---|---|
| 81 | CS-catechol, batch 37 | 43000 | - | 0.5 | 5 | 0.05 | 0.5 | |
| 82 | CS-catechol, batch 38 | 43000 | - | 0.5 | 5 | 0.05 | 0.5 | |
| 83 | 70/30 CS-catechol, batch 39/CS | 43000 | - | 0.5 | 5 | 0.05 | 0.5 | CS backed |
| 84 | CS-catechol, batch 40 | 43000 | - | 0.5 | 5 | 0.05 | 0.5 | CS backed |
| 85 | CS-catechol, batch 41 | 43000 | - | 0.5 | 5 | 0.05 | 0.5 | CS backed |

*FIG. 12G*

| Dressing Preparation # | Formulation type | Time to dissolution (hours) | Foldability F = Fail P= Pass | Burst Testing | Ex-Vivo | Accelerated Stability | In-Vivo |
|---|---|---|---|---|---|---|---|
| 1 | 2% CS, 2% acetic acid (Co-rol) | 2 | F | - | - | - | - |
| 2 | 100% CS-Cat, 1 | - | P | - | - | - | - |
| 3 | 100% CS-Cat, 1 | - | P | - | - | - | - |
| 4 | 100% CS-Cat, 2 | 61.7 | P | - | - | - | - |
| 5 | 25:75 CS-Cat, 2 | 15.6 | P | - | - | - | - |
| 6 | 50:50 CS-Cat, 2 | 35.7 | P | - | - | - | - |
| 7 | 75:25 CS-Cat, 2 | 168 | P | - | - | - | - |
| 8 | 100% CS-Cat, 3 | - | P | - | - | - | - |
| 9 | 50:50 CS-Cat, 3 | 27 | P | - | - | - | - |
| 10 | 75:25 CS-Cat, 3 | 57.8 | P | - | - | - | - |
| 11 | 100% CS-Cat, 3 | 68.8 | P | - | - | - | - |
| 12 | 50:50 CS-Cat, 3 | 31.7 | P | - | - | - | - |
| 13 | 75:25 CS-Cat, 3 | 68.5 | P | - | - | - | - |
| 14 | Chitosan Lactate/Acetate | 5.8 | F | - | - | - | - |
| 15 | Chitosan, HPMC (90/10) | 2.8 | F | - | - | - | - |
| 16 | 2% CS, 2% acetic acid | 0.7 | F | - | - | - | - |
| 17 | 2% CS, 0.2% acetic acid | 1.8 | F | - | - | - | - |
| 18 | Chitosan, Polaxamer 90/10 | 1.5 | F | - | - | - | - |
| 19 | Chitosan: Sucrose 0.05% | 6.7 | F | - | - | - | - |
| 20 | Chitosan: Sucrose 0.1% | 1 | F | - | - | - | - |

*FIG. 13A*

| Dressing Preparation # | Formulation type | Time to dissolution (hours) | Foldability F = Fail P= Pass | Burst Testing | Ex-Vivo | Accelerated Stability | In-Vivo |
|---|---|---|---|---|---|---|---|
| 21 | 25:75 CS-Cat, 4:CS lactate/acetate | 2 | P | - | - | - | - |
| 22 | 50:50 CS-Cat, 4:CS lactate/acetate | 2 | P | - | - | - | - |
| 23 | 75:25 CS-Cat, 4:CS lactate/acetate | 2 | P | - | - | - | - |
| 24 | 2% CS, 0.222% HPC | - | F | - | - | - | - |
| 25 | 2% CS, 0.222% HEC | - | F | - | - | - | - |
| 26 | 2% CS Co-rol | - | F | - | - | - | - |
| 27 | 1% CS, 0.05% Sucrose | 6.7 | F | - | - | - | - |
| 28 | 2% CS, 0.05% Sorbitol | 19 | F | - | - | - | - |
| 29 | CS-catechol, batch 6 | 120 | P | - | - | - | - |
| 30 | CS-catechol, batch 8 | 92 | P | - | - | - | - |
| 31 | CS-catechol, batch 9 | NA | P | - | - | - | - |
| 32 | CS-catechol, batch 10 | 16.3 | P | - | - | - | - |
| 33 | CS-catechol, batch 11 | 26 | P | - | - | - | - |
| 34 | CS-catechol, Batch 12 | NA | P | - | - | - | - |
| 35 | CS-catechol, batch13 | 27 | P | - | - | - | - |
| 36 | CS-catechol, batch 14 | 46 | P | - | - | - | - |
| 37 | CS-catechol, batch 15 | 27 | P | - | - | - | - |
| 38 | CS-catechol, batch 16 | - | P | - | - | - | - |
| 39 | CS-catechol, batch 16 | 32 | F | - | - | - | - |
| 40 | CS-catechol, batch 17 | 20 | P | - | - | - | - |

*FIG. 13B*

| Dressing Preparation # | Formulation type | Time to dissolution (hours) | Foldability F = Fail P= Pass | Burst Testing | Ex-Vivo | Accelerated Stability | In-Vivo |
|---|---|---|---|---|---|---|---|
| 41 | CS-catechol, batch 18 | 57.8 | P | - | - | - | - |
| 42 | CS-catechol, batch 19 | 13.6 | P | - | - | - | - |
| 43 | CS-catechol, batch 20 | 23 | P | - | - | - | - |
| 44 | CS-catechol, batch 21 | 71.7 | P | - | - | - | - |
| 45 | CS-catechol, batch 22-1 | 46 | P | - | - | - | - |
| 46 | CS-catechol, batch 22-2 | 71 | P | - | - | - | - |
| 47 | CS-catechol, bacth 23 | 24 | P | - | - | - | - |
| 48 | CS-catechol, batch 24 | 23 | P | - | - | - | - |
| 49 | CS-catechol, batch 25 | 14.8 | P | - | - | - | - |
| 50 | CS-catechol, batch 26 | - | P | - | - | - | - |
| 51 | CS-catechol, batch 27 | - | P | - | - | - | - |
| 52 | CS-catechol, batch 26 | - | P | - | - | - | - |
| 53 | CS-catechol, batch 25 | - | P | - | - | - | - |
| 54 | CS-catechol, batch 28 | | P | - | - | - | - |
| 55 | 50/50 CS-cat, 28/CS | 65 | P | - | - | - | - |
| 56 | 65/35 CS-cat, 28/CS | 44 | P | - | - | - | - |
| 57 | CS-catechol, batch 29 | | P | - | - | - | - |
| 58 | CS-catechol, thiolated | | P | - | - | - | - |
| 59 | 50/50 CS-cat, thiolated/CS | 47 | P | - | - | - | - |
| 60 | 65/35 CS-cat, thiolated/CS | 84.2 | P | - | - | - | - |

*FIG. 13C*

| Dressing Preparation # | Formulation type | Time to dissolution (hours) | Foldability F = Fail P= Pass | Burst Testing | Ex-Vivo | Accelerated Stability | In-Vivo |
|---|---|---|---|---|---|---|---|
| 61 | 51/49 CS-cat, thiolated/CS | 43.3 | P | - | - | - | - |
| 62 | 75/25 CS-cat, thiolated/CS | 71 | P | - | - | - | - |
| 63 | CS-catechol, batch 30 | 90 | P | - | - | - | - |
| 64 | CS-catechol, batch 31a | 156.7 | P | - | - | - | - |
| 65 | CS-catechol, batch 31b | 133.3 | P | - | - | - | - |
| 66 | CS-catechol, batch 31c | 122 | P | - | - | - | - |
| 67 | CS-catechol, batch 32 | 128.3 | P | - | - | - | - |
| 68 | CS-catechol, batch 32 | 144.5 | P | - | - | - | - |
| 69 | CS-catechol, batch 32 | 200 | P | - | - | - | - |
| 70 | CS-catechol, batch 32 | 240 | P | - | - | - | A, Acute In-Vivo 1 |
| 71 | CS-catechol, batch 32 | 215 | P w/backing | - | - | - | - |
| 72 | 65/35 CS-cat, 32/CS | 107.6 | P | - | - | - | - |
| 73 | 50/50 CS-cat, 32/CS | 9.5 | P | - | - | - | - |
| 74 | 70/30 CS-cat, 32/CS | 142 | P | - | - | - | C, Acute In-Vivo 1 |
| 75 | CS-catechol, batch 33 | 109.8 | P | - | - | - | - |
| 76 | CS-catechol, batch 34 | - | P | - | - | - | - |
| 77 | CS-catechol, batch 35 | - | - | - | - | - | B, Acute In-Vivo 1 |
| 78 | 70/30 CS-cat 35/CS | 66 | P | - | - | - | |

*FIG. 13D*

| Dressing Preparation # | Formulation type | Time to dissolution (hours) | Foldability F = Fail P= Pass | Burst Testing | Ex-Vivo | Accelerated Stability | In-Vivo |
|---|---|---|---|---|---|---|---|
| 79 | 70/30 CS-cat 35/CS | 59.3 | P | - | - | - | - |
| 80 | CS-catechol, batch 36 | 65.5 | P | - | Y | - | C, Acute In-Vivo 2 |
| 81 | CS-catechol, batch 37 | | P | - | - | - | A, Acute In-Vivo 2 |
| 82 | CS-catechol, batch 38 | | P | - | - | - | - |
| 83 | 70/30 CS-catechol, batch 39/CS | 168 | P | Y | Y | 6 mo-hs | B, Acute In-Vivo 2 |
| 84 | CS-catechol, batch 40 | 168 | P | Y | - | 6 mo-hs | C, Chronic In-Vivo |
| 85 | CS-catechol, batch 41 | - | P | Y | - | - | - |

*FIG. 13E*

| Code # | Prototype | Layer | Test tube Test (mins) | Beaker Test (hours) | Fold-ability | In vivo screen #1 | In vivo screen #2 | In vivo screen #3 |
|---|---|---|---|---|---|---|---|---|
| A01 | 2Ch | N | | 0 | Y | | | |
| A02 | 2Ch | N | | 0 | Y | | | |
| A03 | 2Ch | N | | 0 | Y | | | |
| A04 | 4Ch | N | | >8 | Y | | | |
| A05 | 2ChGylcer | N | <15 | | | | | |
| A06 | 2Ch1cell | N | | 0 | Y | | | |
| A07 | 2Ch1Gel | N | | 1 | Y | N | | |
| A08 | 10Gel | N | | | N | | N | |
| A09 | 2PAA | N | | | N | | | |
| A10 | 1PAA | N | | 1 | Y | N | | |
| A11 | 2PAA | N | | 0 | N | | | |
| A12 | 0.3PAA | N | | | N | | | |
| B01 | 2Ch35DDA1 | N | <15 | | | | | |
| B02 | 2Ch35DDA2 | N | <15 | | | | | |
| B03 | 2Ch40DDA1 | N | <15 | | | | | |
| B04 | 2Ch40DDA2 | N | <15 | | | | | |
| C01 | 5Starch | N | <15 | | | | | |
| C02 | 3Pectin | N | <15 | | | | | |
| C03 | 3Guar | N | >60 | | | | | |
| C03-2 | 3Gu | N | | >7 | N | N | | |
| C04 | 3.5Gu | N | | 24 | N | | | |
| C05 | 2Gu1cel | N | | 0 | N | | | |
| C06 | 3Gu0.1Pol | N | | >4 | N | | | |
| C06-2 | 3Gu0.1Pol | N | | >4 | N | | | |
| C07 | 3.5Gu0.1Pol | N | | 23 | N | Y | | |

*FIG. 16A*

| Code # | Prototype | Layer | Test tube Test (mins) | Beaker Test (hours) | Fold-ability | In vivo screen #1 | In vivo screen #2 | In vivo screen #3 |
|---|---|---|---|---|---|---|---|---|
| D01 | 1Ch5Starch1 | N | <15 | 2 | N | | | |
| D02 | 1Ch1Pectin1 | N | <15 | | | | | |
| D03 | 1Ch1Guar1 | N | >60 | 2 | Y | | | |
| D04 | 1Ch5Starch2 | Y | <15 | | Y (cracks) | | | |
| D05 | 1Ch1Pectin2 | Y | <15 | | | | | |
| D06 | 1Ch1Guar1 | Y | >60 | 0.25/6-17 | Y (cracks) | | | |
| D07 | 4Ch2.5Gu | Y | | 0.25/6-23 | Y (cracks) | | | |
| D08 | 2Ch2.5Gu | Y | | 0.25/3-19 | Y (cracks) | | | |
| D09 | 4Ch2.5Gu | Y | | | Y (cracks) | | | |
| D10 | 2Ch2.5Gu | Y | | | Y (cracks) | | | |
| D11 | 2Ch1Gu | N | | | Y (cracks) | | | |
| D12 | 3Ch0.6Gu | N | | 3 | Y (cracks) | | | |
| D13 | 2Ch1.25Gu | N | | 3 | Y (cracks) | | | |
| D14 | 1Ch1.9Gu | N | | 2 | Y (cracks) | | | |
| D15 | 0.7Ch2.1Gu | N | | 2 | Y (cracks) | | | |
| D16 | 1.5Gu1Cat | N | | 2 | Y (cracks) | | | |
| D17 | 4Ch3Gu | N | | 3 | N | | | |
| D18 | 2Ch2Gu | N | | >5 | N | | | |
| D19 | 3Gu4Ch | Y | | 24 | Y (cracks) | N | | |
| D20 | 3Gu0.1Pol4Ch | Y | | 0 | Y | | | |
| D21 | 0.1PAA2Gu | N | | | Y (cracks) | | | |
| D22 | 1PAA3Gu | N | | 31 | N | N, N, N | | |
| D23 | 1PAA2Gu | N | | 48 | N | N | | |
| D24 | 4Ch0.1Pect | N | | 2-19 | Y | Y, N | Y, Y, Y, Y | N, Y, Y, N |

*FIG. 16B*

| Code # | Prototype | Layer | Test tube Test (mins) | Beaker Test (hours) | Fold-ability | In vivo screen #1 | In vivo screen #2 | In vivo screen #3 |
|---|---|---|---|---|---|---|---|---|
| E1 | ChCatechol | N | | 42 | Y | Y, N, Y, | Y, N, N, N | N, N, N, N |
| E2 | ChCatechol | N | | | Y | Y, N | N, N, N, N, N | N, Y, Y, Y, N, N, N |
| F01 | 2Ch1Cat1Gu | Y | | | Y (cracks) | | | |
| F02 | 1Cat1Gu | N | | | Y | N | | |
| F03 | 1Cat3Gu | N | | >6 | N | N | | |
| F04 | 0.5Cat1Gu0.5Ch | N | | | N | | | |
| F05 | 0.5Cat3Gu0.5Ch | N | | >6 | N | Y | | |
| F06 | 1Cat1PAA | N | | | N | N | | |
| F07 | 1Cat1Gu1PAA | N | | | Y | | | |
| F08 | 1Cat3Gu1PAA | N | | | Y | | | |
| F09 | 1Cat0.25Gu0.25PAA | N | | | Y | | | |
| F10 | 1Cat1Gu0.25PAA | N | | | Y | | | |
| F11 | 0.25Cat1.5Ch | N | | 2 | Y | | N, Y, Y, Y | N, N, Y, Y |
| F12 | 0.75Cat0.5Ch | N | | | N | | Y, N, N, N, | Y, N, Y, Y |
| F13 | 0.75cat0.5Ch1Gu | N | | | | | N | |
| F14 | 0.5Cat1.5Ch | N | | | Y | | N, Y, N, N, | |
| G01 | Nanofiber 12GSM | N | | 2 | Y | Y | N, Y, N, N, Y | Y, Y, Y, Y |
| H01 | PatchPro | NA | | NA | NA | Y | Y | |
| H02 | Gauze | NA | | NA | NA | | N, N, N, Y, N | N, N, Y, Y |

FIG. 16C

| Code # | Prototype | % Chitosan | Chitosan Lot | % Acetic Acid | %DDA | % Chitosan Catechol | Catechol Approach | %PAA | %Starch | %Pectin | %Guar | Mixture | Layer | Chitin microfiber | Notes 1 |
|---|---|---|---|---|---|---|---|---|---|---|---|---|---|---|---|
| A01 | 2Ch | 2 | A | 2 | 80 | | | | | | | | | | |
| A02 | 2Ch | 2 | B | 1 | 95 | | | | | | | | | | |
| A03 | 2Ch | 2 | B | 2 | 95 | | | | | | | | | | |
| A04 | 4Ch | 4 | B | 2 | 95 | | | | | | | | | | |
| A05 | 2ChGylcer | 2 | A | 2 | 40 | | | | | | | | | | +2% glycerol |
| A06 | 2Ch1cell | 2 | A | 1 | 80 | | | | | | | Yes | | | 1%cellulose |
| A07 | 2Ch1Gel | 2 | A | 1 | 80 | | | | | | | Yes | | | 1% Gelatin |
| A08 | 10Gel | | | | | | | | | | | | | | 10% Gelatin |
| A09 | 2PAA | | | | | | | 2 | | | | | | | |
| A10 | 1PAA | | | | | | | 1 | | | | | | | |
| A11 | 2PAA | | | | | | | 2 | | | | | | | |
| A12 | 0.3PAA | | | | | | | 0.25 | | | | | | | |
| | | | | | | | | | | | | | | | |
| B01 | 2Ch35DDA1 | 2 | A | 2 | 35 | | | | | | | | | Yes | 0.1% chitin |
| B02 | 2Ch35DDA2 | 2 | A | 2 | 35 | | | | | | | | | | |
| B03 | 2Ch40DDA1 | 2 | A | 2 | 40 | | | | | | | | | Yes | 0.1% chitin |
| B04 | 2Ch40DDA2 | 2 | A | 2 | 40 | | | | | | | | | | |
| | | | | | | | | | | | | | | | |
| C01 | 5Starch | | | | | | | | 5 | | | | | | single polymer |
| C02 | 3Pectin | | | | | | | | | 3 | | | | | single polymer |
| C03 | 3Guar | | | | | | | | | | 3 | | | | single polymer |
| C03-2 | 3Gu | | | | | | | | | | 3 | | | | |
| C04 | 3.5Gu | | | | | | | | | | 3.5 | | | | |
| C05 | 2Gu1cel | | | | | | | | | | 2 | Yes | | | 1% cellulose |
| C06 | 3Gu0.1Pol | | | | | | | | | | 3 | Yes | | | 0.1 Polox |
| C06-2 | 3Gu0.1Pol | | | | | | | | | | 3 | Yes | | | 0.1% Polox |
| C07 | 3.5Gu0.1Pol | | | | | | | | | | 3.5 | Yes | | | 0.1% Polox |

*FIG. 17A*

| Code # | Prototype | % Chitosan | Chitosan Lot | % Acetic Acid | %DDA | % Chitosan Catechol | Catechol Approach | %PAA | %Starch | %Pectin | %Guar | Mixture | Layer | Chitin microfiber | Notes 1 |
|---|---|---|---|---|---|---|---|---|---|---|---|---|---|---|---|
| D01 | 1Ch5Starch1 | 1 | A | 1 | 80 | | | | 5 | | | Yes | | | |
| D02 | 1Ch1Pectin1 | 1 | A | 1 | 80 | | | | | 1 | | Yes | | | |
| D03 | 1Ch1Guar1 | 1 | A | 1 | 80 | | | | | | 1 | Yes | | | |
| D04 | 1Ch5Starch2 | 1 | A | 1 | 80 | | | | 5 | | | | Yes | | |
| D05 | 1Ch1Pectin2 | 2 | A | 2 | 80 | | | | | 1 | | | Yes | | |
| D06 | 1Ch1Guar1 | 2 | A | 2 | 80 | | | | | | 1 | | Yes | | |
| D07 | 4Ch2.5Gu | 4 | B | 2 | 95 | | | | | | 2.5 | | Yes | | |
| D08 | 2Ch2.5Gu | 2 | B | 2 | 95 | | | | | | 2.5 | | Yes | | |
| D09 | 4Ch2.5Gu | 4 | B | 2 | 95 | | | | | | 2.5 | | Yes | | |
| D10 | 2Ch2.5Gu | 2 | B | 2 | 95 | | | | | | 2.5 | | Yes | | ↑guar layer |
| D11 | 2Ch1Gu | 2 | B | 2 | 95 | | | | | | 1.25 | Yes | | | |
| D12 | 3Ch0.6Gu | 3 | B | 2 | 95 | | | | | | 0.625 | Yes | | | |
| D13 | 2Ch1.25Gu | 2 | B | 2 | 95 | | | | | | 1.25 | Yes | | | |
| D14 | 1Ch1.9Gu | 1 | B | 2 | 95 | | | | | | 1.875 | Yes | | | |
| D15 | 0.7Ch2.1Gu | 0.68 | B | 2 | 95 | | | | | | 2.075 | Yes | | | |
| D16 | 1.5Gu1Cat | | | | | 1 | 1 | | | | 1.5 | Yes | | | |
| D17 | 4Ch3Gu | 4 | B | 2 | 95 | | | | | | 3 | Yes | | | |
| D18 | 2Ch2Gu | 2 | A | 2 | 80 | | | | | | 2 | Yes | | | |
| D19 | 3Gu4Ch | 4 | B | 2 | 95 | | | | | | 3 | | Yes | | |
| D20 | 3Gu0.1Pol4Ch | 4 | B | 2 | 95 | | | | | | 3 | Yes | Yes | | Gu+0.1% Polox |
| D21 | 0.1PAA2Gu | | | | | | | 0.07 | | | 2.21 | Yes | | | |
| D22 | 1PAA3Gu | | | | | | | 1 | | | 3 | Yes | | | |
| D23 | 1PAA2Gu | | | | | | | 1 | | | 2 | Yes | | | |
| D24 | 4Ch0.1Pect | 4 | B | 2 | 95 | | | | | | | Yes | | | 0.1 Pectin |
| E01 | ChCatechol | | | | | 1 | 2 | | | | | | | | |
| E02 | ChCatechol | | | | | 1 | 3 | | | | | | | | |

*FIG. 17B*

| Code # | Prototype | % Chitosan | Chitosan Lot | % Acetic Acid | %DDA | % Chitosan Catechol | Catechol Approach | %PAA | %Starch | %Pectin | %Guar | Mixture | Layer | Chitin microfiber | Notes 1 |
|---|---|---|---|---|---|---|---|---|---|---|---|---|---|---|---|
| F01 | 2Ch1Cat1Gu | 2 | B | 2 | 95 | 1 | 3 | | | | 2.5 | | Yes | | |
| F02 | 1Cat1Gu | | | | | 1 | 1 | | | | 1 | Yes | | | |
| F03 | 1Cat3Gu | | | | | 1 | 1 | | | | 3 | Yes | | | |
| F04 | 0.5Cat1Gu0.5Ch | 0.5 | A | 1 | 80 | 0.5 | 1 | | | | 1 | Yes | | | |
| F05 | 0.5Cat3Gu0.5Ch | 0.5 | A | 1 | 80 | 0.5 | 1 | | | | 3 | Yes | | | |
| F06 | 1Cat1PAA | | | | | 1 | 1 | 1 | | | | Yes | | | |
| F07 | 1Cat1Gu1PAA | | | | | 1 | 1 | 1 | | | 1 | Yes | | | |
| F08 | 1Cat3Gu1PAA | | | | | 1 | 1 | 1 | | | 3 | Yes | | | |
| F09 | 1Cat0.25Gu0.25PAA | | | | | 1 | 1 | 0.25 | | | 0.25 | Yes | | | |
| F10 | 1Cat1Gu0.25PAA | | | | | 1 | 1 | 0.25 | | | 1 | Yes | | | |
| F11 | 0.25Cat1.5Ch | 1.5 | A | 1 | 80 | 0.25 | 2 | | | | | Yes | | | |
| F12 | 0.75Cat0.5Ch | 0.5 | A | 1 | 80 | 0.75 | 1 | | | | | Yes | | | |
| F13 | 0.75cat0.5Ch 1Gu | 0.5 | A | 1 | 80 | 0.75 | 3 | | | | 1 | Yes | | | |
| F14 | 0.5Cat1.5Ch | 1.5 | A | 2 | 80 | 0.5 | 3 | | | | | Yes | | | |
| G01 | Nanofiber 12GSM | | | | | | | | | | | | | | |

*FIG. 17C*

TISSUE ADHERENT CHITOSAN MATERIAL THAT RESISTS DISSOLUTION

GOVERNMENT LICENSE RIGHTS

This invention was made with Government support under R42DK078400 and R44DK104564 awarded by National Institute of Diabetes and Digestive and Kidney Disease. The Government has certain right in the invention.

BACKGROUND

Technical Field

Safe, reliable and effective delivery of bioactive chitosan material within the body remains a major problem. In use, the bioactive chitosan material must remain intact for a period of at least 12 hours in the presence of biological fluids such as gastric fluid, blood, bile and urine and it must be able to adhere to tissue including mucosa of the gastrointestinal tract and the internal elastic lamina of the vascular system for a period longer than 24 hours. Bioactive chitosan has many applications in the body not limited to drug delivery, hemostasis, wound healing, tissue regeneration, and embolotherapy. Current chitosan materials and compositions of chitosan material used on, or within the body are limited in their application as they are unable to resist dissolution and rapid loss in harsh environments such as the stomach and they cannot be maintained in place by their adhesion to tissue.

This disclosure relates to the field of chitosan materials comprising catechol modified chitosan and uses thereof.

Description of the Related Art

There are many surgeries on vascularized organs and tissue such as heart, liver, pancreas, stomach, intestine, colon, prostate, tonsils, ear, nose, throat and brain that often continue to bleed following injury and through wound healing. The initial injury may continue to bleed for days unless standard hemostasis is applied and the bleeding may also recur at a later time. Standard of care initial hemostasis for treatment of bleeding following surgery is varied depending on the type of surgery. Ligature, gauze packing, biologic dressings, cautery, and banding may be applied to locally address the issue. Packing may be applied for up to 24 hours in the case of protracted bleeding. If the bleeding is uncontrollable after the period of conservational management, the patient may have to return to surgical unit promptly to stop the hemorrhaging with either open or endoscopic procedures. Although there have been advances in bleeding control using advanced dressings none of these advances have yet translated into reliable treatment options under unique surgical conditions where delivery, tissue adhesion, and continuous bleeding intermingled with other biological fluid considerations are highly challenging. Rapid bleeding control under all circumstances is highly desirable.

Minimally invasive surgical procedures are becoming the preferred means of interventional access due to ability to access areas of the body with significantly reduced risk (compared to open surgery) with lower morbidity, lower hospital cost and lower patient discomfort. Advanced biomaterials are at the forefront of addressing current limitations and enabling improvements in safety, reliability and increased practice and application of minimally invasive surgical procedures. Current limitations in minimally invasive surgical practice include control of bleeding (especially hemorrhage), sutureless closure of delicate soft tissue sites, local promotion of healing, local treatment of pathogenic conditions, and local placement with anchoring or adhesion to a surgical/interventional site. More recently minimally invasive interventions are being used to address vascular pathogenesis including vascular malformations, aneurysms, and vascular tumors. A preferred procedure to address vascular malformations, aneurysms, and vascular tumors is the use of embolotherapy to occlude abnormal blood vessels. Embolotherapy involves the local delivery of an occlusion device such as a stent or a coil of material or an anchored biomaterial which remain in place over an extended time to promote the formation of a lot clot with subsequent permanent closure of the vessel.

A biocompatible, tissue adhesive, chitosan material that remains intact for a prolonged time with promotion of local clot formation and normal tissue healing presents advanced material attributes that will enable significant development in surgical practice.

In addition, prolonged bleeding, with its associated risks in mortality and morbidity, remains a serious problem in the gastrointestinal (GI) tract. Techniques and devices that could provide for rapid bleeding control in gastrointestinal bleeding (GIB) for both upper gastrointestinal bleeding (UGIB) and lower gastrointestinal bleeding (LGIB) are needed. Current bleeding control in and after transurethral resection of the prostate (TURP) relies on cautery for small vessel arterial bleeding and application of balloon pressure to address venous oozing. The bladder neck and prostrate are both highly vascularized tissue that often continue to bleed following injury and through wound healing. The initial injury site may continue to bleed for days unless standard hemostasis is applied and the bleeding may also recur around week one or week two after TURP procedure when the scab of prostatic cavity sheds off. Current standard initial hemostasis for treatment of bleeding following TURP is to apply manual traction with a balloon catheter followed by continuous bladder irrigation with saline. Typically, balloon pressure can be applied for up to 24 hours in the case of protracted bleeding. If the bleeding is uncontrollable after the period of conservational management, the patient may have to return to surgical unit promptly to stop the hemorrhaging with either open or endoscopic procedures.

Although there have been advances in bleeding control using advanced dressings for applications outside of GIB or TURP bleeding control, none of these advances have yet translated to the unique conditions of the gastrointestinal tract or bladder and especially the upper gastrointestinal tract and prostrate where delivery, adhesion, enzyme activity, continuous oozing bleeding, acidity, and urine-related considerations are highly challenging. Rapid bleeding control in TURP, in open prostatectomy and in bladder resection is highly desirable.

Gastrointestinal bleeding (GIB) is a common presentation to the emergency department. According to the U.S. Department of Health and Human Service, from 2000 to 2014, there was an average of over 350,000 discharges from gastrointestinal hemorrhage annually. In the U.S., the direct hospital cost in 2010 due to GIB exceeded $1.1 billion [1]. Upper GIB (UGIB), defined as gastrointestinal bleeding proximal to the ligament of Treitz, is approximately five times more common than lower GIB (LGIB) [2]. Acute UGIB is a potentially life-threatening emergency that necessitates prompt assessment, resuscitation and appropriate medical and endoscopic management. Despite recent advances in management of GIB in western countries, the mortality rate of acute UGIB has not significantly improved, and remains as high as 10-14% [3, 4]. The major cause of death after GIB is death secondary to cardiorespiratory complications, which is not surprising given the burden of comorbidities in such patients; death due to uncontrollable hemorrhage is reported to account for between 20% and 25% of cases [5, 6]. While little can be done to correct comorbidities urgently, more effective and rapid bleeding control will allow significant reductions in the incidence of UGIB related morbidity and mortality. In general, the most common causes of acute UGIB are peptic ulcers, gastro-esophageal varices, Mallory-Weiss tears and erosive esophagogastritis [7]. Nonvariceal upper gastrointestinal bleeding (NVUGIB) encompasses all causes of UGIB except bleeding esophageal or gastric varices. The incidence of peptic ulcer disease has decreased because of the development and utilization of proton pump inhibitors as well as the identification, treatment and eradication of *Helicobacter pylori* in individual patients [8]. Despite decreased peptide ulcer incidence, mortality among NVUGIB patients ranges from 3-4% [9]. While rarely life threatening, gastric malignancies can lead to friable tissue with diffuse bleeding that is difficult to address with traditional physical hemostatic methods (clips, bands, ligation) or cautery [10].

Current endoscopic management of patients with acute UGIB includes thermal therapy (e.g., bipolar electrocoagulation, heater probe, monopolar electrocoagulation, argon plasma coagulation, and laser), injection (epinephrine, sclerosants (e.g., absolute ethanol, polidocanol, and ethanolamine)), thrombin or fibrin glue (thrombin plus fibrinogen)), and clips [11, 12].

In general, the majority of patients with bleeding peptic ulcers, hemostasis is achieved with combination of the above endoscopic therapeutic modalities. However, there remains a subset of patients, approximately 5%, in which endoscopic treatments are not sufficient for hemostasis and thus require interventional radiology or surgical interventions [13, 14].

Endoscopic therapy fails for a variety of reasons including poor visibility of lesion due to active pulsating bleeding, difficult anatomic location of lesion for endoscopy, maximal therapy with currently available tools, and severe coagulopathy. Only available outside the United States, three different spray-based, hemostatic powder products and devices sold under the trademarks BLOODSTOPPER® (Ankaferd Blood Stopper, Turkey)[15], ENDOCLOT® (Olympus Corp., Japan) [16] and HEMOSPRAY® (Cook Medical LLC, US) [17-19] are also being considered to control NVUGIB. A potential concern with Hemospray is that it is a related product to WOUNDSTAT (Traumacure, Inc., US) which was withdrawn in 2009 in the United States due to its pro-clotting nanoparticulate bentonite promoting diffuse micro-emboli [20] that could cause tissue necrosis and organ failure.

Benign Prostatic hyperplasia (BPH) and prostate cancer are two of the most common urologic diseases that are treated with surgical intervention in aging men. An estimated 50% of men have histologic evidence of BPH by age 50 years and 75% are thought to display such evidence by age 80 years. In 40-50% of these patients, BPH becomes clinically significant. Although the incidence of uncontrolled bleeding from surgical intervention involving prostate and urethra is relatively low, it remains a significant risk that must be addressed by in hospital with a length of stay over at least two to three nights. According to statistical analysis of U.S. Department of Health and Human Service from 2005 to 2010, there was an average of 150,000 discharges from either open or transurethral procedure prostatectomy in the U.S., with direct surgery cost surpassing an average $4.5 billion annually. In these patients, the average length of hospital stay with open or transurethral prostatectomy was 3.1 and 2.4 days respectively. In the patients who had blood transfusion due to significant blood loss (4-5%) in the surgery, the average length of stay was prolonged to five or six days that cost an average $15,700 more in each case compared to the average cost ($29,300) of prostatectomy patients in 2010. The costs of the prostatectomy procedure are high because of operating-room time, surgeon time, and hospital length of stay.

TURP is considered the benchmark therapy for BPH. Partial removal (resection) of the prostate is accomplished in TURP by minimally invasive surgery through the urethra using a cystoscope (endoscope for the bladder via the urethra) and electrocautery. The thin loop electrocautery used in TURP results in less tissue necrosis than other less common minimally invasive prostatectomy procedures, however there is more intraoperative bleeding with TURP. Appropriate prostate resection and control of bleeding in TURP, like other forms of prostatectomy, are its essential challenges. The volume of the intraoperative bleeding in prostatectomy depends on the size of the prostate, the length of time to resect the prostate, and the surgeon's skill. Significant bleeding or hemorrhage after prostatectomy often causes undesirable clot retention (and resulting urinary retention) in the bladder and urethra that may prolong time in hospital, and even necessitate re-operation. In general, arterial bleeding is easily identified and controlled by electrocoagulation, but the venous bleeding common in TURP is more difficult to control. Attempts to control venous bleeding by electrocautery and irrigation may result in undesirable outcomes such as TURP syndrome. In standard of care control, venous bleeding is controlled by filling the bladder with irrigating fluid and application of an inflated transurethral balloon catheter to compress the bleeding prostatic cavity. TURP associated post-operative morbidity rate has been reported as high as 18% with an operative mortality rate of 0.3%. In older patients, the risk of blood loss related morbidity and mortality increases significantly in association with coagulation disorders and cardiovascular abnormalities. Uncontrolled bleeding during TURP is still one of the major complications of prostate resection and this often leads to converting to less desirable open surgery. Although there is significant progress in the management of BPH, the incidence of uncontrolled strong bleeding remains around 6% and blood transfusion rate to address this bleeding is 4% to 5%.

In the typical TURP, the length of hospital stay is two to four days and the patient has an inflated urinary balloon catheter in place until bleeding stops and urine becomes clear. Any significant reduction of post-op bleeding following TURP will shorten time of catheterization and hospital bed requirements. It will also decrease the incidence of urinary tract infection, catheter-related patient discomfort and related complications. Significant hematuria (blood in urine), resulting from either transurethral or open surgery, which causes hemodynamic instability and clot retention, requires immediate medical attention and medical care for hemostasis, clot clearance, blood transfusion, and coagulation evaluation. Treatment of significant hematuria through a transurethral approach is troublesome due to limited operative visual and spatial restriction. Most often the patient has to return to the operating room to perform an open bladder surgery to achieve hemostasis and remove cystic clots. A complicating factor of prostatectomy is that TURP patients are commonly anti-coagulated due to the presence of other chronic conditions such as cardiovascular disease. Although it is preferable to have these patients taken off their anti-coagulation medication such as Coumadin and Plavix before TURP surgery because of risk of bleeding, it would be preferable to be able to perform the procedure while the patient remains on their medication to reduce the possibility of stroke or myocardial infarction during the procedure. A reliable and sustainable hemostatic technique, preferably effective in the case of anti-coagulated individuals, is urgently required for the transurethral application to control significant bleeding following prostate resection.

Chitosan materials have been used in the art to address hemorrhage in varying applications and with varying degrees of success, but advances and improvements are badly needed to unlock the potential of catechol modified chitosan to provide alternative and better chitosan-based solutions for safe, reliable and effective delivery of bioactive chitosan material within the body and, particularly, within challenging in vivo biological environments.

BRIEF SUMMARY

The present invention relates to tissue adherent chitosan materials that resist dissolution. These chitosan materials comprise catechol modified chitosan and are generally referred herein to as "dressings" and such term is used to refer to solid dry materials formed from the chitosan materials of the present invention. The chitosan materials described may be suitable for and used in minimally invasive procedures.

It is to be understood that chitosan materials described herein have numerous beneficial properties arising from the chitosan material itself, and that these chitosan materials may take myriad potential solid forms. Beneficial properties characteristic of and arising from the chitosan materials described herein include, but are not limited to, the ability to tune the material by controlling the degree of substitution and level of oxidation. By tuning the material by controlling the degree of substitution and level of oxidation, the chitosan materials can resist fast degradation in difficult biological environments such as the GI tract, the urethra, the lower GI tract, internal body cavities such as the abdominal and thoracic cavities, but still be sufficiently soluble to go away in less than about seven (7) days. Additional beneficial properties of the chitosan materials are that it is also biocompatible, hemostatic, and tissue adherent. Further, the solid dry chitosan materials described herein can be delivered as a final forms or discrete dry material constructs that can displace interfering fluids due to their capillarity (presence of pores or porosity) and/or application pressure which may, in some instances, be light pressure (e.g., about 1 atm) or, in the instance of dry powder, be delivered under aerated pressure. The chitosan materials of the present invention give rise to final forms or discrete dry material constructs that can provide rapid adhesion and resists dissolution.

The dressings described herein are provided as non-limiting example final forms made using the chitosan materials of the present invention. The dressings described and exemplified herein provide examples of the conversion of catechol modified chitosan materials into various test articles, or final forms, which demonstrate the solid chitosan material solid attributes. Further dry solid chitosan final forms include, but are not limited to, freeze phase separated matrices and dressings so formed, fibers, powders, films, membranes, meshes, pledgets, etc. The present disclosure generally relates to chitosan dressing that, given its characteristics, can be applied in different physiological settings to stop bleeding. Embodiments include, among others, chitosan gastrointestinal hemostatic dressing (CGHD) and chitosan endoluminal hemostatic dressing (CEHD).

The material of the invention has the following combination of one or more, or all, properties: it (1) is able to be compacted for delivery without tearing or compromised mechanical performance; (2) is able to be applied in the presence of blood and other biological fluids at about 37° C. without significant dimensional changes in length, width and height or loss in mechanical properties; (3) is able to be delivered in the presence of biological fluids and blood; (4) is able to be delivered to a surgical site manually or by a minimally invasive delivery device; (5) is able to be expanded from a compacted state at a delivery site; (6) enables capillarity, porosity and absorbency that is able to remove hydrophilic and hydrophobic biological fluids that can interfere with adhesion; (7) is activated by wetting to adhere to mucosa, resected mucosa and resected tissue on application of uniform pressure; (8) is able to contact itself and packaging materials when dry without adherence to itself or to packaging; (9) comprises at least one tissue adherent side of the material that is able to contact itself and packaging or delivery materials when wet with urine or blood without adherence to itself or to packaging or delivery materials if wet contact is not more than 300 seconds, (10) is able to uniformly adhere to tissue and quickly promote local blood clot formation; (11) is able to be released from a delivery device to allow withdrawal of the delivery device from the surgical site; (12) is able to resist dissolution on exposure to biological fluid in the range of about pH 3.0 to about pH 8 at about 37° C. in the first 12 hours of application; (13) enables (with or without delivery device in place) ostomy connecting channels such as those in the gastrointestinal tract and the urethra to remain patent with material or residues of material present and unobstructed passage of excretions; (14) protects the injury site and provides for promotion of healing; (15) provides a controlled, slow degradation and/or dissolution from the attachment site to allow for removal without surgical assistance in less than seven days in ostomy uses; (16) the material of the invention may include one of a powder, a film, a matrix, a membrane, a thin foil, a pledget, a fiber, and a coating; (17) the tissue adherent material of the invention may include but not be limited to use as an adherent dressing, an adherent hemostatic dressing, an internal adherent fixative, an adherent patch for localized controlled release of an active agent, a suture, a staple, an orthopedic bone fixture, an occlusive suture-less patch, and a material for promotion of clotting and sealing of vascular malformations.

Although existing tools in the United States readily control a significant portion of UGIB, there remains unmet need for the low risk device of the subject invention that provides rapid control of brisk arterial bleeding. Broad application of the subject invention will enable significant reduction in morbidity and mortality in gastrointestinal bleeding treatment with concomitant reduction in associated health care expenditure.

The subject chitosan material of the invention is amenable to use in all gastrointestinal bleeding applications and may be delivered as a chitosan gastrointestinal hemostatic dressing (CGHD) by, for example, wire through a standard endoscopic working channel (≤3.2 mm diameter) or by balloon catheter delivery. The subject material of the invention will provide an opportunity to address or mitigate deficiencies with current modalities, such as clipping, thermal coagulation and injection, which necessitate pinpoint accuracy and which is challenging under impaired visibility of brisk bleeding conditions.

The present invention comprises compositions, methods of using the compositions, and methods of making the compositions.

In the preferred embodiment, the chitosan material comprises a catechol modified chitosan, wherein the CGHD dressing formed of the material is hemostatic and has a thickness that is 500 microns or less. The CGHD dressing may have a dry dressing thickness that is one of: (i) about 200 microns or less; (ii) about 100 microns or less; or (iii) about 50 microns or less. The dressing may have a density that is in the range of about 0.03 g/cm$^3$ to about 0.7 g/cm$^3$, in the range of: (i) about 0.3 g/cm$^3$ to about 0.4 g/cm$^3$; (ii) about 0.4 g/cm$^3$ to about 0.5 g/cm$^3$, or in the range of about 0.35 g/cm$^3$ to about 0.55 g/cm$^3$. The dressing may be compressed. The dressing may be square, rectangular, circular, or circular petal shaped and measurements, for each of the length and width for a square or rectangular shape, may range from about 10 mm to about 50 mm, or for a circular or circular petal shape from about 10 mm to about 50 mm in diameter. In certain embodiments, the dressing measures as one of: (i) 10 mm by 10 mm; (ii) 20 mm by 20 mm; or (iii) 25 mm by 25 mm. The dressing, when dry, has a moisture content of: (1) 15% or less by weight (w/w); (2) 8% or less by weight (w/w); or (3) 4% or less by weight (w/w). The dressing may have an adhesive side and a non-adhesive side. The dressing may have an adhesive side provided on a first layer and a non-adhesive side is provided on a second layer. The adhesive side of the dressing adheres to a tissue surface when the dressing is wet. The non-adhesive side of the dressing does not adhere to a delivery device when the dressing is wet. The dressing can adhere to a gastrointestinal mucosa in 1 minute or less. The dressing can form a quaternary ammonium cation at the chitosan glucosamine C-2 amine at a tissue site. The dressing may comprise catechol oxidized to o-quinone and cross-linked in the chitosan dressing. The chitosan dressing may have a brown coloration, including a dark brown coloration. In one embodiment, the dressing may comprise catechol that is not oxidized, and wherein the chitosan dressing has a pink coloration. The dressing may comprise freeze-dried lamella. The dressing may comprise a freeze-dried structure has a thickness of 50 microns or less. The dressing may comprise a freeze-dried structure that includes more than one freeze-dried layer. The dressing may comprise spun fibers. The dressing may comprise a porous surface. The dressing may comprise a porous surface wherein the porous surface provides one or more of: (i) and absorbent surface; and (ii) channels to redirect moisture away from a target tissue surface site. The dressing may adhere to wet tissue when in a wet condition. The dressing adherence strength may be greater than or equal to about 1 kPa. The dressing resists dissolution in water, saline solution, blood, or GI fluid at about 37° C. for at least about 6 hours. The dressing can be folded or furled without cracking or tearing. The dressing may, in an open, unfurled, or unfolded condition, have an outward facing surface area that is one of about six times greater, about five times greater, or about four times greater than the outward facing surface area of that same dressing when it is in a closed, furled, or folded condition. The dressing may have a ratio of the outward facing surface area of an open, unfurled, or unfolded condition relative to a closed, furled, or folded condition that is about 15:1, or about 14:1, or about 13:1, or about 12:1, or about 11:1, or about 10:1, or about 9:1, or about 8:1, or about 7:1, or about 6:1, or about 5:1, or about 4:1, or about 3:1, or about 2:1. The dressing can be punctured or sewn without cracking or tearing. The dressing can be cross-linked. The dressing is able to be delivered intact by a balloon device, a wire device, or an endoscopic device, wherein said device may comprise a working channel having a diameter of 3.2 mm or less, and wherein the dressing is delivered through the working channel. The dressing is able to wet and adhere intact to gastric mucosa in less than 30 seconds with application of light pressure, e.g., about 200-300 g. The dressing is able to remove hydrophilic and hydrophobic biological fluids that can interfere with adhesion. The dressing is able to stay in place intact and stop moderate to oozing bleeding ranging from between about 20 ml/min to about 150 ml/min. The dressing readily detaches from a delivery device after adherence to a target tissue site. The dressing is able to resist dissolution for at least six hours after adhering to an injury site in presence of corrosive enzymes and acid environment of about pH 3. The dressing is able to seal and protect a target tissue site for at least 12 hours. The dressing is able to achieve a controlled, slow dissolution from the attachment site over a period of time not exceeding seven (7) days. The dressing is able to be folded and unfolded. The dressing is able to be furled and unfurled. The dressing is not readily soluble in water, saline solution, blood, or GI fluid at about 37° C. for at least 12 hours following application. The dressing is not readily soluble in water, saline solution, blood, or GI fluid at about 37° C. for at least 24 hours following application. The dressing does not adhere to a delivery device. The dressing does not increase or decrease in size by more than about 25% in length and width, or more than about 50% in thickness in the presence of water, saline solution, blood, or GI fluid at about 37° C. The dressing comprises an adhesive side that interacts with an injury site, and wherein the chitosan dressing comprises a non-adhesive side that interacts with one of a delivery device or the adhesive side when the dressing is in a dry and folded or a dry and furled condition. The dressing is capable of being terminally sterilized without affecting dressing characteristics. The chitosan dressing is capable of being stored under controlled conditions over time without affecting dressing characteristics.

UGIB bleed rates, or blood flow rates, in ml/min suitable for treatment by the devices described herein may range from about 1 ml/min to about 200 ml/min. In preferred embodiments, the bleeding rates addressed by the devices range from about 1 ml/min to about 150 ml/min. A Forrest 1a UGIB is about 25 ml/min. For subjects suffering a bleed rate of much greater than a Forrest 1a, survival is unlikely unless they are already in an operating theater. UGIB bleed rate of between about 20 ml/min and 25 ml/min is considered "brisk" bleeding. Oozing bleeding is generally greater than about 1 ml/min as it is noted that low bleeding rates such as 1 ml/min typically clot and stop of their own accord unless the subject is on anticoagulation therapy or has a disorder of the clotting cascade due to reasons other than taking anticoagulation medication. For such a subject with irreversible anticoagulation medication or with a bleeding disorder, 1 ml/min oozing bleeding remains concerning and needs to be addressed such as by the device formed of the material of the invention. In some embodiments, the devices described herein are used to address UGIB bleeding rates of between about 1 ml/min and about 25 ml/min, or about 1 ml/min and about 20 ml/min, or about 1 ml/min and about 15 ml/min, or about 1 ml/min and about 10 ml/min, or about 1 ml/min and about 5 ml/min. In some embodiments, the dressing can be used for treatment of a disease, condition, disorder, trauma, or injury. For example, the use of the dressing in the treatment of a disease, condition, disorder, trauma, or injury, comprising directly adhering the dressing at an injury site upon wetting, and applying pressure to the dressing for about 30 seconds. The dressing for use in treatment of a disease, condition, disorder, trauma, or injury, may remove hydrophilic and hydrophobic biological fluids upon adherence. The dressing for use in treatment of a disease, condition, disorder, trauma, or injury, may comprise leaving the dressing in place at a target tissue site and the dressing may remain at the target tissue site for at least 24 hours. The dressing for use in treatment of a disease, condition, disorder, trauma, or injury, may be capable of slow dissolution at the target tissue site and dissolves completely without human intervention in seven days or less.

In some embodiments, the invention disclosed herein comprises methods of producing the chitosan dressing. In one embodiment, the method comprises: performing synthesis with chitosan and catechol in an aqueous reaction solution; maintaining a pH of the reaction solution at or below pH 5.5; increasing the pH of the reaction solution, and controlling oxygen exposure to the reaction solution, to provide catechol oxidation and cross-linking; and drying the reaction solution. In certain embodiments, the methods do not comprise an intermediate drying step between step. In certain embodiments, the methods comprise increasing the pH of the reaction solution from about 5.8 to about 6.2. Another embodiment of a method of producing the chitosan dressing comprises a method of producing a chitosan dressing comprising: freeze-drying a first aqueous solution comprising chitosan; freeze-drying a second aqueous solution comprising chitosan; obtaining a low-density chitosan dressing with inter-connected porous structure from each of the above steps; and compressing the low-density chitosan dressing from each of steps; and preparing a two-layer chitosan dressing from the compressed low-density chitosan dressing. In certain embodiments, the low-density chitosan dressings from each of above-mentioned freeze-drying steps are combined prior to compression. In certain embodiments, the compressing of step may occur at temperature ranging from about 20° C. to about 150° C. In certain embodiments, the dressing is dried to a moisture content of less than about 15% (w/w).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. In case of conflict, the present specification, including definitions, will control.

Other features and advantages of the invention will be apparent from the following detailed description and figures, and from the claims.

BRIEF DESCRIPTION OF THE SEVERAL VIEWS OF THE DRAWINGS

FIG. 3A is a side-on view and FIG. 3B is a plan view.

FIGS. 5A and 5B depict one image plan-view of the folded dressing all other images are cross-sectional/side on. Reference numbers, if included in the attached Figure, correspond to written text as follows: 1—Prostate; 2—Bladder; 3—Urethra mucosa; 4—Catheter body tubing; 5—Sheath; 6—Furled CEHD on delivery balloon of delivery catheter; 7a—conical folded CEHD with attachment point (14) proximal (left of) to delivery balloon catheter; 7b—conical folded CEHD with attachment point (14) distal (right of) to delivery balloon catheter; 7c—plan view of CEHD conical folded CEHD with attachment point (14) distal. Note that there may be two dressings on one balloon with distal and proximal attachments or just one dressing with proximal attachment only. An alternate delivery is with the CEHD furled as a cylinder around the delivery balloon however this is not drawn; 8—Delivery balloon (there are drawings of single balloon catheter—less preferred—and double balloon—preferred). In the double balloon catheter the delivery balloon is also the proximal balloon; 9—Cutting for creating the circular window attachment point towards the apex of the conically folded dressing (9a proximal; 9b distal); 10—Overlaying edges of two faces of conical dressings facing each other; 11—Apices of conical folded CEHD's (11a proximal; 11b distal); 12—Irrigation ports (12a proximal; 12b distal); 14—Conical folded CEHD apex attachment point to balloon catheter with body of CEHD folded over and furled around delivery balloon. A simple double sided pressure adhesive works well to attach the CEHD apex to the catheter. This attachment assists sliding the close-fitting sheath over the folded and furled CEHD without the CEHD being caught by the sheath in its application; 15—Distal or placement/positioning balloon in a double balloon delivery catheter. This is preferred over the single balloon catheter as the distal balloon can be used to rupture and initiate removal of the sheath and it provides ideal ability to locate the delivery balloon. The distal balloon may be used to achieve apposition of the CEHD against the bladder neck in the case of anastomoses and bladder neck injury; and 16—Ports for the balloon catheter (3 ports are typical in a 2 balloon catheter however a multi-lumen catheter with 2 balloons may have more). There is typically one port for each balloon and at least one point for irrigation and drainage. The ports typically connect to standard syringe luer connectors.

FIGS. 12A-12G show tables of various parameters for batches used to prepare chitosan dressings.

FIGS. 13A-13E show a table of various chitosan dressing preparations, including formulations, and dissolution, foldability, burst testing, ex-vivo, accelerated stability, and in vivo characteristics.

FIGS. 16A-16C depict a table showing dissolution testing results.

FIGS. 17A-17C depict a table showing formulation approaches, hydrophilic polymers, and % w/w of solution hydrophilic polymer components.

DETAILED DESCRIPTION

Figure 1A:
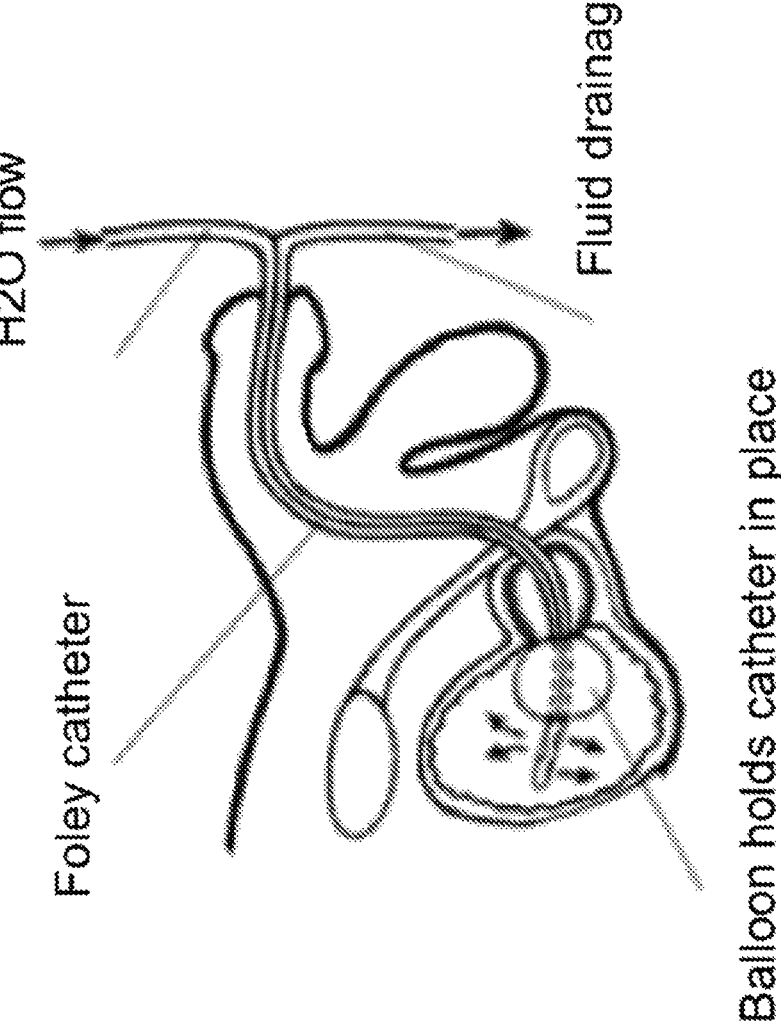
FIGS. 1A, 1B, 1C, 1D, 1E, 1F, and 1G depict the introduction, placement, and use of dressings formed from the material of the present invention.
Figure 1B:
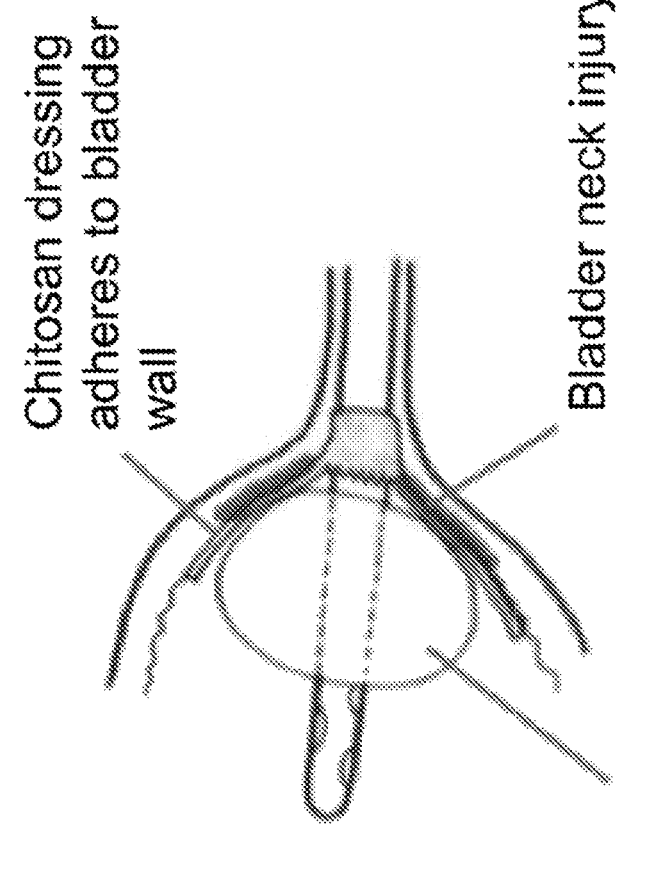
Figure 1C:
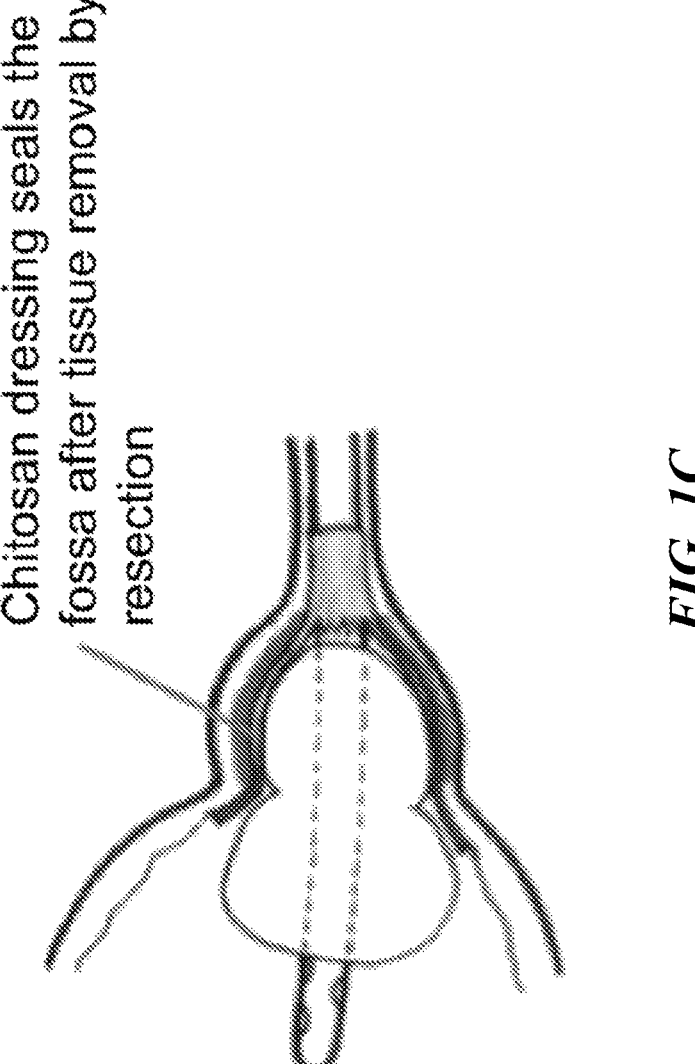
Figure 1D:
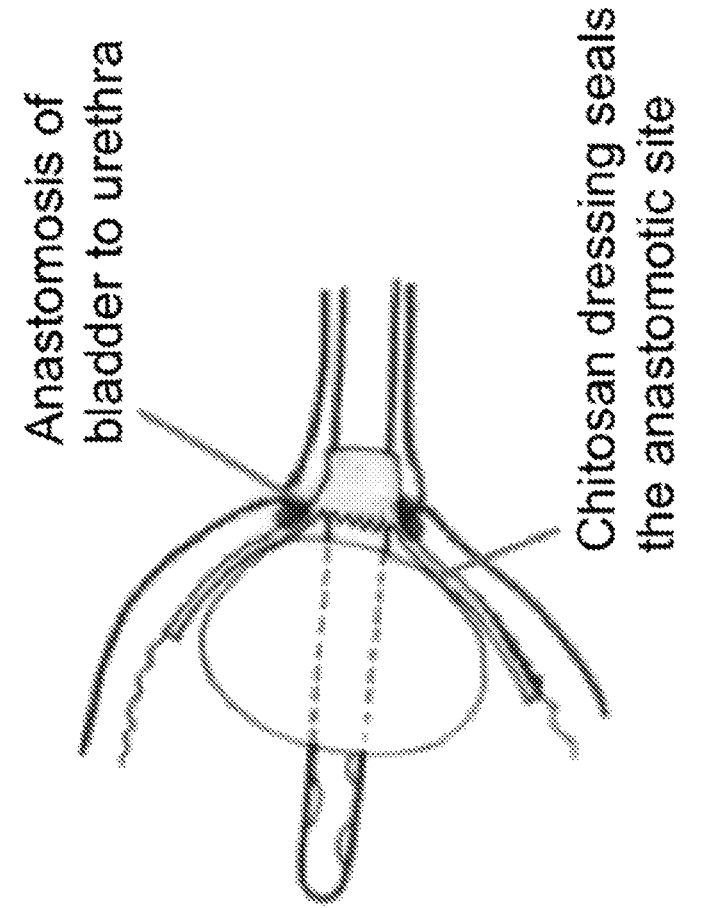
Figure 1E:
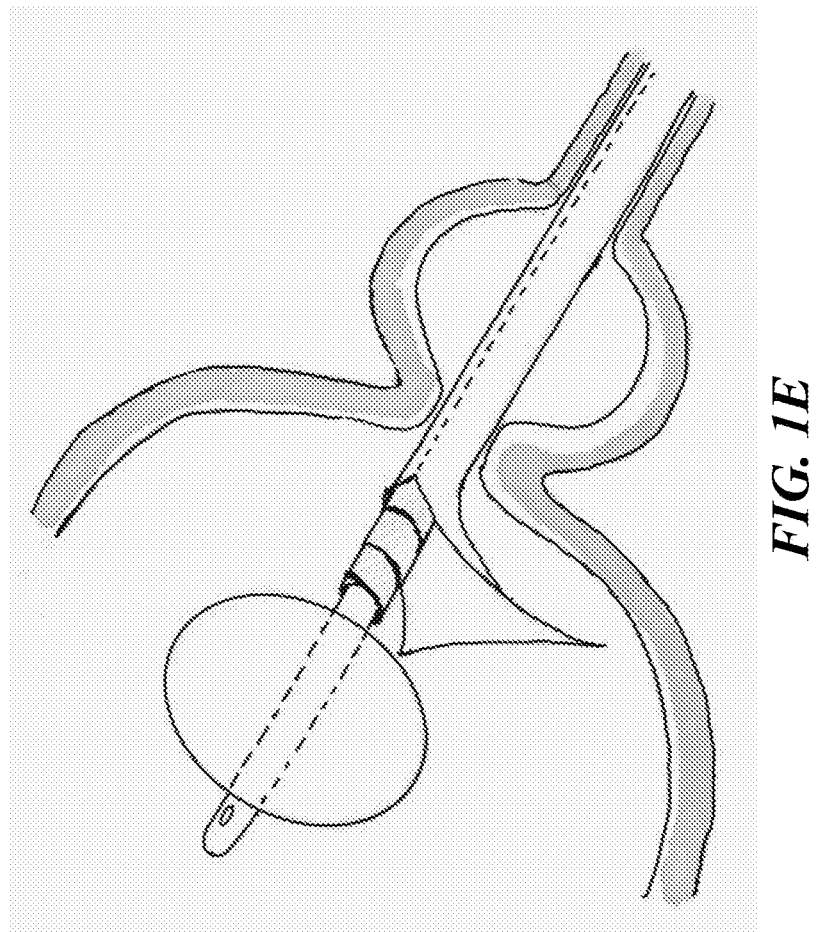
Figure 1F:
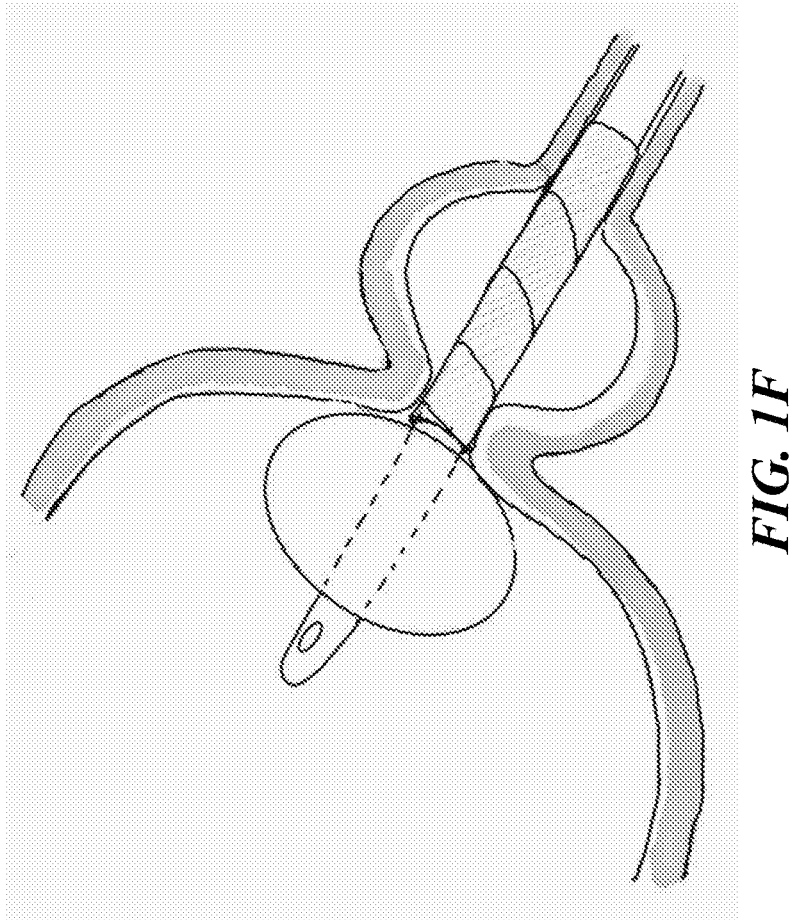
Figure 1G:
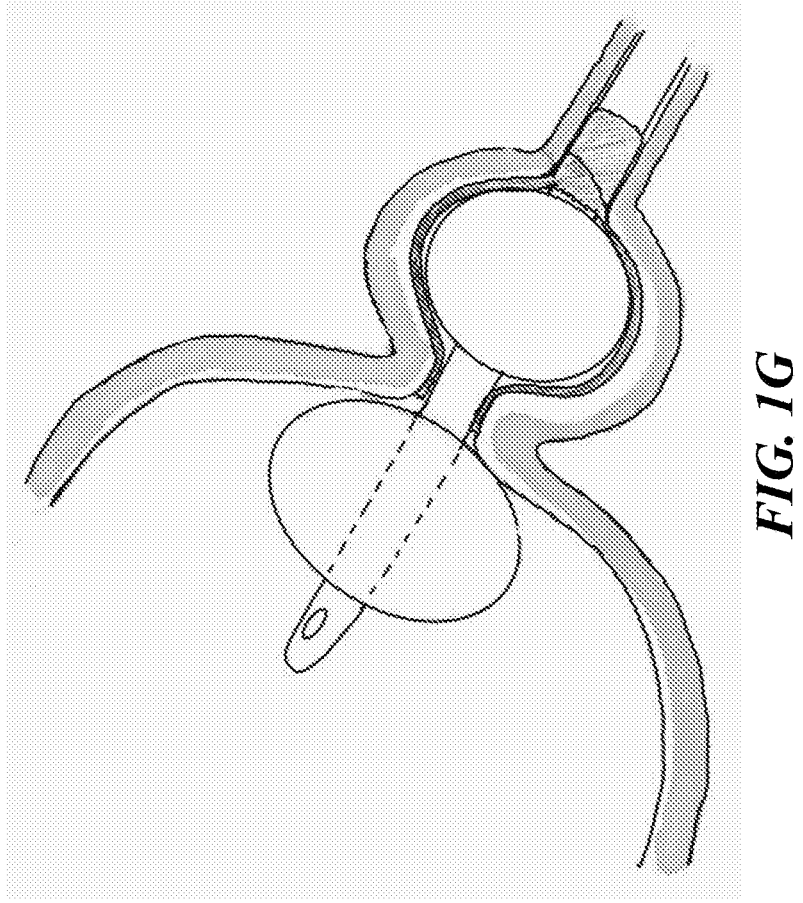

In one aspect, the present invention relates to a biocompatible, foldable, thin profile, chitosan-based dressing comprising catechol modified chitosan and characterized by one or more, or all, of the following features, such that it is: (1) able to be delivered intact by balloon or through endoscopic device; (2) is able to wet and adhere intact to gastric mucosa in under 30 seconds with application of light pressure; (3) has capillarity, porosity and absorbency that is able to remove hydrophilic and hydrophobic biological fluids that can interfere with adhesion; (4) is able to stay in place intact and stops moderate to oozing bleeding, e.g., a bleeding rate of between about 20 ml/min to about 100 ml/min, or greater; (5) is able to be released from the delivery device to allow withdrawal of the delivery device from the GI environment; (6) is able to resist detrimental rapid breakdown (<6 hours) in the corrosive enzymes and acidity (≥pH 3) of the GI environment; (7) is able to protect the gastrointestinal injury site for preferably up to 12 hours, more preferably up to 24 hours and most preferably up to 96 hours to assist with its subsequent acute healing and closure; and (8) is able to achieve a controlled, slow dissolution from the attachment site to allow for unassisted complete removal in less than seven days with the dissolved residue passing safely through the alimentary tract.

The present invention addresses rapid bleeding control in transurethral prostatectomy, open prostatectomy, bladder resection using a foldable, thin (thickness 5 about 500 microns), tissue adherent, chitosan-based, hemostatic dressing. The dressing formed from the material of the invention has one or more, or all, of the following features, such that it is: (1) able to be folded or furled and unfolded and unfurled without tearing or compromised mechanical performance; (2) able to be applied in the presence of blood and urine at about 37° C. without significant dimensional changes in length, width and height or loss in mechanical properties; (3) able to be delivered in the presence of urine and blood; (4) able to be delivered to injury site by a transluminal or transurethral delivery device; (5) able to be unfolded or unfurled at delivery site; (6) characterized by capillarity, porosity and absorbency that is able to remove hydrophilic and hydrophobic biological fluids that can interfere with adhesion; (7) activated by wetting to adhere to bladder mucosa, resected bladder mucosa and resected prostate on application of uniform pressure; (8) able to contact itself and packaging materials when dry without adherence to itself or to packaging; (9) inclusive of a tissue adherent side of dressing that is able to contact itself and packaging or delivery materials when wet with urine or blood without adherence to itself or to packaging or delivery materials if wet contact is not more than about 300 seconds, (10) able to uniformly adhere to tissue and quickly stanch moderate to oozing bleeding at pressure ≤about 50 mmHg or, for example, a bleeding rate of between about 20 ml/min to about 100 ml/min or greater, providing opportunity to allow TURP to be performed as an outpatient procedure; (11) able to be released from the delivery device to allow withdrawal of the delivery device from the urethra; (12) able to resist dissolution on exposure to urine at about pH 4.5 to about pH 8 at about 37° C. in about the first 12 hours of application; (13) enables (with or without delivery device in place) the urethra to remain patent with dressing or residues of dressing present and allows unobstructed passage of urine; (14) protects the injury site and provides for promotion of healing; (15) provides a controlled, slow degradation and/or dissolution from the attachment site (bladder neck, prostate, and/or urethra) to allow for removal without surgical assistance in less than about 7 days.

The current invention provides: (1) an ability to rapidly control hemorrhage in prostatectomy using a noninvasive procedure; (2) an ability to control bleeding in anti-coagulated patients; (3) significantly reduced patient pain and discomfort by control of bleeding without need for prolonged catheterization; (4) significantly reduced hospital length of stay; (5) significantly reduced healthcare cost; (6) significantly reduced rate of morbidity; and (7) trending outcomes to a reduced rate of mortality.

As used herein, bladder mucosa is broadly defined to include any exposed tissue surface in the bladder including any tissue surface exposed by way of an operation (e.g., surgical operation). Bladder mucosa therefore includes bladder mucosa naturally present in the bladder, resected bladder mucosa, and resected prostate, etc.

Chitosan endoluminal hemostatic dressing (CEHD), as used herein, refers to a chitosan dressing that is hemostatic, and can be used in an endoluminal area e.g., inside bladder. CEHD is not limited by the position of its application and include chitosan dressing that is applied at any location inside a human body, including but not limited to bladder mucosa.

Bleed rates, or blood flow rates, in ml/min suitable for treatment by the devices described herein may range from about 1 ml/min to about 200 ml/min. In preferred embodiments, the bleeding rates addressed by the devices range from about 1 ml/min to about 150 ml/min. A bleed rate of between about 20 ml/min and 25 ml/min is considered "brisk" bleeding. Oozing bleeding is generally greater than about 1 ml/min as it is noted that low bleeding rates such as 1 ml/min typically clot and stop of their own accord unless the subject is on anticoagulation therapy or has a disorder of the clotting cascade due to reasons other than taking anticoagulation medication. For such a subject with irreversible anticoagulation medication or with a bleeding disorder, 1 ml/min oozing bleeding remains concerning and needs to be addressed such as by the device formed from the material of the invention. In some embodiments, the devices described herein are used to address TURP bleeding rates of between about 1 ml/min and about 25 ml/min, or about 1 ml/min and about 20 ml/min, or about 1 ml/min and about 15 ml/min, or about 1 ml/min and about 10 ml/min, or about 1 ml/min and about 5 ml/min.

A TURP delivery device may include any device that is used in a TURP procedure or any device used in connected with a TURP procedure.

Chitosan Dressing

Chitosan dressings may refer to compositions that include varying amounts of chitosan. The general contents, general chemical compositions and different forms of a chitosan dressing are described, for example, in U.S. Pat. Nos. 7,820,872, 7,482,503, 7,371,403, 8,313,474, 7,897,832, 9,004,918, 8,920,514, 9,204,957, 8,741,335, 8,269,058, 9,205,170, and 10086105. Such chitosan dressings, due to their chemical and physical properties as described previously, have been used to stop bleeding.

The chitosan used preferably comprises the non-mammalian material poly[β-(1→4)-2-amino-2-deoxy-D-glucopyranose. The chitosan can be processed in conventional ways from chitin obtained, for example, from animal crustacean shells such as shrimp. Chitosan may be biocompatible and biodegradable within the body, and is capable of being broken down into glucosamine, a benign material. The catechol-modified chitosan used herein may include reference to catechol-added chitosan.

A chitosan dressing can be dry or wet. A chitosan dressing is "dry" if the moisture content in the chitosan dressing is less than about 15% by weight, preferably about 10% by weight, and more preferably about 5% by weight. A chitosan dressing is "wet" when the chitosan dressing has come in contact with a source of water, including water in a physiological environments and biological fluids, or in an aqueous solution. For example, a chitosan dressing becomes wet when the chitosan dressing, as described in this disclosure, comes in contact with gastrointestinal tract fluid, urine, or blood or a tissue surface of gastrointestinal tract or bladder (bladder mucosa or GI mucosa). The chitosan dressing, remaining substantially in a solid form absorbs, displaces, redirects or channels water/moisture in the physiological environment of gastrointestinal tract or bladder mucosa in amounts sufficient to permit adhesion of the chitosan dressing to the tissue surface. The adhered chitosan dressing can be used to seal wound surfaces and slow or stop further bleeding.

In a preferred embodiment, the chitosan gastrointestinal hemostatic dressing (CGHD) or chitosan endoluminal hemostatic dressing (CEHD) formed from the material of the invention contains preferably greater than or equal to 25% by weight chitosan; more preferably greater than or equal to 50% by weight chitosan and most preferably greater than or equal to 75% by weight chitosan. Chitosan is a generic term used to describe linear polysaccharides that are composed of glucosamine and N-acetyl glucosamine residues joined by β-(1-4) glycosidic linkages (typically the number of glucosamines ≥N-acetyl glucosamines) and whose composition is soluble in dilute aqueous acid (Roberts 1991). The chitosan family encompasses poly-β-(1-4)-N-acetyl-glucosamine and poly-β-(1-4)-N-glucosamine with the acetyl residue fraction and its motif decoration (either random or block) affecting chitosan chemistry. The C-2 amino group on the glucosamine ring in chitosan allows for protonation, and hence solubilization of chitosan in water (pKa≈6.5) (Roberts 1991). Other hydrophilic polymers such as, for example, guar, pectin, starch and polyacrylic acid may be used.

In a preferred embodiment of CGHD, the dressing formed from the material of the invention is polymeric, thin (preferably dry dressing thickness of about ≤500 microns, more preferably thickness of about ≤200 microns, most preferably thickness of about ≤100 microns), flexible, porous, dry, biocompatible, tissue adherent and hemostatic.

In a preferred embodiment of CEHD, the dressing formed from the material of the invention is polymeric, thin (preferably dry dressing thickness of about ≤500 microns, more preferably thickness of about ≤200 microns or about ≤100 microns, most preferably thickness of about ≤150 microns), flexible, porous, dry, biocompatible, tissue adherent and hemostatic.

In some embodiments, the dressings are about 100 microns in thickness, and may comprise a bilayer dressing of two about 70 micron layers (one layer that is adhesive and resistant to dissolution and one layer that is straight chitosan) with sum thickness nearer 150 microns on delivery.

The dressings are not limited in shape, however square, rectangular, circular, or circular petal shaped dressings are preferred. In one embodiment, a maximum size could be up to about 50 mm×50 mm square or 50 mm in diameter. In another embodiment, dressing size could be about 45 mm×45 mm square or 45 mm in diameter, 40 mm×40 mm square or 40 mm in diameter, 35 mm×35 mm square or 35 mm in diameter, 30 mm×30 mm square or 30 mm in diameter, 25 mm×25 mm square or 25 mm in diameter, 15 mm×15 mm square or 15 mm in diameter, 10 mm×10 mm square or 10 mm in diameter, etc. In still another embodiment, each of the length and width may range from about 10 mm to about 50 mm, or from about 10 mm to about 50 mm in diameter. As dressings become larger in size they become increasingly subject to delivery limitations in confined cavities.

In another preferred embodiment, the dressing is delivered by balloon catheter, and the dressing has a diameter size of about around 5 cm, or 7 cm maximum. The balloon catheter is preferably passed through a central small hole (about same diameter as catheter balloon which is generally about 4 mm to about 7 mm diameter, or the hole can be larger, e.g., up to 12 mm) in the dressing and the dressing (dressing 30 mm to 70 mm diameter) is adhered to the catheter tubing (same diameter as catheter) opposite the balloon by small dressing tabs either side of the hole. In some embodiments, the surface area change in the dressing from a folded, furled, or compacted condition is about ⅛ of the surface area when the dressing is in an unfolding, unfurled, or uncompacted condition. Dressings described herein may provide a large dressing surface area in an open, unfurled, or unfolded condition. Alternatively, dressings described herein may provide a small dressing surface are in a closed, furled, or folded condition. The ability of the dressings to be folded, furled, or closed allows them to be more compact and protected for delivery and reduces the likelihood that the dressing surface is prematurely wetted prior to delivery to a target tissue treatment site.

In a preferred embodiment of CGHD, the dressing is about 50 microns thick, is about 2.5 cm in diameter, and will have an open, unfurled, or unfolded outward facing surface area of about 9.856 cm². Inside the delivery device sheath (wall thickness of a typical fluorinated ethylene propylene (FEP) delivery tube is about 150 microns), a closed, furled, or folded dressing will have an outward-facing cylindrical surface area (in a 1.25 cm long cylinder) of about 2.07 cm² inside a 0.45 cm diameter gastroscope channel, or about 1.56 cm² inside a 0.32 cm diameter gastroscope channel; or about 1.41 cm² inside a 0.28 cm diameter gastroscope channel. Thus, in one example, a dressing of the present invention may, in an open, unfurled, or unfolded condition, have an outward facing surface area that is about six (6) times greater, about five (5) times greater, or about four (4) times greater than the outward facing surface area of that same dressing when it is in a closed, furled, or folded condition. In some embodiments, the ratio of the outward facing surface area of an open, unfurled, or unfolded to a closed, furled, or folded dressing is about 15:1, or about 14:1, or about 13:1, or about 12:1, or about 11:1, or about 10:1, or about 9:1, or about 8:1, or about 7:1, or about 6:1, or about 5:1, or about 4:1, or about 3:1, or about 2:1.

In some CGHD embodiments, the most common gastroscope channel is 0.28 cm diameter (2.8 mm) and hence this is the most preferred size for the dressing delivery. Alternatively, a more preferred size is 0.32 cm diameter, which is a standard gastroscope channel diameter but less common than the 0.28 cm channel. Another preferred gastroscope channel diameter size is between 0.45 cm and 0.32 cm which is more a custom gastroscope channel size and, thus, less common than the 0.32 or the 0.28 cm gastroscope channel diameter size.

In a preferred embodiment of CEHD, the dressing is about 100 microns thick, is about 5.0 cm in diameter, and will have an open, unfurled, or unfolded outward facing surface area of about 38.66 cm². On the balloon delivery device, a closed, furled, or folded dressing will have an outward-facing cylindrical surface area (in a 2.5 cm long cylinder) of about 5.09 cm² on a 7 mm diameter catheter balloon, or about 14.0 cm² open and 1.85 cm² closed on a 4 mm diameter catheter balloon with a 3.0 cm diameter dressing. Thus, in one example, a dressing of the present invention may, in an open, unfurled, or unfolded condition, have an outward facing surface area that is about eight (8) times greater than the outward facing surface area of that same dressing when it is in a closed, furled, or folded condition. In some embodiments, the ratio of the outward facing surface area of an open, unfurled, or unfolded to a closed, furled, or folded dressing is about 15:1, or about 14:1, or about 13:1, or about 12:1, or about 11:1, or about 10:1, or about 9:1, or about 8:1, or about 7:1, or about 6:1, or about 5:1, or about 4:1, or about 3:1, or about 2:1.

In some CEHD embodiments, the most common catheter balloon used with a delivery device in TURP is 0.4 cm diameter (4.0 mm) and hence this is the most preferred size for the dressing delivery. Alternatively, a more preferred size is 0.5 cm diameter, which is a standard catheter diameter for a TURP delivery device but less common than the 0.4 cm catheter. Another preferred catheter diameter size of a TURP delivery device is between 0.5 cm and 0.7 cm which is more a custom channel size and, thus, less common than the 0.4 or the 0.5 cm catheter diameter size.

A dressing as described herein is able to be folded and unfolded, is not readily soluble in blood or body fluid, such as GI fluids or urine, at about 37° C. within, preferably, the first 6 hours of application, more preferably the first 12 hours of application, and most preferably the first 24 hours of application, and degrades and/or dissolves fully in contact with GI fluids or bladder fluids at about 37° C. within about 7 days.

A dressing as described herein will not adhere to the delivery device, and does not swell or shrink appreciably, i.e., it does not increase or decrease in size by more than about 25% in length and width, or more than about 50% in thickness, in the presence of blood and body fluids (GI fluids or urine or bladder fluids or mixture thereof) at about 37° C.

In a preferred embodiment, the dressing may be terminally sterilized without affecting dressing characteristics. When it is stored under controlled conditions in its packaging at room temperature of about 21° C. to about 25° C., its tissue adhesion properties, mechanical properties, dissolution properties in GI or bladder fluids, swelling properties, and hemostatic properties are stable and do not change appreciably over time (e.g., about ≤2 years).

A preferred embodiment, the dressing has a tissue adhesive side and a non-adhesive side. In this embodiment, the non-adhesive side may provide a surface that when wet readily slides away from itself and from any applicator or delivery device surface that is applying pressure against the dressing inside a lumen, and/or in the gastrointestinal tract or bladder.

A preferred embodiment of the dressing is that it is formed of a substantially dry chitosan composition with a water content of about ≤15%, or about ≤8%. The dry chitosan composition is preferably formed using phase separation and drying of an aqueous solution of chitosan and water. The dry chitosan dressing is preferably prepared in sheet form which may be cut to size.

Preferred embodiments of the biocompatible, bio-dissolvable, tissue adherent chitosan dressing are able to resist dissolution in gastrointestinal (GI) fluid and blood at about 37° C. for at least about 6 hours is tissue adherent and includes materials and material structures that promote resistance to rapid dissolution and degradation in the low pH and strongly enzymatic digestive fluid of the upper gastrointestinal tract. This is a significant advantage of the chitosan dressings disclosed herein because the upper gastrointestinal digestive tract has evolved to rapidly digest most organic materials including chitosan, cellulose and starch.

Preferred embodiments of the biocompatible, bio-dissolvable, tissue adherent chitosan dressing are able to resist dissolution in bladder fluid and blood at about 37° C. for at least about 6 hours is tissue adherent and includes materials and material structures that promote resistance to rapid dissolution and degradation in urine of the bladder. This is a significant advantage of the chitosan dressings disclosed herein.

Chitosan dressings provided herein can be applied to a mucus surface, e.g., in GI or the bladder by light pressure, or pressure of up to hundreds of KPa. Light pressure applied to the dressing on a tissue surface as used herein indicates a pressure that attaches and keeps a chitosan dressing in contact with an injury site without significant deflection or movement of the tissue so as to allow the chitosan dressing, through its compositional structures and characteristics, to interact to promote adherence with the injury site to stop bleeding. In some embodiments, a light pressure is a pressure at about most preferably 10 kPa or less, more preferably 25 kPa or less, or preferably 50 kPa or less (note 100 g/cm2=9.8 kPa). Typically there is significant deflection on application of load above 100 kPa to soft tissue such as the stomach making application of pressure without a supportive opposite pressure impossible. An exploration of the elastic modulus of the human stomach is provided in Saraf et al. 2007. Saraf, H. et al., *Mechanical properties of soft human tissues under dynamic loading*, J. OF BIOMECHANICS, 40(9), pp. 1960-1967 (2007).

Production of Chitosan Dressing

The chitosan dressings of the present invention may be generated using various methods and processes. In some embodiments, the chitosan dressing may be formed by freeze phase separation and drying. In an alternate embodiment, the dressing is formed by addition of a foaming agent to provide a low density foam before freezing followed by drying. Freeze phase separation followed by removal of frozen solvent by sublimation is called freeze drying. Freeze phase separation is a process of solidification from dilute solution whereby removal of heat and resultant lowering of temperature through a container or mold surface holding the dilute solution results in a localized solid crystal nucleation of pure solvent and subsequent propagation and growth of pure solvent crystal. A result of the pure solvent crystal growth in a dilute solution is that solute diffuses away from the growing crystal front to solidify at the interstices between the growing crystal. Freeze phase separation of dilute polymer aqueous solutions results in alternate layers of thin polymer lamella between thicker layers of ice. Removal of the ice by methods which do not disrupt the polymer lamella results in a low-density polymer dressing with inter-connected porous structure. For example, in one embodiment, low-density polymer dressings may have an initial dressing density from about 0.005 g/cm³ to about 0.05 g/cm³.

In an alternate embodiment, the freeze phase separated dressing is formed by freezing of a foamed dilute solution followed by drying. In an alternate embodiment, the dressing is formed by non-woven fiber spinning processes, such as centrifugal spinning, electrospinning or solvent fiber extrusion into a coagulation bath. In yet another alternate embodiment, the dry dressing formed from the material of the invention may be formed from a woven fiber process. In yet another alternate embodiment, the dry dressing formed from the material of the invention may be formed by phase inversion and precipitation with a non-solvent (as is typically used to produce dialysis and filter membranes). In still another alternate embodiment, the dressing formed from the material of the invention may be formed from an additive 3D printing process.

In a preferred embodiment formed from the material of the invention, the dressing preparation process may include a compression process that changes the initial dressing density from an initial preferred range of about 0.005 g/cm³ to about 0.05 g/cm³ to a final preferred range of about 0.03 g/cm³ to about 0.7 g/cm³; however, ranges of about 0.08 g/cm³ to about 1.2 g/cm³ are also contemplated. It is noted that a density of about 1.5 g/cm³ is the density of void-free chitosan dressings. The compression process may include application of temperature in the range of about 20° C. to about 150° C. To avoid substantial dressing swelling of the dry compressed dressing on contact with biological fluid, the temperature of the compression is preferably applied by a method that may include but not be limited to convection, conduction and radiation, and the temperature of the compressed dressing should preferably be maintained at least about 80° C. for at least about 15 seconds.

Heat during compression is a tool that allows plasticization and molding of the chitosan without cracking or tearing of the chitosan (non-destructive molding). The first glass transition temperature (Tg) of pure dry chitosan is near 80° C. which if processed near in the case of pure dry chitosan will allow ready non-destructive molding of the chitosan as well as some crystalline annealing of its structure. It is possible to lower the Tg by application of plasticizers such as water or glycerol to the chitosan and hence provide a similar level of non-destructive molding at lower temperature. Here, it is noted that chitosan can be molded non-destructively in the range 20° C. to 150° C. Outside of this range it would still be possible to non-destructively mold the chitosan but much more difficult. Above 150° C. the chitosan begins to thermally degrade while below 20° C., the addition of plasticizers may lead to undesirable loss of chitosan crystallinity which provides for dissolution resistance and resistance to degradative processes such as occur in sterilization.

Preferably, the compression prevents substantial swelling of the dry compressed dressing on contact with biological fluid and is performed with moisture content of the dry dressing during the compression at about ≤15% w/w. The compression may be applied through twin or multi-roller compression and/or uniaxially between adjacent platens.

The compression may be against a uniform flat or curved surface to provide a smooth finish to the compressed dressing.

Alternatively, the compression may be applied against an etched, machined, ablated or other type of surface treatment that imparts a depleted or added surface texture. The surface texture may be a random or it may be a regular repeated pattern. The pattern of the surface may assist in folding and unfolding or furling and unfurling the dressing and may provide for hinge-like properties in the dressing. Such texture may be used as an adjunct to quickly lock the dressing in place and stop it moving when applied. Movement of the surface of the dressing while positioned against the target tissue surface can cause filming and hence closure of the open surface structure which can lead to loss ability to remove anti-adhesive biological fluid at the surface and hence loss of ability to adhere the dressing to the surface. The timescale of the changes occurring at the dressing surface is very important such that surface uptake of fluid with significant surface dressing channel closure is highly undesirable. A good way to avoid such movement is to physically fix the dressing in place as soon as it contacts the tissue surface.

Prior to the present invention, thin solid chitosan dressings were generally rigid, not flexible enough to be bent or folded or furled without breaking, fracturing, or otherwise losing their intact shape or becoming otherwise unsuitable for use. Chitosan dressings provided herein, due to their compositional structures and characteristics, can be folded and unfolded along a folding axis while still being intact and suitable for use in stopping bleeding. Interestingly, and contrary to expectation, it has been found that chitosan dressings described herein, when folded, become less resistant to tearing or breakage along their folded seams. In some embodiments, the chitosan dressing provided herein, due to its compositional structures and characteristics, can be furled without losing its compositional structures and characteristics and still being intact and able to stop bleeding.

In some embodiments of CGHD, the chitosan dressing provided herein, due to its compositional structures and characteristics, can be furled without losing its compositional structures and characteristics and still being intact and able to stop bleeding. In some embodiments, the chitosan dressing provided herein, therefore, is able to be delivered through a narrow working channel while still maintaining their compositional structures and characteristics intact. Exemplary diameters of a narrow working channel through which the chitosan dressing provided herein can be delivered include a diameter of about 3.2 mm or less, and including, but not limited to, 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, and 3.2 mm.

In some embodiments of CEHD, the chitosan dressing provided herein, due to its compositional structures and characteristics, can be furled without losing its compositional structures and characteristics and still being intact and able to stop bleeding. In some embodiments, the chitosan dressing provided herein, therefore, is able to be delivered by balloon catheter along the urethra while still maintaining their compositional structures and characteristics intact. Exemplary diameters of the balloon catheter supporting the chitosan dressing can include a diameter of about 12 mm or less, and including, but not limited to, 3 mm, 3.5 mm, 4.0 mm, 4.5 mm, 5.0 mm, 5.5 mm, 6.0 mm, 6.5 mm, 7.0 mm, 7.5 mm, 8.0 mm, 8.5 mm, 9.0 mm, 9.5 mm, 10.0 mm, 10.5 mm, 11.0 mm, 11.5 mm, and 12.0 mm.

Catechol Modified Chitosan; and its Production

The chitosan dressings described herein relate to chitosan dressings comprising catechol modified chitosan and/or hydrophilic polymers. Other aspects of chitosan dressing comprising catechol modified chitosan are described in more details below.

Preferred embodiments of the CGHD or CEHD of the disclosure include compositions with catechol modified chitosan and/or, optionally, other hydrophilic polymers. Preferably the catechol modified chitosan in the dressing provides prolonged adherence to wetted tissue with tissue adherence ≥about 1 kPa resisting dissolution in water, saline solution, blood and/or GI or bladder fluid at about 37° C. for ≥about 6 hours. Preferably the catechol modified chitosan is formed by N-acylation of the C-2 amine on the chitosan glucosamine by 3,4-dihydroxyhydrocinnamic acid (alternatively named 3-(3,4-Dihydroxyphenyl)propionic acid, Hydrocaffeic acid)). Alternatively, the chitosan N-acylation to produce a catechol modified chitosan may include but not be limited to a modification with one of a 3,4-Dihydroxycinnamic acid (caffeic acid); a trans-3,4-Dihydroxycinnamic acid (trans-caffeic acid); and a 3,4-Dihydroxyphenylacetic acid (DOPAC, Homoprotocatechuic acid).

The presence of catechol in the composition provides for some poly-conjugated structure as the catechol is oxidized to o-quinone. This causes visible difference between the unmodified chitosan and catechol modified chitosan compositions, which may be off-white or pink to dark brown in color, respectively. It is noted that the catechol modified chitosan compositions go from pink to brown when oxidation occurs in the catechol.

Pink coloration in the catechol modified chitosan, signifying substantial absence of crosslinking, is provided in the aqueous synthesis by maintaining pH reaction solution at or below pH 5.5. The pink coloration may also be provided in the aqueous synthesis by performing the modification and subsequent processing steps substantially in the absence of oxygen such as by using aqueous systems purged with an inert gas which may include but not be limited to argon or nitrogen. Although the pink coloration is not desirable in the final solution or catechol modified product, it may be desirable in intermediate handling stages (such as immediately after chitosan derivatization with catechol and/or dialysis and/or washing of the subsequent catechol chitosan solution to remove residual unreacted material) because it allows for stable dry product polymer storage and dry product weight determination with subsequent ability to substantially re-dissolve the pure dry catechol modified product in water to a desired dry weight at a later time. This water-soluble chitosan catechol material is then subsequently oxidized and crosslinked (with brown coloration). However catechol modified chitosan which is dried before oxidation is not suitable for use in the chitosan dressing formed from the material of the invention because dressings including such treated catechol modified chitosan are not readily redissolved and the final solution includes an undesirable mass fraction (>5% w/w) of insoluble particulate (>10 microns in diameter). Additionally catechol chitosan prepared after an intermediate freeze drying stage is more prone to early dissolution in gastrointestinal fluid or bladder. It is noted that too much crosslinking in TURP (i.e., brown color) is less desirable as this makes the dissolution in urine take longer, for example, longer than 168 hours when the target complete dissolution is between about 72 hours to about 168 hours).

In a preferred embodiment, the catechol modified chitosan is not removed from solution by an intermediate drying step to allow for storage but rather it is kept in aqueous solution and oxidized in aqueous solution by exposure to higher than about pH 5.5 in the presence of atmospheric oxygen. Preferred pH control is achieved by adjustment of partial pressure of aqueous dissolved carbon dioxide (increased partial pressure reduces pH while decreased partial pressure increases pH to nearer pH 7). An alternative preferred means of pH control is by incremental addition of a strong acid to lower pH and a strong base to raise pH. Examples of strong acids may include, but are not limited to, hydrochloric acid, sulphuric acid and nitric acid. Examples of strong bases may include but not be limited to sodium hydroxide and potassium hydroxide. Subsequent drying of this aqueous water-soluble oxidized catechol modified chitosan results in a preferred level of crosslinking of the catechol chitosan with good resistance to dissolution and degradation in the upper gastrointestinal tract and in bladder. The catechol chitosan solution may be diluted by addition of water or concentrated by water removal. The water may be removed by the techniques including, but not limited to, ultrafiltration, reverse dialysis and centrifugation. The solid fraction of the solution may be determined by sampling a known volume from the solution and performing analyses including but not limited to gravimetry, Fourier transform infrared spectroscopy, ultraviolet-visible spectroscopy, refractometry, and pycnometry.

Figure 15:
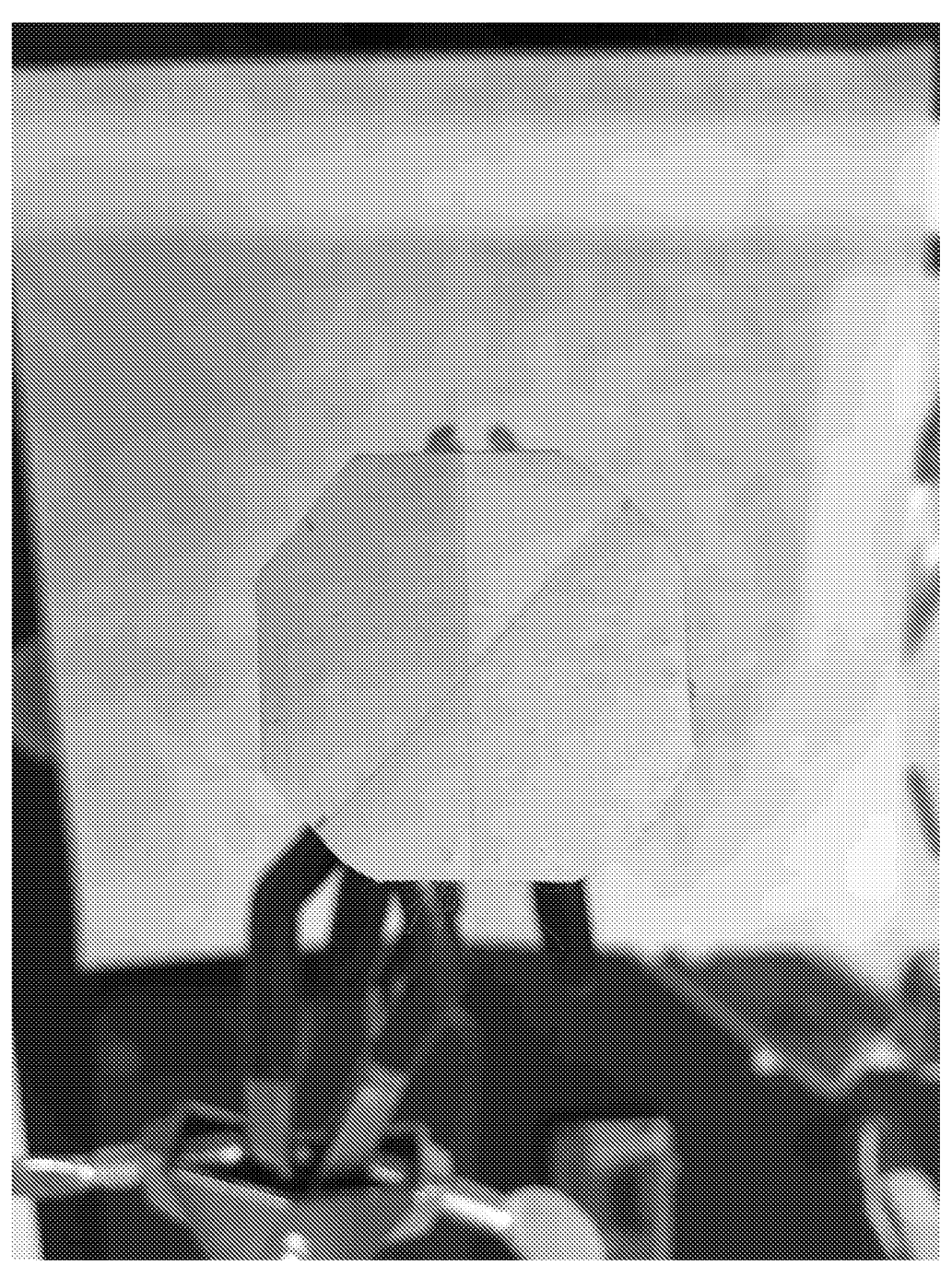
FIG. 15 depicts a catechol modified chitosan dressing that has been folded and unfolded, while remaining intact, with visible fold axis (crease).
Figure 18:
FIG. 18 depicts a gastroscope digital image of the modified catechol chitosan dressing of the invention intimately adhered to stomach mucosa, demonstrating slight swelling in the stomach environment, and effectively controlling upper gastrointestinal hemorrhage (Forrest 1a) of a lacerated gastroepiploic artery inside the stomach of a heparinized (ACT ≥250 s) swine 3 hours after application of the dressing to the arterial injury.
Figure 19:
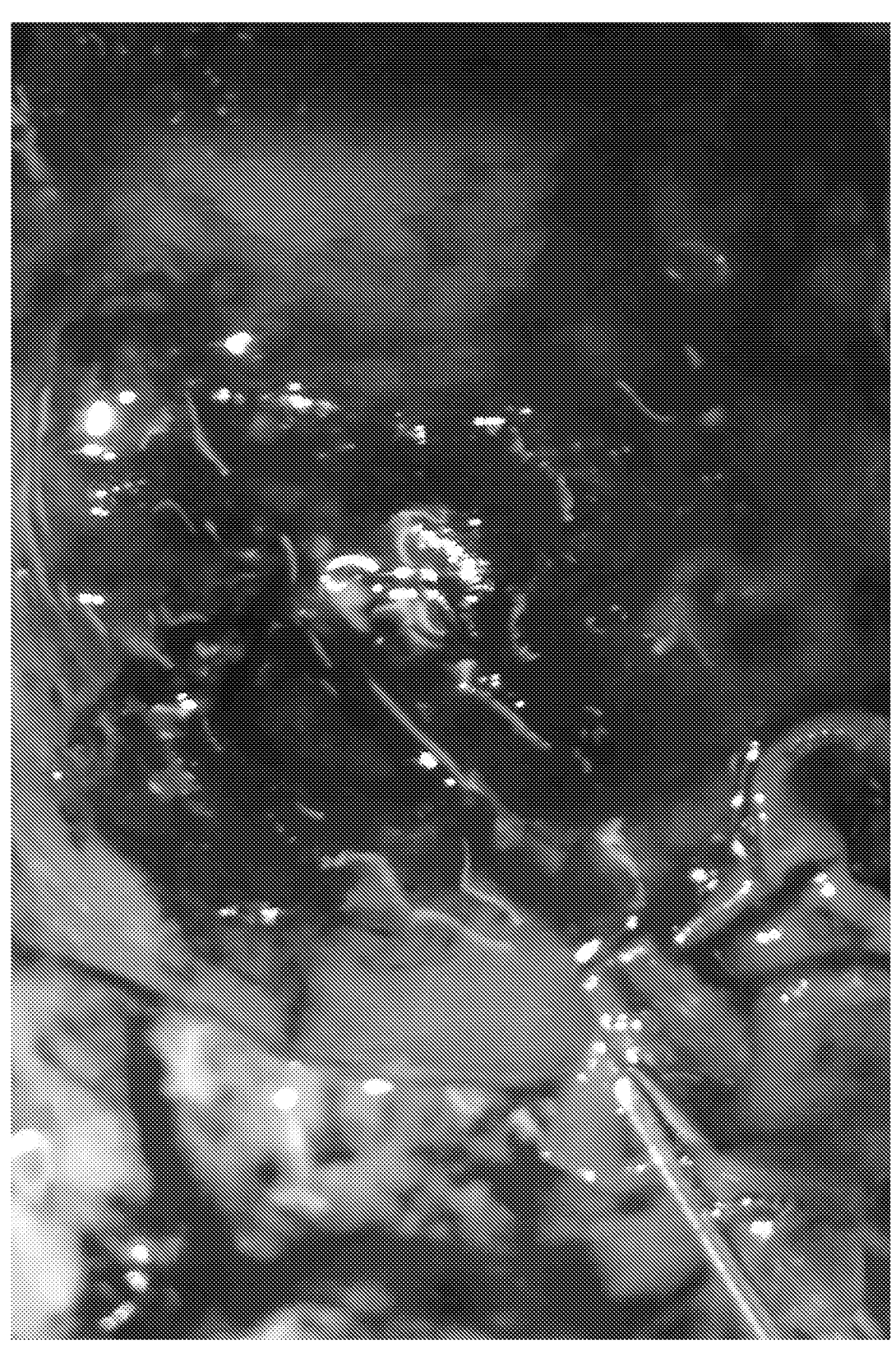
FIG. 19 demonstrates the presence of a strong intact clot under the dressing of FIG. 18 at animal sacrifice which was within 45 minutes of taking the image of FIG. 18. The modified chitosan dressing was shown to be uniformly adhered to the injury and stomach mucosa at sacrifice.
Figure 20:
FIGS. 20-25 depict an experiment involving a circulating peristaltic pumping system of 0.9% saline through a 15 mm diameter glass cell containing a lumen of swine small intestine submucosa that was pumped for 163 hours (close to 7 days—168 hours) at 20 ml/min flow rate with temperature of the system close to 27° C. A small 10 mm×10 mm patch of the modified catechol chitosan material of the invention was attached by hand inside the glass cell onto the small intestine submucosal surface and watched over time. The images show that the material remained adhered firmly to the submucosa lumen over the 7 days without any loss in adhesion. At seven days and removal of the lumen from the cell, the material was found to have degraded and become extremely friable. This system was used to screen formulations for the transurethral development. Unmodified chitosan lasted less than 2-3 hours in this model.
Figure 21:
Figure 22:
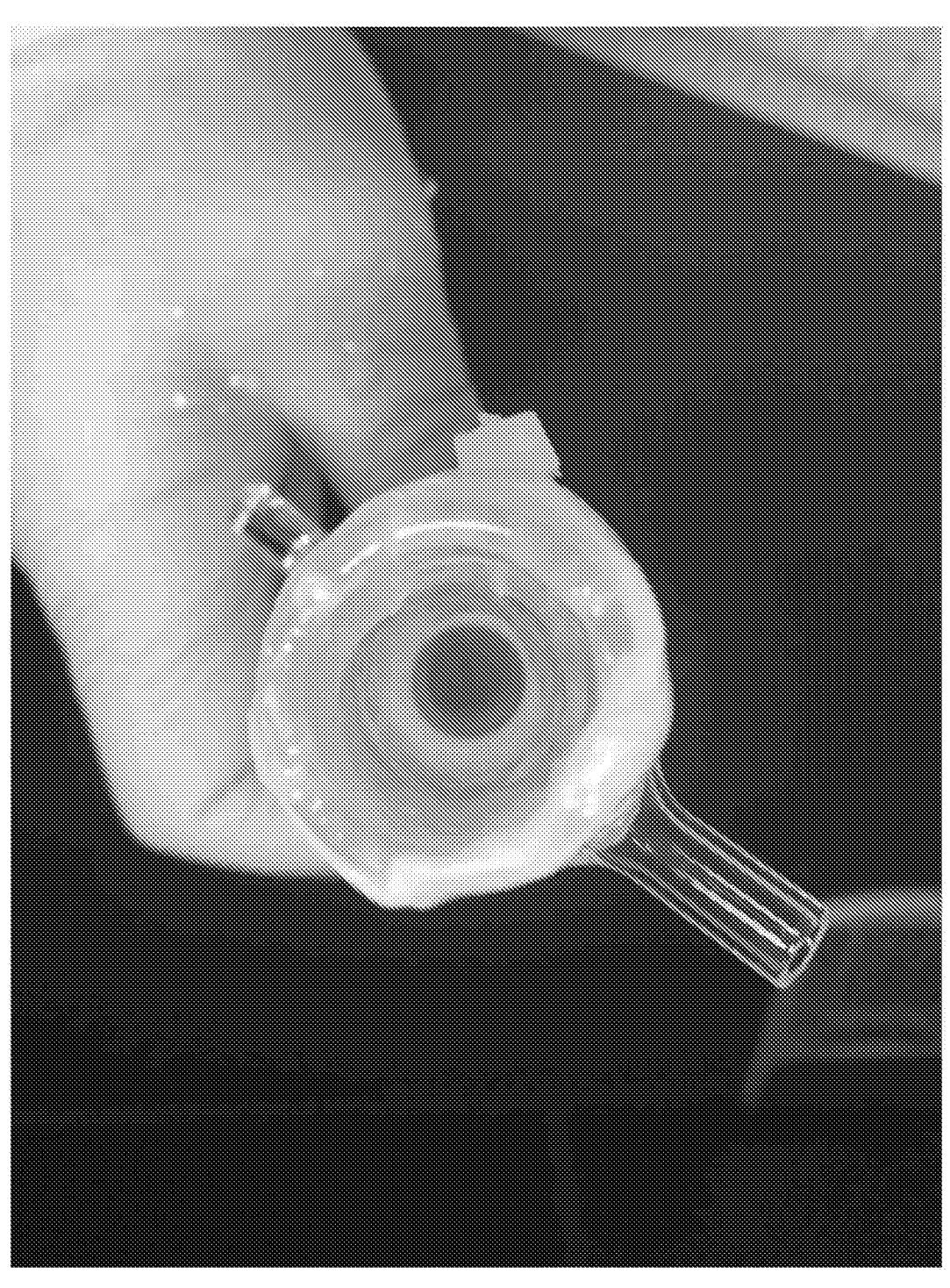
Figure 23:
Figure 24:
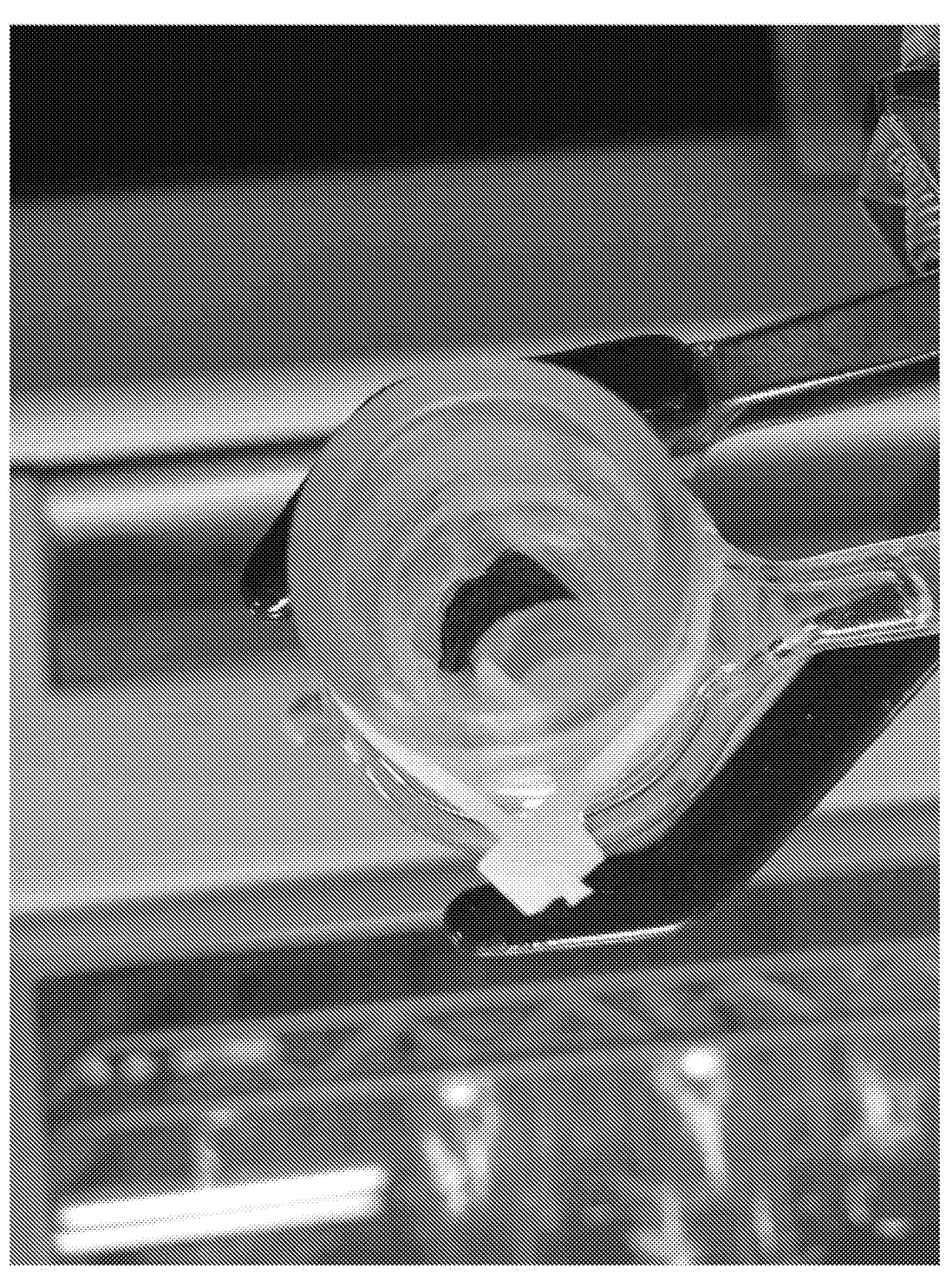
Figure 25:
Figure 26:
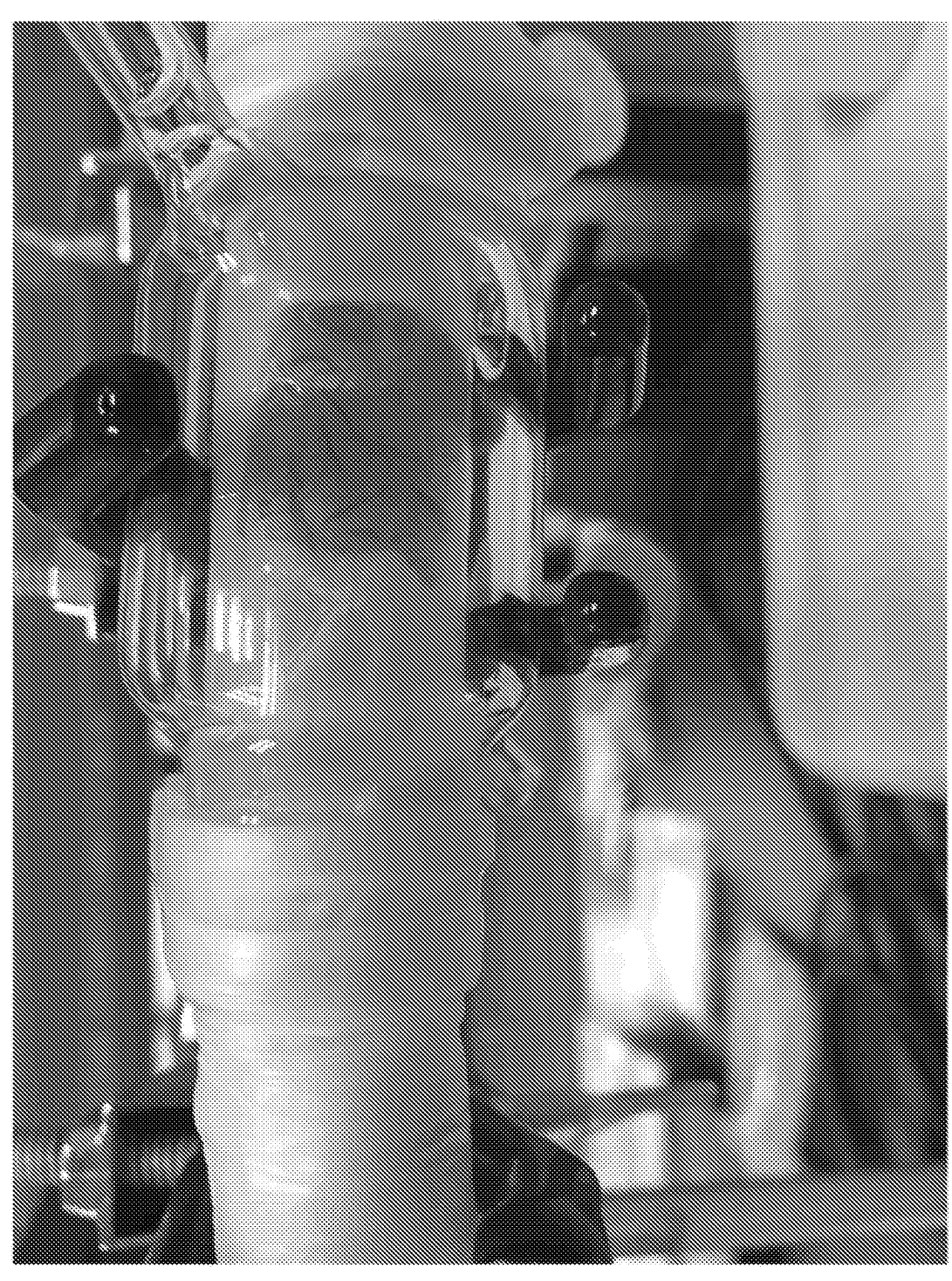
FIG. 26 depicts a gastroscope digital image of the modified catechol chitosan dressing formed from the material of the invention of the invention intimately adhered to stomach mucosa, demonstrating slight swelling in the stomach environment, and effectively controlling upper gastrointestinal hemorrhage (Forrest 1a) of a lacerated gastroepiploic artery inside the stomach of a heparinized (ACT ≥250 s) swine 3 hours after application of the material to the arterial injury.

In a preferred embodiment, the catechol modified chitosan composition is of a brown color resulting from catechol oxidation to o-quinone. The quinone is produced by autoxidation of the catechol hydroxyls in the presence of oxygen and at pH above about 5.5. Schiff base reaction of quinone with chitosan C-2 amine produces crosslinking in the modified chitosan. The color of the catechol modified chitosan composition is controlled during synthesis by controlling pH and oxygen exposure. Maintenance of pH at or below about pH 5.5 inhibits the production of o-quinones. Subsequent conditioning of dialysis solution, final washed, or dialysed catechol chitosan solutions in a preferred pH range 5.8 to 6.2 provides for more dissolution resistant, darker, more oxidized catechol. In some embodiments, the coloration of catechol modified chitosan characterizes one aspect of the catechol modified chitosan dressing. In some embodiments, the coloration reflects the degree of substitution of the chitosan with catechol. In some embodiments, the coloration from pink to brown correlates with the degree of substitution. FIG. 15 shows exemplary embodiments of different colorations reflecting and correlating with different degree of substitution of the chitosan with catechol.

In order to prepare a dry dressing from the catechol chitosan, a preferred light brown to darker brown catechol aqueous chitosan solution is prepared which may be used by itself or may be mixed with other aqueous hydrophilic polymer solutions including but not limited to solutions of chitosan and/or, optionally, hydrophilic polymers. Preferably, the dry phase separated catechol chitosan dressings are prepared as densified dried freeze-phase-separated and fibrous dressing structures.

Figure 6:
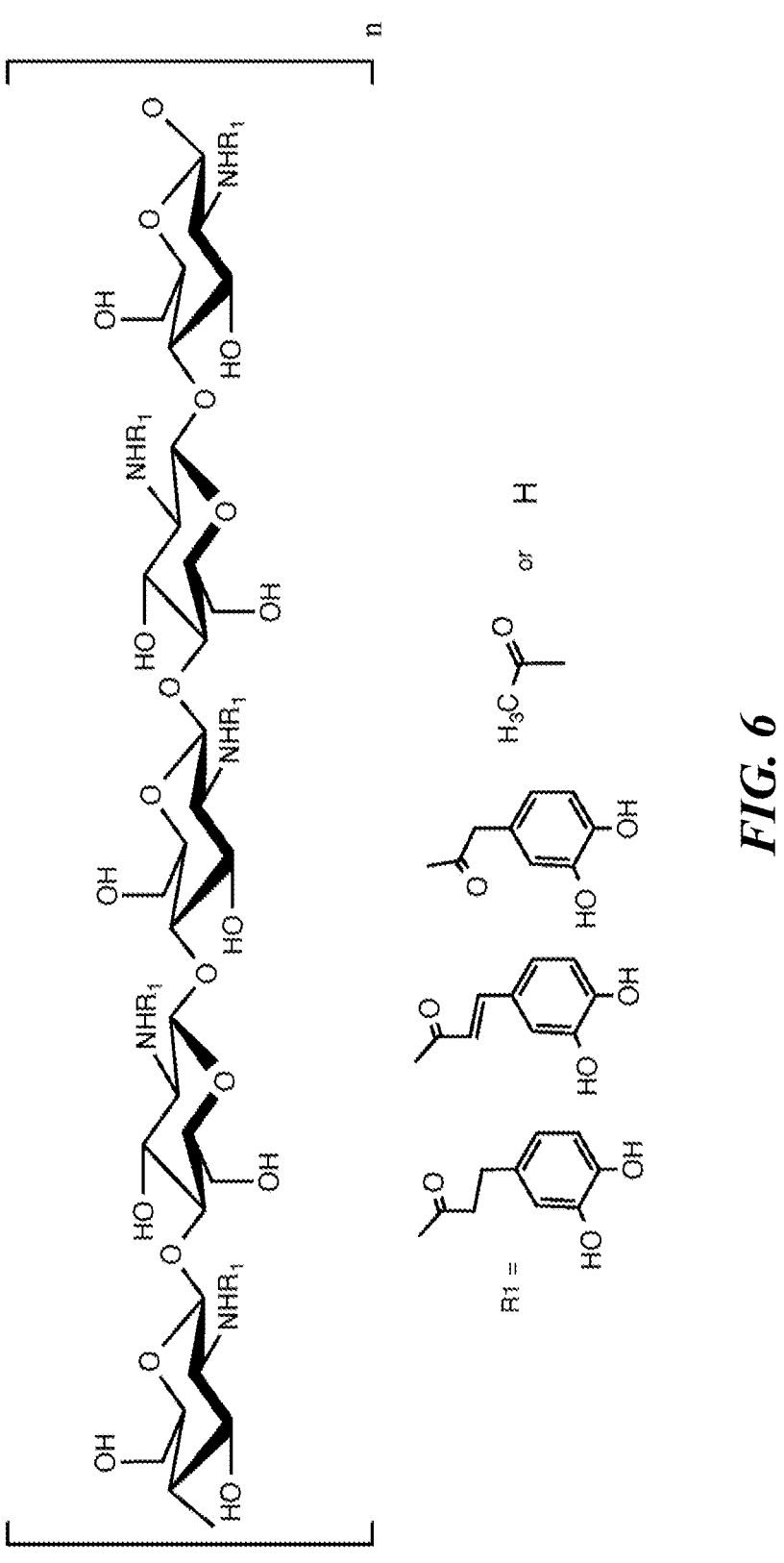
FIG. 6 depicts a chemical structure representation of chitosan (R1=H and acetyl radical) and catechol modified chitosan (R1=H, acetyl, hydrocaffeic acid radical, caffeic acid radical, trans-caffeic acid radical and Homoprotocatechuic acid radical). For chitosan polymer, preferably n>60, more preferably n>300, and most preferably n>600.

Preferred crosslinked catechol modified chitosan compositions of the invention provide good tissue adherence and 10 times to 100 times increased resistance to dissolution in the upper gastrointestinal tract or bladder compared to dressings formed substantially of unmodified chitosan. For example, FIGS. 6A, 6B, and 6C show dissolution testing results demonstrating that chitosan dressings are gone in 15 minutes while some catechol dressings lasted greater than 24 hours. The catechol modified chitosan compositions described herein, provide hitherto unknown longevity, biocompatibility, and ability to eventually dissolve.

Preferred rapid adherence to gastrointestinal mucosa or bladder mucosa of CGHD or CEHD formed from the material of the invention (≤1 minute) is provided in the dry chitosan dressing by the promotion of quaternary ammonium cation formation at the chitosan glucosamine C-2 amine by the presence of an acid in the dry dressing composition. Preferred chitosan acid salts in the dressing may include salts of acetic, lactic, glycolic, citric, succinic, malic, hydrochloric, glutamic, ascorbic, malonic, glutaric, adipic, pimelic, and tartaric acids, and combinations thereof. Preferably the acid salt % weight of the chitosan is greater than about 2% and less than about 15%. To achieve fast adherence (e.g., ≤1 minute) to wet tissue, the moisture in the dry gastrointestinal or bladder dressing is preferably less than about 15% by weight; more preferably it is less than about 10% by weight and most preferably it is less than about 5% by weight.

In the case of densified freeze-phase-separated and dried chitosan dressings, the chitosan solution is poured into the freeze-phase-separation mold (typically in the shape of a pan with a horizontal flat base) with preferably around a 0.1% w/w, more preferably around 0.5% w/w and most preferably 0.25% w/w hydrophilic polymer chitosan solution. The hydrophilic polymer solution is preferably added to the horizontal flat pan to a vertical depth of preferably about 10 mm, more preferably 2.5 mm and most preferably 5.0 mm mold depth. The solution in the mold is subsequently frozen and dried to remove water by sublimation or freeze phase substitution (solvent extraction of the ice with a non-solvent to the polymer) to a low density (>99% void volume) open or porous dry sponge with a dry density <about $0.01$ g/cm$^3$ (or, for example, about $0.005$ g/cm$^3$ for a catechol chitosan uncompressed dressing from 0.5% solution, which is about ⅕ or 20% of the density of an uncompressed HemCon Bandage chitosan sponge, which is about $0.025$ g/cm$^3$). Lyophilization is typically performed at pressure below 300 mTorr while freeze substitution involving a dry, cold (e.g., <−20° C.) solvent such as ethanol is performed at atmospheric pressure. The dry sponges are then compressed, preferably to greater than about $0.4$ g/cm$^3$ density and less than about 100 microns thickness. The preferred compression is not limited to but may include uni-axial compression between aligned flat platens, wherein the platens are heated between 18° C. and 150° C. and are pressure loading up to 10,000 bar.

The preferred compression creates a remarkably thin (e.g., range from about ≤50 microns to about ≤200 microns) strong (e.g., 5 MPa to 25 MPa UTS) readily foldable chitosan dressing that may be placed minimally invasively anywhere in the body in a confined folded form that can be reformed without compromised performance to the original unfolded dressing form for accurate and effective high surface area placement and attachment.

Foldability is addressed in the examples below. In one embodiment, fold testing involved folding the horizontally planar final compressed circular dressing through 1800 edge over edge, first in an anticlockwise direction, holding the edges together and compressing firmly in the middle of the dressing to create a single linear fold axis (or crease) in the dressing. The folded dressing is then opened and the edge to edge fold is reproduced in the new fold axis but with the folding in the opposite clockwise direction. Foldability success can be rated as no tears or cracks being visible along the fold axis and no significant loss in tensile properties of the dressing (determined by gentle pulling across the fold of the dressing). FIG. 15 shows a catechol modified chitosan dressing that has been folded and unfolded, remaining intact, with visible fold axis (crease).

Freeze phase separation of dilute aqueous polymeric solutions results in phase separation of micron and submicron thin polymeric chitosan lamella interspersed regularly between ice crystal sheets close to 200 microns in width. Removal of the ice by sublimation (freeze drying) or alternatively by solvent extraction leaves the dry sponge composed of close-to-aligned, thin (≤1 micron), polymeric chitosan lamella. Compression of the polymeric chitosan lamella at close to or greater than their glass transition temperature (Tg for dry chitosan is near 80° C.) allows for their compression into the thin (near 50 microns) dense polymeric structure formed of layers of hundreds of strong compliant polymeric chitosan leaves (lamella) which do not readily propagate cracks and which can be folded repeatably without failure. Such multi-leaf layering achieves remarkable strength. Prior to the present invention, no one has previously investigated high-density freeze-phase-separated chitosan dressings for manufacture and use as described herein and with the aim to address key problems solved by the present invention such as, for example, adhesion by removal of interfering fluids (by absorption, channeling, displacement, and/or re-direction), ability to form a fold axis and ability to resist mechanical failure on repeated folding and unfolding along the fold axis.

In one embodiment, porosity (void space >99%) is complete and uninterrupted in the non-compressed dressing with pore size range of 20-300 microns with substantially most of the pores near 100-200 microns. The un-interrupted pore structure is indicated in the compressed dressings by their ability to absorb biological fluid such as blood.

In some embodiments, crack free, clean edge holes near 500 microns in diameter may be formed in the dressing after compression by localized application of narrow gauge (near 500 microns in diameter), sharp pointed needle through the dressing and into a flat, hard elastomeric surface applied immediately against the dressing which may receive and release the point of the needle. Preferred receiving support flat surfaces include but are not limited to clean, dry thermoplastic elastomers with Shore 55D to 90D in hardness. Alternative methods of hole formation may include but not be limited to use of a small diameter (near 500 microns) hole punch or a laser cut hole.

In some embodiments, chitosan dressing provided herein has holes in the dressing. In some embodiments, the holes receive fiber or other reinforcing attachment elements. Such a reinforcing element may be formed by simple local application of a reinforcing fluid to locally bind with the edges of the holes. A reinforcing fluid used in the development of the present invention included cyanoacrylate glue which bound the compressed chitosan lamella of the dressing together and prevented local delamination and fibrillation of the chitosan at the hole stress point. Another embodiment of a hole reinforcing element is micro-molded interlocking parts of plastic or metal (dissolvable in the upper gastrointestinal tract or bladder or alternate area in the body of application) that are placed on one side of the hole and the opposite hole side to permanently fit together and be able to support load through the hole without causing dressing delamination, fibrillation or other stress related failure at the dressing hole when loaded. In some embodiments, the micro molded parts may include the part on the side of the attachment to a delivery device that enables convenient snap-on attachment and snap-off detachment of the dressing to the delivery device.

As used herein, the term fold axis is intended as part of the dressing sheet which demonstrates memory in the material of bending stress and or folding and is typically localized to narrow regions of high bending stress and shear. A crease in folded paper is an example of a fold axis.

In a preferred embodiment, the tissue adhesive component of the dressing is formed from a freeze phase separated and dried chitosan sheet with composition including a catechol chitosan. In a preferred embodiment the non-tissue adhesive component of the dressing is formed from a freeze phase separated chitosan dried sheet without any modified chitosan. In a preferred embodiment, both tissue adhesive and non-tissue adhesive dry sheets have density ≤about 0.03 $g/cm^3$ before compression to final density ≥about 0.4 $g/cm^3$.

In order to prepare one dressing from both sheets with the dressing having a tissue adhesive surface layer and a non-adhesive surface layer, the two sheets are bonded together by, for example, placing one sheet on top of the other and applying sufficient uniform pressure over the dressings to compress them to a higher density. In a preferred process, the original densities of each sheet type at ≤about 0.03 $g/cm^3$ is increased to a final dressing density ≥about 0.30 $g/cm^3$. In a more preferred process, the original densities of each sheet type at ≤about 0.015 $g/cm^3$ is increased to a final dressing density ≥about 0.4 $g/cm^3$. In a most preferred process, the original densities of each sheet type at ≤about 0.01 $g/cm^3$ is increased to a final dressing density ≥about 0.5 $g/cm^3$. At the conclusion of the compression, the two compressed sheets are bonded together so that one cannot be readily peeled away from the other and the dressing can be manipulated by folding and furling without any occurrence of separation.

This physical adherence of materials by compression of two or more low density porous materials together to form a final two or more layer porous material of higher density solves a difficult problem of how to adhere such materials together without physical or chemical change to the individual materials and without addition of further bonding agents or adherents. It is contemplated that bonding may be attributed to microsurface impingement and penetration of the dressings through their pores with physical interlocking due to pore compression. This physical interlocking of low density, freeze phase separated, dry sheets is not restricted to two materials of the same thickness or to only two layers since the interlocking effect is neither sidedness nor thickness dependent. Therefore a multi-layered construct of individual freeze phase separated and dried sheets of the same or different materials of the same or different thickness may be formed by layering the low density sheets (preferably with density ≤0.05 g/cm³) and compressing the assembly together to a density ≥0.3 g/cm3). Such a final physically adhered assembly would be expected to provide advantages of thin top and bottom surface layers including but not limited to adhering or anti-adhering materials with layers inside providing including but not limited to structural, physical and chemical elements.

In some embodiments, a chitosan dressing has an adhesive side and a non-adhesive side. In some embodiments, the adhesive side of the chitosan adheres to a tissue and absorbs and/or redirects the surface moisture. In some embodiments, the non-adhesive side detaches from a delivery device upon attachment of the chitosan dressing to the injury site wherein the chitosan dressing has become wet. This is in part because the adhesion strength of the chitosan dressing to the tissue surface controls the dressing location upon detachment of the dressing from the delivery device. Detach or "readily detach" as used herein in a two-sided chitosan dressing indicates that the chitosan dressing, with its adherent side applied to a tissue surface or an injury site and adhered due to absorbance of moisture, stays at the tissue surface or injury site while the non-adherent side releases from the delivery device, thereby allowing the delivery device to be retracted from the injury site without disrupting the position of the chitosan dressing on the tissue surface or injury site. In some embodiments, the chitosan dressing, when dry, attaches to the delivery device, thereby allowing delivery of the chitosan dressing along with the device onto an injury site.

In one embodiment, there is a need to attach the dressing locally to the delivery device. Generally, these local attachment areas are at the extremity of the dressing. For example, one design is to provide for local pinpoint attachment on the dressing extremity tabs at the circumference of the dressing and for no other attachment locations to avoid the risk of attaching the dressing to the delivery sheath, the delivery device, or itself (when furled/folded). The attachment locations may be designed to weaken when wet or alternatively be activated for release by some type of physical release mechanism.

In one mechanism, chitosan dressing provided in this disclosure is able to stop bleeding by absorbing, channeling, and/or redirecting the hydrophilic and hydrophobic fluids at an injury site. The absorption clears enough moisture from the injury site to allow subsequent hemostatic reactions between the chitosan dressing and the tissue at the injury site, which in turn stops bleeding and allows the chitosan dressing to stay attached; thus, sealing the injury site. The porous, dense, and multi-layer structure of chitosan dressing provided herein facilitates the absorption, channeling, and/or redirection of the moisture at the injury site, and the attachment or adherence of the chitosan dressing to the injury site.

The chitosan dressing disclosed herein is biocompatible. In some embodiments, the dissolved residue from a chitosan dressing applied to an injury site in vivo passes safely through the alimentary tract or urethra and is excreted along with other bodily waste.

More than one, or multiple, chitosan dressings may be used or applied in serial fashion to a tissue treatment site or injury site. When more than one chitosan dressing is deployed, such dressings may separately adhere to adjacent tissue site or injury site areas, or may overlap with each other to varying extents. Due to the thinness of the chitosan dressing described herein, depending on the application, it is contemplated that multiple chitosan dressings may be used as needed to promote or achieve hemostasis of an injury site.

In one embodiment, the chitosan dressings overlap one another upon application. In such an instance, ideally there would be some adherence of the wetted adhesive side of the subsequent dressing to the wetted dressing backing of the earlier dressing. Accordingly, in one embodiment, the chitosan dressing does not have an anti-adherent backing but does have a backing with a weak wet adherence that provides for sufficient adherence for placement of a subsequent overlapping chitosan dressing.

Delivery Device

A delivery device, as used herein, is a device for delivering chitosan dressing. A delivery device delivers a chitosan dressing to injury sites at different locations in the body of an animal including human, pigs, dogs, etc.

In some embodiments, a delivery device is a minimally invasive device that can deliver a dressing, e.g., a chitosan dressing, to a physiological site in the body of an animal, in non-invasive or minimally invasive manner. In some embodiments, the delivery device is a balloon device. In some embodiments, the delivery device is a wire device or a device laser-cut from a small diameter cylinder of nitinol or stainless steel. In some embodiments, the non-invasive or minimally invasive feature of the delivery device is achieved through delivery of a dressing, e.g., a chitosan dressing, through a narrow catheter or a comparable working channel. In some embodiments of CGHD, the catheter or the comparable working channel has a diameter that is less than 3.2 mm. In other CGHD embodiments, a gastroscope channel may range in diameter size from 2.8 mm to 4.5 mm. In some CEHD embodiments, the balloon catheter or the comparable working channel has a diameter that is less than about 7 mm. In other CEHD embodiments, a channel of a TURP delivery device may range in diameter size from 5 mm to 7 mm.

In some CGHD embodiments, the catheter or balloon catheter or the comparable working channel has a diameter that is less than 3.2 mm. In other CGHD embodiments, a gastroscope channel may range in diameter size from 2.8 mm to 4.5 mm.

In some CEHD embodiments, the catheter or balloon catheter or the comparable working channel has a diameter that is less than about 7 mm. In other embodiments, a channel of a TURP delivery device may range in diameter size from 5 mm to 7 mm.

Exemplary delivery devices include, but are not limited to, a balloon device, a balloon catheter, a wire device, a cylindrical device with laser-cut ends, a indwelling catheter, a urethral or suprapubic catheter, an external catheter, a short-term catheter, and an intermittent catheter.

A delivery device can also be an endoscopic device used in various aspects of medical procedures. In some embodiments, the endoscopic device is non-invasive or minimally invasive due to a narrow catheter or tube/tubing or a similarly narrow-diameter portion of the device.

A delivery device can also be a transluminal or transurethral delivery device. In some embodiments, the transurethral delivery device is non-invasive or minimally invasive due to a narrow catheter or tube/tubing or a similarly narrow-diameter portion of the device.

Delivery devices include other devices with narrow-diameter tubings or catheters or similar structures.

Attachment of the Dressing to the Delivery Device

CGHD

Freeze phase separated dressings are composed of compacted layers of friable and delamination prone lamella that require special attachment of the dressing to wire and cylindrical laser-cut delivery devices. Each dressing attachment point to the delivery device must be able to withstand up to 50 to 100 g of load during furling and unfurling of the dressing. Because of the low cohesion strength of surface lamella, direct adhesion (such as by cyanoacrylate glue) of the dressing to the delivery device is not an option for freeze phase separated dressings formed from well dissolved solutions. One embodiment where this is less problematic is where the catechol chitosan is formed from carbonic acid dissolved chitosan wherein the base precipitated and subsequently water-washed pure chitosan aqueous gel before dissolution in the carbonic chitosan contains a dispersion of solid chitosan fibers (≥0.2% w/w of the chitosan) insoluble in the carbonic acid that provide reinforcement to the subsequently catechol modified chitosan from carbonic solution. Besides this carbonic acid chitosan instance of a low fraction (0.2% to 5% w/w of the chitosan) chitosan fiber reinforcement of the freeze phase separated bulk and surface structure of the dressing, the preferred manner of local reinforcement and attachment of the dressing to the delivery device in the case of wire delivery is by placement of small diameter (near 500 microns), through and through holes with reinforcement elements in the dressing at the points of attachment to the delivery device.

Preformed holes in the freeze phase separated, dried dressing sponge are a preferred way to make receiving holes in the uncompressed dressing sponge. Because the low density uncompressed sponges (<0.05 g/cm3) readily delaminate, are highly friable and thus cannot receive normal hole making approaches which involve any load on the sponge, the preferred method to make holes in these sponges without any damage to the sponge lamella structure is to apply insulating, hydrophobic (non-adherent) rod mandrels to the mold solution (from the top of the solution, through the solution to the other side and contacting the base surface of the mold and preferably through the base surface and into the base of the mold) immediately before freeze phase separation of the solution. These mandrels may be tapered to allow ease of removal after drying of the freeze phase separated sponge. It is envisioned that such mandrels would be made of a rigid or semi-rigid hydrophobic material that could be machined or molded. Mandrel materials that would be suitable include but are not limited to the fluorinated material products such as polytetrafluoroethylene (PTFE) sold under the trademark TEFLON™ (Chemours, US) and polychlorotrifluoroethylene (PCTFE) sold under the trademark KEL-F® (Emco Industrial Plastics LLC, US) and high density polyethylene (HDPE). The diameter of the hole made after removal of the mandrel is designed to allow thread to be easily placed through friable uncompressed sponge without damage to the sponge. The mandrels may be supported in the mold by slotting into suitably sized receiving holes in the mold base surface. Alternately they may be supported by a sheet of releasable hydrophobic film placed immediately over the upper surface of freeze phase separation mold and the mold solution. This film would be removed from the frozen phase separated surface, leaving the mandrels in place, before drying in the case of drying of the freeze phase separated solution. After drying, the preformed holes are thus ready to receive tie thread for attachment of dressing to delivery/deployment device. The tie thread is positioned in sponge before compression in suitable arrangement to take all the forces on dressing furling, unfurling, and delivery. Compression of sponge (from low density <0.05 g/cm3 to high density (>0.4 g/cm3) locks the tie thread and any other element of reinforcement/attachment in place. The thread may be glued in place before or after dressing compression or the thread may be used to locally apply a liquid reinforcing element such as cynanoacrylate glue locally through the hole with the thread removed after application. An alternate embodiment for forming suitable holes in the uncompressed sponge for taking a supporting thread or other type of supporting element is by laser hole cutting.

Crack free, clean edge holes near 500 microns in diameter may be formed in the dressing after compression by localized application of narrow gauge (near 500 microns in diameter), sharp pointed needle through the dressing and into a flat, hard elastomeric surface applied immediately against the dressing which may receive and release the point of the needle. Preferred receiving support flat surfaces include but are not limited to clean, dry thermoplastic elastomers with Shore 55D to 90D in hardness. Alternative methods of hole formation may include but not be limited to use of a small diameter (near 500 microns) hole punch or a laser cut hole.

Holes in the dressing can receive fiber or other reinforcing attachment elements. Such reinforcing element may be formed by simple local application of a reinforcing fluid to locally bind with the edges of the holes. A reinforcing fluid used in the development of the present invention included cyanoacrylate glue which bound the compressed chitosan lamella of the dressing together and prevented local delamination and fibrillation of the chitosan at the hole stress point. Another embodiment of a hole reinforcing element is micromolded interlocking parts of plastic or metal (dissolvable in the upper gastrointestinal tract or alternate area in the body of application) that are placed on one side of the hole and the opposite hole side to permanently fit together and be able to support load through the hole without causing dressing delamination, fibrillation or other stress related failure at the dressing hole when loaded. It is envisioned that such micro molded parts may include the part on the side of the attachment to the delivery device that enables convenient snap-on attachment and snap-off detachment of the dressing to the delivery device.

General delivery device release of dressing may be achieved by a number of methods include snap-off detachment. A preferred method of dressing release is by using a delivery device to dressing attachment fiber that is strong when dry and weak when wet. Such fiber includes but is not limited to chitosan fiber that has been treated to become rapidly water soluble. Preferred chitosan fiber is water soluble multifilament fiber with strength >30 MPa when dry and <than 0.1 MPa when wet.

CEHD (TURP Dressing Attachment to the Balloon)

In one embodiment, the circular dressing is folded once over itself edge to edge and then the folded dressing (now half) is folded once again edge to edge of itself (now a quarter). The dressing is unfolded and now there are two fold lines passing through the middle of the dressing. A tracing of the circumference of the catheter is drawn in the middle of the dressing (a small central circle). A scissors point or other sharp cutting instrument is used to cut along the intersecting fold lines in the middle of the dressing up to the drawn circumference of the catheter. Once the fold lines have been cut there are now four triangular windows or catheter connection tabs in the middle of the dressing. The catheter can be threaded thru the central opening in the dressing and the dressing tabs can be attached by double sided adhesive tape or other adhesive method of application to secure the tabs against the desired location of the catheter to set the bulk of the dressing over and against the catheter balloon. The dressing tabs are preferably placed on the side of the dressing facing away from the catheter balloon over which the dressing is to be folded. Preferably the adhesive used to attach the tabs to the catheter is water soluble to allow the dressing to slide off the catheter and be left in place (with optional catheter removal) after a pressure application by balloon catheter.

Applications and Methods of Treatment

The chitosan dressing embodiments formed from the material of the invention provided in this disclosure may be used to stop bleeding in suitable diseases, conditions, disorders, or emergent traumas or injuries. In some embodiments, the dry solid chitosan material of the invention may be used to stop bleeding from any wet physiological surface, e.g., mucus. Exemplary applications include, but are not limited to, gastrointestinal tract or bladder bleeding, other intraluminal applications, including vascular applications, internal surgical bleeding, internal biopsy bleeding, internal bleeding following parenchymal organ resection, and oral, ocular, auditory or nasal bleeding. Additional applications that might require addition of water or fluid to encourage adhesion of the chitosan dressing to a tissue surface or injury site are also contemplated, for example, use of the chitosan dressing on external body surfaces.

The dry solid chitosan material of the present invention may be used for treatment of gastrointestinal bleeding that may include but not be limited to treatment of bleeding in esophageal varices, bleeding from peptic ulcers, bleeding from duodenal ulcers, bleeding associated with biopsy of the upper and lower gastrointestinal tracts, resections of the upper and lower gastrointestinal tracts, and tears or ruptures in the upper and lower gastrointestinal tracts. Other diseases, conditions, disorders, or emergent traumas or injuries may include, but are not limited to, internal arterial injury; internal bleeding from the liver, internal bleeding from the vena cava; injury in the thoracic cavity including perforations of the heart and lungs and their vessels; and injuries of the abdominal cavity.

The chitosan material of the present invention may also be used for treatment of transurethral prostatectomy and or bladder neck bleeding that may include but not be limited to treatment of bleeding.

The chitosan material of the present invention may also be used following acute internal injury (such as occurring in UGIB, TURP or other minimally invasive procedure or in open surgery) to protect the injured site by closing the site of injury and providing an environment conducive to cellular regeneration before dissolving or degrading within 7 days.

The chitosan material of the present invention may also be used to be delivered to, and to locally adhere to, specific target sites for general therapeutic purposes including active pharmaceutical agent and/or biological agent delivery. Such target sites would include but not be limited to anastomoses, esophageal varices, peptic ulcers, resected prostatic fossa, resections and biopsies of the liver, resections and biopsies of the kidney, resections and biopsies of the bladder, resections and biopsies of the throat, resections and biopsies of the pancreas, resections and biopsies of the stomach, resections and biopsies of the lower gastrointestinal tract, resections and biopsies of the lung, and resections and biopsies of the heart.

The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

EXAMPLES

Examples 1-6 are drawn to CEHD chitosan dressings.

The following materials and preparations were considered in the chitosan endoluminal hemostatic dressing inventive process.

Chitosan A: Primex ChitoClear 65010, TM 4375, MW=250-300 kDa, Brookfield

Chitosan B: Primex ChitoClear 43000, TM 4167, MW=110-150 kDa, Brookfield viscosity in 1.0% w/w chitosan solution in 1.0% acetic acid at 25° C. and spindle LV1=9 cPs, DDA=95% (by colloidal titration).

Glacial acetic acid: Fisher Scientific, Catalogue No. A38-212.

Hydrochloric acid: 1.0 M aqueous solution Sigma Aldrich, Catalogue No. H9892.

L-Lactic acid: JT Baker, Catalogue No. 0196-01.

Glycolic acid: JT Baker, Catalogue No. M821-05.

Sodium hydroxide: 5.0 M NaOH aqueous solution Sigma Aldrich, Catalogue No. S8263-150 ml.

Potassium hydroxide: 0.1 M KOH in methanol (BDH).

Ethanol: 2000 Proof Sigma Aldrich, Catalogue No. 459844-1L.

Acetic anhydride: ACS reagent grade obtained from Sigman Aldrich, Catalogue No. 320102-1L.

3,4-Dihydroxyhydrocinnamic acid (hydrocaffeic acid): 98% Sigma Aldrich, Catalogue No. 102601.

3,4-Dihydroxycinnamic acid (caffeic acid): 98% Sigma Aldrich Catalogue No. C0625 trans-3,4-Dihydroxycinnamic acid (trans-caffeic acid): Sigma Aldrich Catalogue No. 51868

3,4-Dihydroxyphenylacetic acid (DOPAC, Homoprotocatechuic acid): 98% Sigma Aldrich Catalogue No. 850217.

1-ethyl-3-(-3-dimethylamino-propyl)-carbodiimide: (alternatively N-(3-dimethylaminopropyl)-N'-ethylcarbodiimide hydrochloride with common acronym EDC) Sigma Aldrich, Cat. #E7750.

N-acetyl-L-cysteine Sigma Aldrich, Catalogue No. A7250

Sodium Chloride Sigma Aldrich, Catalogue No. 793566-500g.

Glycerol: Sigma Aldrich, Catalogue No. G-8773.

Polyethylene glycol: Spectrum, Catalogue No. PO108.

Polyethylene oxide: Mw 400,000 da, Sigma Aldrich Catalogue No. 372773-500G.

Poloxamer 407: Spectrum, Catalogue No. P1166.

Sucrose: Sigma Catalogue No. S3929.

D-Sorbitol: Sigma Catalogue S1876

Hydroxypropyl cellulose (HPC): Aldrich Catalogue No. 191892

Hydroxyethyl cellulose (HEC): Aldrich Catalogue No. 308633.

Synthetic urine formulation: Add calcium chloride dihydrate Sigma Catalogue No. C5080 (1.30 g); magnesium chloride hexahydrate Sigma Catalogue No. M2670 (1.30 g); sodium chloride Sigma Catalogue No. 793566 (9.20 g); sodium sulphate Aldrich Catalogue No. 238597 (4.60 g); sodium citrate dihydrate Sigma catalogue No. S4641 (1.30 g); sodium oxalate Sigma Catalogue No. 71800 (0.04 g); potassium dihydrogen orthophosphate Sigma Catalogue No. P5655 (5.60 g); potassium chloride Fisher Catalogue No. BP366 (3.20 g); ammonium chloride Sigma Catalogue No. 09718 (2.00 g); urea Sigma catalogue No. U1250 (50.00 g); creatinine Acros Catalogue No. 228940500 (2.20 g) to a 2.0 liter volumetric flask and add 1.5 liters of deionized water to dissolve. After dissolution of ingredients in water and equilibration of solution temperature to room temperature, make up to 2.0 L mark with deionized water.

Porcine bladder with urethra, Animal Biotech Industries Inc., (Danboro, PA 18916)

Porcine small intestine casing, Butcher and Packer (29/32 mm) (Madison Heights, MI 48071)

Citrated bovine whole blood: Lampire Biological Laboratory Bovine CPD, Catalogue No. 7720010.

Cynaoacrylate A: Permabond 910 Tissue Adhesive, Catalogue No. 72590.

Cyanoacrylate B: Loctite 4902 instant adhesive Catalogue No. 1875841

Dialysis Tubing: 3,500 Da MWCO Snakeskin Dialysis Tubing (Fisher Scientific), Catalogue No. PI88244.

Parafilm: "M" Laboratory film, Pechiney plastic packaging (Chicago, IL 60631)

Adhesive: Double sided 3M Catalogue No. 21200-46144-6 (St Paul, MN 55144)

Scotch Fine Line Tape 218, 3M Catalogue No. 70-0060-4397-3 (St Paul, MN 55144)

Example 1

Preparation of Catechol Chitosan and Characterization

Figure 7:
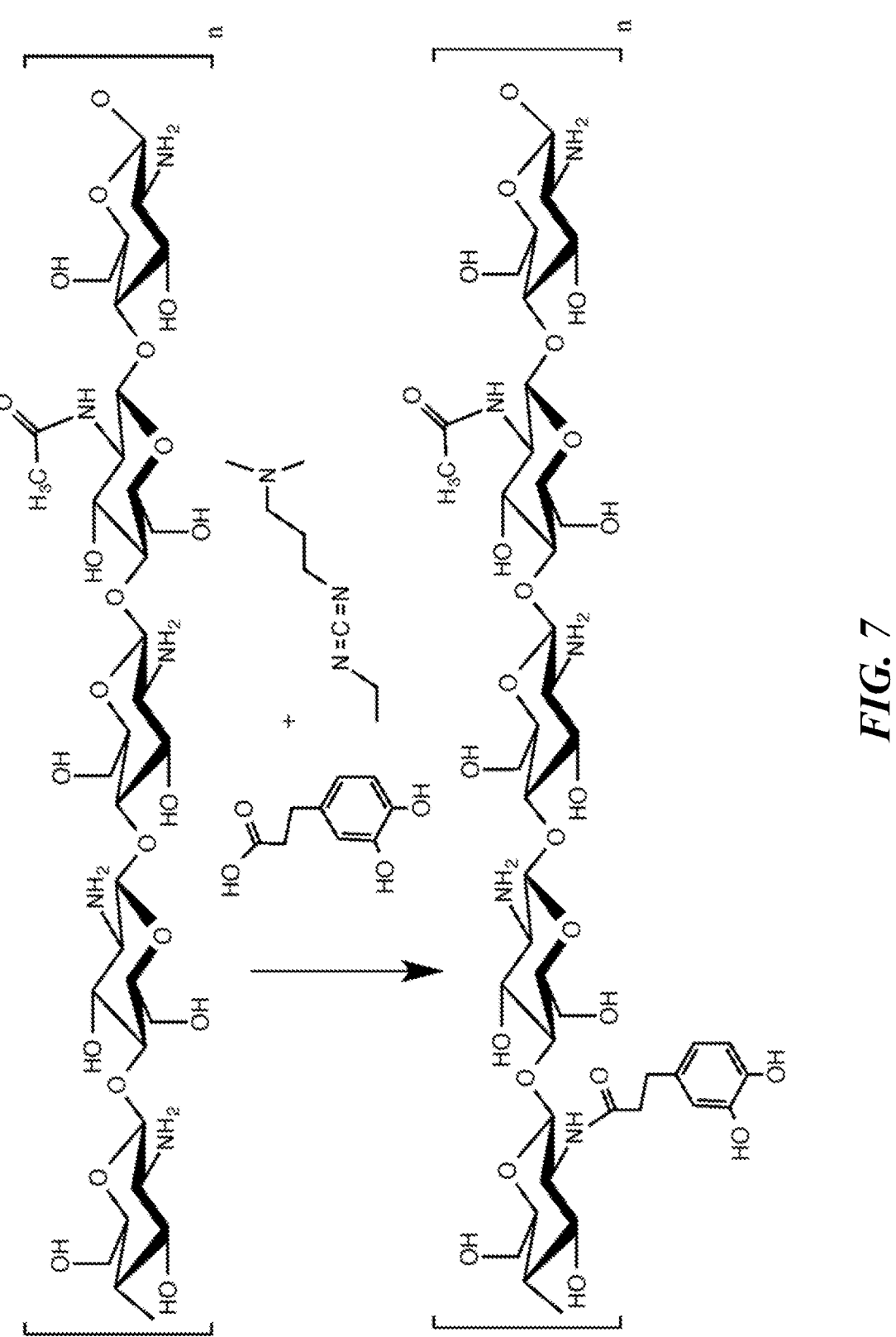
FIG. 7 depicts an N-acylation addition reaction in the presence of 1-ethyl-3-(-3-dimethylamino-propyl)-carbodiimide where 3,4-dihydroxyhydrocinnamic is covalently attached to a chitosan C-2 amine with a degree of substitution of 25% in aqueous solution at pH 5.5.
Figure 8:
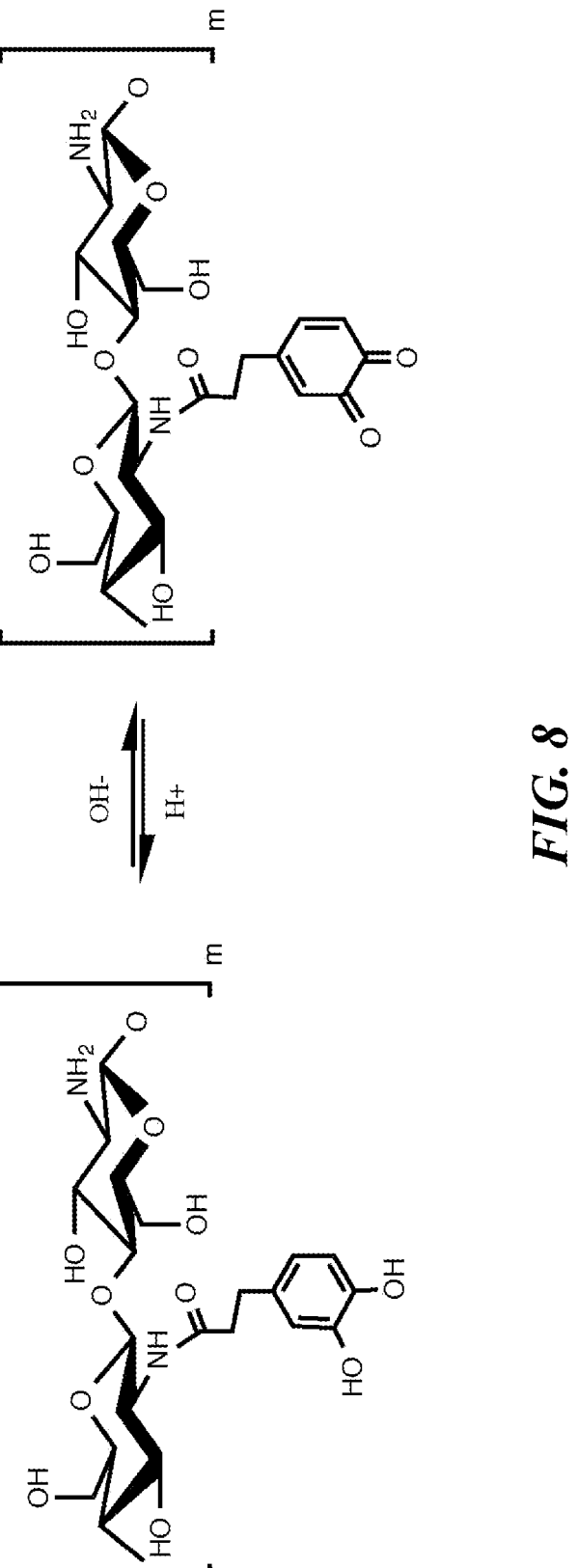
FIG. 8 depicts oxidation of catechol modified chitosan to ortho-quinone modified chitosan under elevated pH and in the presence of oxygen
Figure 9:
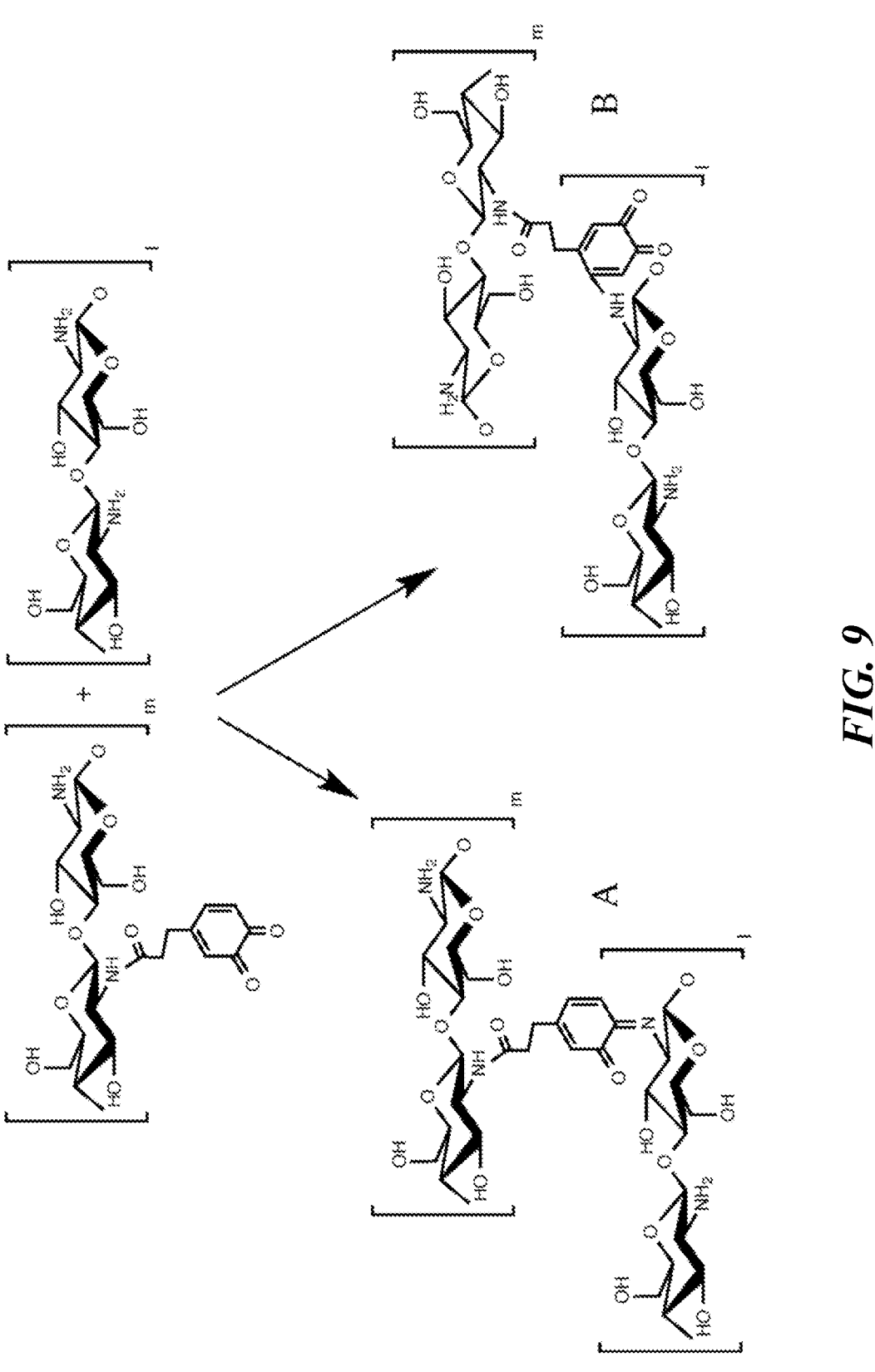
FIG. 9 depicts Schiff base (A) and Michael addition (B) reactions causing crosslinking between catechol modified chitosan and chitosan.

Catechol chitosan synthesis is an N-acylation reaction between a catechol molecule containing a terminal carboxylic acid and the C-2 amine of glucosamine mer of the chitosan (See FIG. 7). The reaction is performed at controlled pH in dilute aqueous solution at room temperature. FIGS. 12A and 12B provide a number of examples of catechol modified formulations used in the preparation of the invention. Column 1 of FIG. 12B provides a list of dressing preparations. The formulations of the preparations are listed in column 2 of FIG. 12B. Catechol chitosan formulations have an acronym of "Cs-Cat". The Cs-Cat formulation number is provided immediately after the "Cs-Cat" and is written "Cs-Cat, XX" where XX is a numeric representing the catechol chitosan formulation number. Chitosan solutions were prepared and these are written as "Chitosan" or "Cs" typically with the acid (lactic or acetic) used to provide aqueous solution. HPMC is hydroxypropylmethyl cellulose. HPC is hydroxypropyl cellulose whereas HEC is hydroxyethyl cellulose. Chitosa lots are shown in column 3. The catechol degree of substitution of the chitosan (column 4 of FIG. 12B) was determined as follows: Quartz UV test cells, 1 cm path length, ×2 (HACH Co., cat #48228-00) were used in acquiring UV/vis spectra. The UV/Vis spectrophotometer was a Varian Cary Bio 100. Standard solutions of 3,4-dihydroxyhydrocinnamic acid were prepared in water and absorbance at 280 nm was plotted against concentration. The extinction coefficient 6 in the Beer Lambert relationship shown below for absorbance in dilute solution $$A = \varepsilon \cdot c \cdot l$$

A is absorbance (dimensionless) and l is the path length.

(Absorbance <0.5) was determined as 2,540±50 liter/(mol·cm). This value was used to determine degree of substitution in the modified chitosan in dilute aqueous solution of known mass of modified chitosan, known volume of solution and measured peak absorbance at 280 nm.

The chitosan catechol solution is diluted so that its absorbance at 280 nm is less than 0.5 (usually about 1:50 or 1:100). The absorbance, the weight of the solution used in the dilution, and the percent solids (CS-catechol) were used to find the fractional degree of substitution ($f_{DS}$) of the HCA with respect to free amines on the chitosan backbone according to the equations:

$$f_{DS} = \frac{n_{HCA}}{f_{DDA} \cdot n_{total\ Chitosan\ mers}}$$

$$f_{DS} = \frac{A \cdot V \cdot \{(f_{DDa} \cdot 161) + (1 - f_{DDA} \cdot 203)\}}{\varepsilon \cdot l \cdot \left\{ m_{cc} - \left( \frac{A \cdot V}{\varepsilon \cdot l} \cdot 165.17 \right) \right\} \cdot f_{DDA}}$$

where A is UV/vis absorbance at 280 nm of the modified chitosan; V is the volume (liters) of the modified chitosan solution taken to dry to constant dry mass; $m_{cc}$ is the measured dry mass (g) of the catechol modified chitosan; $f_{DDA}$ is the fractional degree of deacetylation of the chitosan.

The percentage solute (primarily hydrophilic polymer) in the solutions is shown in column 5 of FIG. 12B. The depth of solution poured into the flat well mold for freeze phase separation is provided in column 6 of FIG. 12B. On freezing the depth of pour remains substantially unchanged so that after freeze drying the depth of pour provides a helpful indicator for the extent of compression change when referencing a the final set of the compressed dressing (provided in column 7 of FIG. 12B). The final density of the dry compressed dressing is provided in column 8 of FIG. 12B. Column 9 of FIG. 12B provides any additional information regarding the dressing preparation. It is interesting to note that the dressing 17 preparation was carried to a high degree of dryness while dressing preparations 71, 79, 80, 83, 84 and 85 were all performed with co-compression of a non-catechol chitosan dressing. These non-catechol chitosan dressings used as backings were all formed from 5 mm poured 43000 0.5% w/w chitosan acetic acid solution.

Examples of the catechol chitosan syntheses are given in the 6 approach variants provided below.

Approach 1

CS-Catechol, Batch 15:

Chitosan (1.51 g) was dissolved in deionized water (140 g) with 1.0 M HCl (5 mL). A 1:1 v/v solution (145 mL) of deionized water to ethanol was prepared. 3,4-dihydroxyhydrocinnamic acid (HCA; 10.5 mmol) and N-(3-dimethylaminopropyl)-N'-ethylcarbodiimide hydrochloride (EDC; 13.0 mmol) were dissolved in the water/alcohol solution solution. Next, the water/alcohol solution solution was slowly added to the chitosan solution prepared above and the reaction mixture was put on stirring. The pH of the reaction mixture was maintained at 5.5 using 5.0 M NaOH solution and left to react overnight. After reacting overnight, the solution was dialyzed against 5 L of deionized water acidified with 1 drop of 1.0 M HCl solution for three days and against deionized water for 4 hours. Dialysate was changed periodically (at least every 24-48 hours) throughout the duration of the dialysis.

Approach 2

CS-Catechol, Batch 22-1:

Chitosan (9.03 g) was dissolved in deionized water (126 g) with 1.0 M HCl (30 mL). The pH of the solution was then brought to 5.1 using 1.0 M NaOH solution. A 1:1 v/v solution (150 mL) of deionized water to ethanol was prepared and N-(3-dimethylaminopropyl)-N'-ethylcarbodiimide hydrochloride (EDC; 31.3 mmol) was dissolved in the water/alcohol solution solution. 3,4-dihydroxyhydrocinnamic (HCA; 15.7 mmol) was dissolved in of deionized water (15 mL). Next, the HCA solution was slowly added to the chitosan solution prepared above and the reaction mixture was put under overhead stirring. The EDC solution was then added slowly to the HCA/chitosan solution. The pH of the reaction mixture was maintained at 4.9 using 0.1 N KOH in methanol solution. After reacting overnight, the solution was dialyzed against 5 L of deionized water acidified with 1 drop of 1.0 M HCl solution for four days. Dialysate was changed periodically (at least every 24-48 hours) throughout the duration of the dialysis.

Some of the solution isolated from CS-catechol, batch 22 after dialysis was placed in an oven to concentrate the solution. The solution was baked at 80 C and the volume decreased by approximately one third.

Approach 3

CS-Catechol, Batch 32 (Prototype A, Acute In-Vivo I):

Chitosan (1.504 g) was dissolved in deionized water (143.5 g) with 1.0 M HCl solution (5.0 mL). The pH of the solution was then brought up to 5.5 with 1.0 M NaOH solution. A 1:1 v/v solution (150 mL) of deionized water to ethanol) was prepared and N-(3-dimethylaminopropyl)-N'-ethylcarbodiimide hydrochloride (EDC; 2.93 mmol) and 3,4-dihydroxyhydrocinnamic (HCA; 10.41 mmol) were dissolved in the water/alcohol solution solution. Next, the water/alcohol reactant solution was slowly added to the chitosan chloride solution. The pH was controlled between 4.9 and 5.5 during addition of the reactants to the chitosan solution using 1.0 M NaOH solution. After addition of the reactants, the reaction mixture was monitored for 2-4 hours and the pH was controlled between 5.4 and 5.7 using drops of 1.0 M HCl and 1.0 M NaOH as needed. Next, pH was controlled to 5.5 and left to react overnight. After reacting overnight (approximately 18-24 hours), the pH of the chitosan catechol solution was controlled back to 5.5. Next, the chitosan catechol solution was dialyzed against 5 L of deionized water at approximately pH 5.8 for 5 days, and against deionized water at approximately pH 6.1 for 4-24 hours. Dialysate was changed periodically (at least every 24-48 hours) throughout dialysis procedure.

Approach 4

CS-Catechol, Batch 33

Chitosan (0.507 g) was dissolved in deionized water (47.5 g) with 1.0 M HCl solution (2.0 mL). The pH of the solution was brought up to 5.5 using 5.0 M NaOH solution. A 1:1 v/v solution (50 mL) of deionized water to ethanol was prepared and N-(3-dimethylaminopropyl)-N'-ethylcarbodiimide hydrochloride (EDC; 2.94 mmol) and 3,4-dihydroxyhydrocinnamic (HCA; 1.49 mmol) were dissolved in the water/alcohol solution (-reactant solution-). Next, the reactant solution was slowly added to the chitosan chloride solution. The pH was controlled between 5.4 and 5.6 for 2.5 hours. Then, the pH was controlled down to 5.4 and left to react overnight (approximately 18-24 hours). The resulting chitosan catechol solution was pH controlled to approximately 5.5 and subsequently dialyzed at approximately pH 5.8 for 3 days and deionized water for 3 days. The dialysate was changed periodically throughout the dialysis procedure.

After dialysis, the solution was allowed to evaporate excess water gained during dialysis by hanging the solution in the dialysis tubing in a fume hood overnight. The solution was left until it returned to its pre-dialysis weight.

Approach 5

CS-Catechol, Batch 35

Chitosan (1.681 g+10.6% w/w moisture) was dissolved in deionized water (143.5 g) with 1.0 M HCl solution (11 mL). The pH of the chitosan chloride solution was then brought up to approximately 5.5 with 1.0 M NaOH solution. A 1:1 v/v solution (150 mL) of deionized water and ethanol was prepared and N-(3-dimethylaminopropyl)-N'-ethylcarbodiimide hydrochloride (EDC; 8.76 mmol), 3,4-dihydroxyhydrocinnamic (HCA; 2.39 mmol), and N-acetyl-L-cysteine (NAC; 2.36 mmol) were dissolved in the water/alcohol solution (-reactant solution-). Next, the reactant solution was added to the chitosan chloride solution. The pH of the reaction mixture was controlled between 5.2 and 5.3 during the addition of the reactant solution. After 2 hours, the pH of the reaction mixture was brought up to approximately 5.4. The solution was then left to react overnight (approximately 18-24 hours). After reacting overnight, the pH of the solution was controlled up to approximately 5.5. The solution was dialyzed against 5 L of deionized water for 6 days. The dialysate was changed periodically (at least every 24-48 hours) throughout the dialysis procedure.

Approach 6

CS-Catechol, Batch 38

Chitosan (1.678 g+10.6% w/w moisture) was dissolved in deionized water (143.3 g) with 1.0 M HCl solution (8 g). The pH of the chitosan chloride solution was then brought up to approximately 5.5 with 1.0 M NaOH solution. A 1:1 v/v solution (150 mL) of deionized water and ethanol was prepared and N-(3-dimethylaminopropyl)-N'-ethylcarbodiimide hydrochloride (EDC; 2.95 mmol), 3,4-dihydroxyhydrocinnamic (HCA; 1.475 mmol were dissolved in the water/alcohol solution (-reactant solution-). Next, the reactant solution was added to the chitosan chloride solution. The pH of the reaction mixture was controlled at close to pH 5.5 during the addition of the reactant solution. After 2 hours, the pH of the reaction mixture was adjusted up to 5.51. The solution was then left to react in a covered beaker a room temperature for 20 hours. After 20 hours, the pH of the solution was 5.54. The solution was divided into 3 lots of close to 100 g solutions in dialysis tubing and dialyzed against 5 L of deionized water for 5 days with pH at 5.8-5.9 on the first 3 days and pH 6.2 on the fourth day. The dialysate was changed regularly (every 24 hours) throughout the dialysis procedure.

Example 2

Freeze Phase Separated Hydrophilic Polymer Dressings

Hydrophilic polymer aqueous solutions were prepared inside 500 ml, 1000 ml or 2000 ml Nalgene LDPE bottles or polypropylene beakers by addition of components including but not limited to pre-prepared solution, hydrophilic polymer, water, acid, and additional components. FIG. 12B lists 85 of the formulation types that were investigated.

The main problems experienced when formulating for the transuretheral prostatectomy application with dressings in direct contact with urine were: 1) rapid (generally <30 mins) urine promoted dissolution of chitosan; 2) interference from blood in achieving rapid adherence with the pure catechol modified chitosans; 3) susceptibility to dressing cracking and tearing when making changes to formulations to address problems with dissolution and adherence. The final hydrophilic polymer solution % w/w was between 0.1% to 4% by weight polymer. Capped bottles and their contents were mixed continuously at room temperature over 12-24 hours to achieve full solution homogeneity using IKA KS260 orbital shaker or a Wheaton bench top bottle roller. Beaker solutions were mixed on a magnetic stirrer plate with magnetic stirrer bead at room temperature for 12 to 24 hours to achieve solution homogeneity. Parafilm was used to close the beaker from the external environment during mixing. The solutions prepared for freeze phase separation were substantially homogeneous and clear when suspension conditions were not present. The catechol chitosan solutions demonstrated some haze and milky appearance indicating presence of some dispersed fine catechol chitosan globular particles.

Chitosan solutions were prepared as freeze phase separated dressings with final solution % weight of hydrophilic polymer in the range 0.25% to 4% w/w aqueous solution. Freeze phase separation was performed in Teflon coated aluminum mold wells with horizontal flat bases. The solutions were poured into the wells to a height from the mold base of preferably not more than about 10 mm, more preferably 2.5 mm and most preferably 5.0 mm. The solutions initially at a temperature in the molds before freezing between 15° C. and 30° C. were then frozen by application of cooling through the base of the molds. Although other cooling temperatures may be applied to achieve suitable freeze phase separated structure, preferably the applied cooling temperature of the shelf was −40° C., more preferably the cooling temperature was −55° C. and most preferably the cooling temperature was −45° C. After the solution achieved freezing phase separation and the temperature of the frozen solution equilibrated at the freezing temperature, the system was allowed to further freeze phase separate and equilibrate for at least an additional hour before drying. In a modified freezing and mold filling method to accommodate layers of different freeze phase separated solutions, a first layer was added to the mold to a preferred depth and frozen, a second layer was then added and frozen, a multi-layered freeze phase separated dressing could be prepared in this manner. Care was needed to ensure there was no frost between an (n-1)th frozen and nth poured solution and differences in layer frozen structure could result in cracking. Layering of separate frozen layers adhering together and not cracking is a significant problem. The discovery of the successful method of layering and adhering of single layer previously dried hydrophilic polymer matrices to a single co-adhered compressed multilayered composite sheet during this investigation was an unexpected and significant finding.

A 24 square foot shelf Virtis Benchmark 2000 pilot scale freeze dryer was used for sublimation freeze drying of the freeze phase separated frozen solution plaques. In the primary freeze drying (removal of ice not hydrogen bonded to the hydrophilic polymers), the equilibrated frozen plaques in their molds were subjected to reduction in pressure ≤300 mTorr within the freeze dryer, the freeze dryer condenser was set to ≤−65° C. and the freeze dryer shelves were heated to promote sublimation of the ice from the freeze separated plaques without increasing plaque temperature above −15° C. After removal of substantially all the non-bonded ice, the shelf temperature was raised to near 25° C. for removal of the hydrogen bonded ice and reduction of moisture content in the dried dressing matrix to not more than 4% residual water in the dried dressing matrix. Final dried matrices conformed to the original shape of the filled mold with close to 5% shrinkage in length and width and density between 0.005 g/cm3 and 0.04 g/cm3. They contained void space of more than 95% and they were interconnected porous structure with fine polymer lamella (submicron to 5 micron thickness) and pore spacing between adjacent lamella of 100 microns to 300 microns.

After freeze phase separation and drying, the dried matrices were compressed from their original thicknesses (10 mm to 2.5 mm) to a final thickness preferably near 50 microns. If two uncompressed dressings were compressed one on top of the other then they would be permanently bonded together at the conclusion of the compression process. Calibrated uniform thickness thin shims may be used in the compression to achieve a desired thickness of compressed dressing substantially the same thickness as the shim. There are a number of ways to achieve this compression with a desired compression set near 50 microns. The preferred compression method used in the investigation was compression of the whole dried uncompressed dressing (dimensions typically close to 100 mm long×100 mm wide×2.5 mm high or 50 mm diameter×2.5 mm high) with uniaxial compression rate at ≤0.5 mm/min to ≤100 microns thickness between aligned platens. The platens (Diamond sprayed or Teflon coated Mic 6 Aluminum 300 mm×300 mm×90 mm) were machined to flat planar faces (≤5 microns in 300 mm) with none or some controlled texture machined into their surface. The temperature of platens during compression was maintained preferably near 80° cover 3-5 minutes of uniaxial compression. Compression was achieved by screw loading at the four corners of the platens at up to four tonnes loading at each corner. Compression was held for at least 2 minutes before release of load. The novel compressed hydrophilic polymer matrices were measured for compression thickness and weight. Final densities were between 0.25 and 0.9 g/cm$^3$. After compression, the dressings were further processed. This additional processing included die cutting into 2.5 cm diameter test pieces and in some cases thermal annealing heat treatment (heated in a convection oven at 60° C.-150° C. for 5-30 minutes). At the conclusion of processing the dressings were placed in foil pouches with zip lock or thermal sealing. Packaged dressings intended for animal and biocompatibility testing were gamma-irradiated at 25 kGy.

Example 3

In Vitro and Ex-Vivo Testing of Chitosan Endoluminal Hemostatic Dressing Prototypes In Vitro Beaker Test The dissolution behavior of the CEHD was investigated under conditions similar to those that would be experienced during TURP in vivo use. Dissolution was monitored for periods up to 7 days to establish that the CEHD dissolution met targeted resistance to early dissolution (in the first 24 hours) with subsequent later dissolution so that no residual CEHD would be present after 168 hours (7 days).

Sectioned pieces (25 mm×25 mm×3 mm) of porcine bladder tissue with mucosal surface facing outwards were fixed with cyanoacrylate cement to the bottom of a 200-milliliter polystyrene beaker. One drop of solution of 1:250 v/v blood in standard saline was onto the top surface of the ex-vivo sectioned bladder tissue. A CEHD dressing piece (1.3 cm×1.9 cm) was applied with 9.7 kPa (73 mmHg) pressure to the wetted tissue surface by application of a 500-gram standard weight (Troemner, Thorofare NJ 08086) onto a 2.54 cm diameter probe for 5 minutes. Sufficient synthetic urine (50 ml) at room temperature was added to the beaker to submerse the CEHD pieces. The beaker was covered with Parafilm, incubated (Fisher Scientific Model 146E, CAT. 97-990E) at 37° C., and placed on a shaker (IKA AS260.1, KS 260) at 120 rpm. The synthetic urine solution was changed every 24 hours and dissolution behavior was documented by amount of dressing visually present at regular intervals until complete dissolution, or up until 168 hours. In some tests, CEHD test piece adhesion to tissue was evaluated by a horizontal scraping movement of tweezers to measure resistance to sheer force. The CEHD tissue adhesion testing was performed during the in-vitro dissolution testing on a pass or fail basis, and noted as low, moderate, or high.

The results of in vitro dissolution and adhesion to porcine bladder mucosa are shown in FIG. 15. The in vitro dissolution and adhesion to porcine bladder mucosa results were used together with results of folding and device deployment testing to select three preferred dressing types for biocompatibility and in vivo testing. These dressing types included catechol modified chitosan preparations and preparations of both catechol and thiol chitosan modification. The preferred pre-in-vivo dressing types were labelled types A, B and C. Dressing Lots 71 and 81 representing type A dressings; Lots 78 and 83 representing B type dressings and Lots 75, 80 and 84 representing type C dressings.

In-Vitro Simulated Venous Wound Sealing (SVWS) Testing

A laboratory simulated venous wound sealing (SVWS) device was built to test the sealing ability of the CEHD adhered by one drop of dilute blood, 1:250 v/v blood in standard saline, with 9.7 kPa load for 5 minutes over a 1.5 mm diameter "injury" aperture in the center of a standard PVC plate whose surface had previously been shown to mimic dermis with respect to mucoadhesive chitosan binding to dermis. Silastic Laboratory Tubing, Size—0.250 in I.D.×0.375 in O.D., Dow Corning Corporation (Midland, MI 48686) connected an open reservoir of citrated bovine whole blood to the aperture with a stopper valve immediately before the aperture. The vertical height of the blood level in the reservoir relative above the aperture was adjustable from 0.0 to 50 cm. After a CEHD test dressing was attached centrally over the aperture in the standard PVC surface the stopper valve was opened and dressings were observed for 15 minutes and assessed (pass/fail) on their ability to maintain sealing (absence of blood leakage through or under the attached dressing). The pressure head was noted in each test. This test provided rapid simulated bleeding control testing of prototype CEHD's under venous bleeding pressure.

Simulated bleeding rate (g/min) was determined by weight difference between a pre-weighed absorbent sheet and the same absorbent sheet placed over the "injury" collecting flowing blood for 15 seconds and multiplying by 4.

A 20 cm to 42 cm head height difference at 23° C. is equivalent to 14.7 mmHg to 30.9 mmHg pressure (typical of venous pressure in prostatic bleeding). Bleed rates for the 20 cm and 42 cm height differences were determined as 4.7 and 8.0 g/min respectively.

Results of in-vitro simulated venous wound sealing (SVWS) testing are provided in Table 1 of 25 kGy gamma irradiated dressings Lots B and C (with shelf life in foil packaging at 25° C. temperature storage for 0 and 6 months).

TABLE 1

| IN-VITRO SIMULATED VENOUS WOUND SEALING (SVWS) TEST RESULTS. | | | | | | | |
|---|---|---|---|---|---|---|---|
| Shelf-life (months) | Dressing type | Height (cm) | Test 1 | Test 2 | Test 3 | Test 4 | Test 5 |
| 0 | C | 21 | Pass | Pass | Pass | Pass | Pass |
| 0 | B | 21 | Pass | Pass | Pass | Pass | Pass |
| 6 | C | 21 | Pass | Pass | Pass | | |
| 6 | B | 21 | Pass | Pass | Pass | | |
| 6 | C | 42 | Pass | Pass | Pass | Pass | Pass |
| 6 | B | 42 | Fail | Fail | Fail | Fail | Fail |

Figure 10:
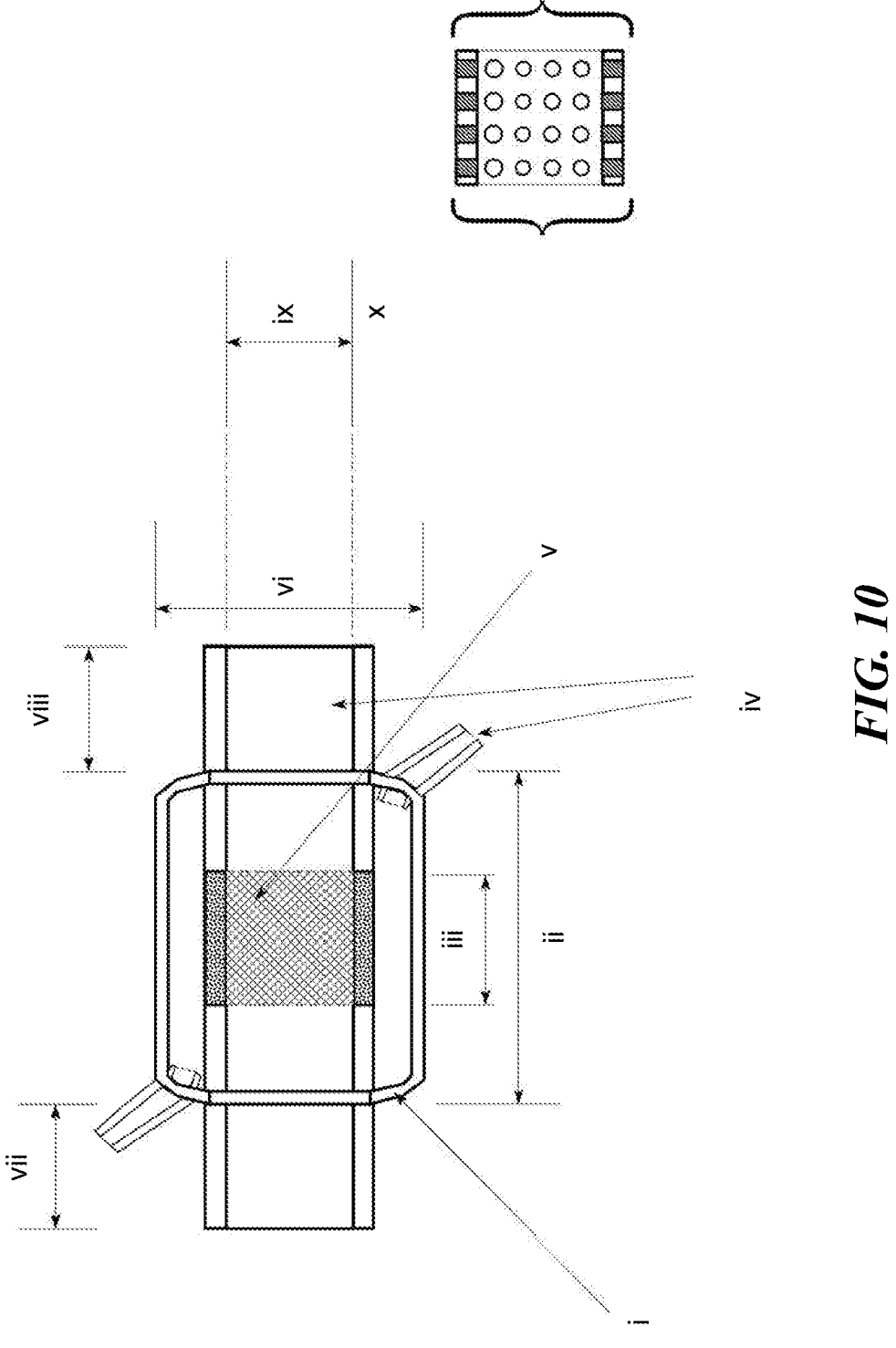
FIG. 10 depicts a glass flow cell 4 cm long and 1.5 cm internal diameter capable of supporting a 6 cm long 1.5 cm diameter stretched tube of porcine small intestine submucosa by wrapping over the ends of the cell and applying pressure ties.
Figure 11:
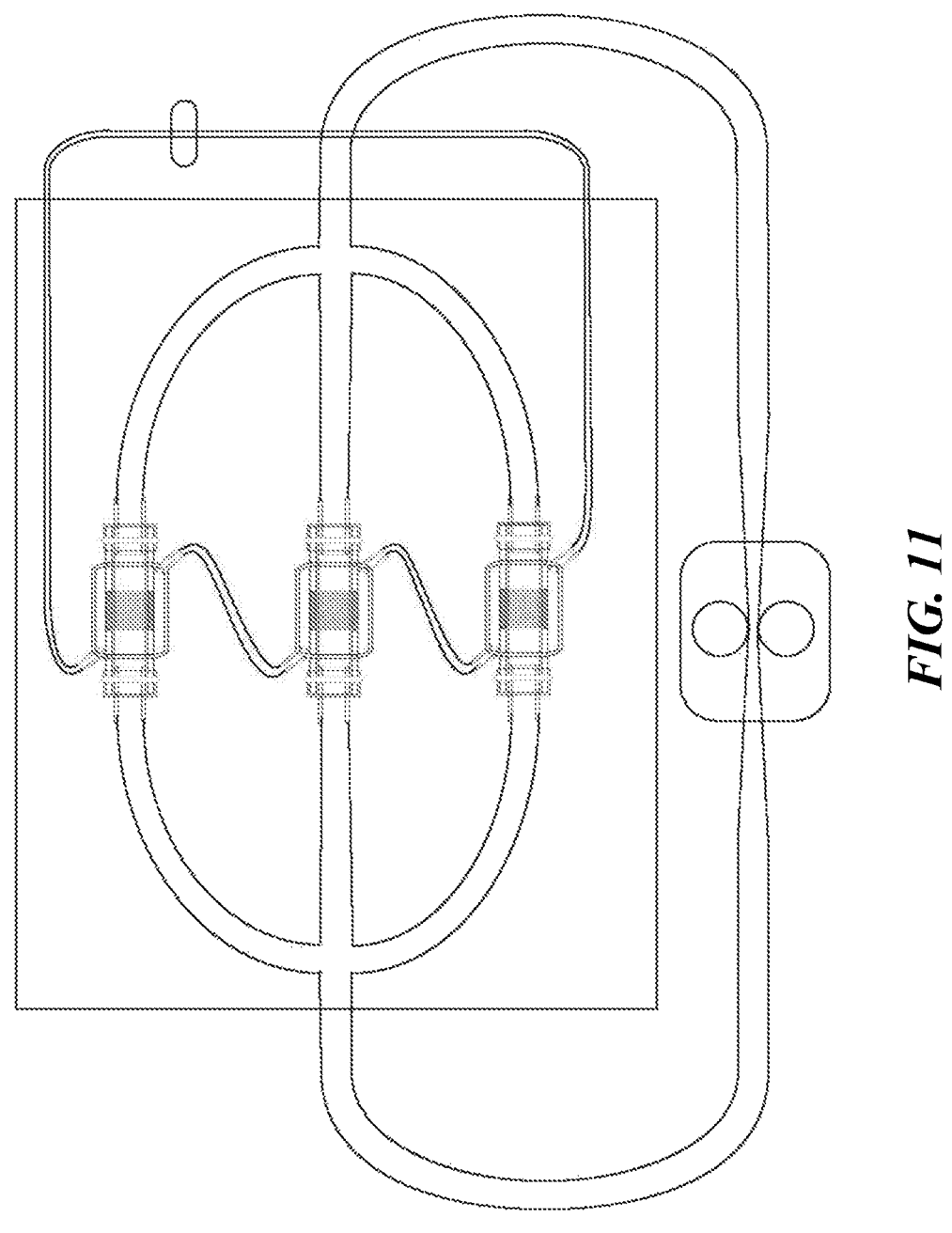
FIG. 11 depicts a typical flow cell design (with 3 cells attached in parallel) for testing adherence and dissolution resistance under urine flow at 37° C. of novel dressings adhered to cell supported ex vivo tissue surfaces.
Figure 14:
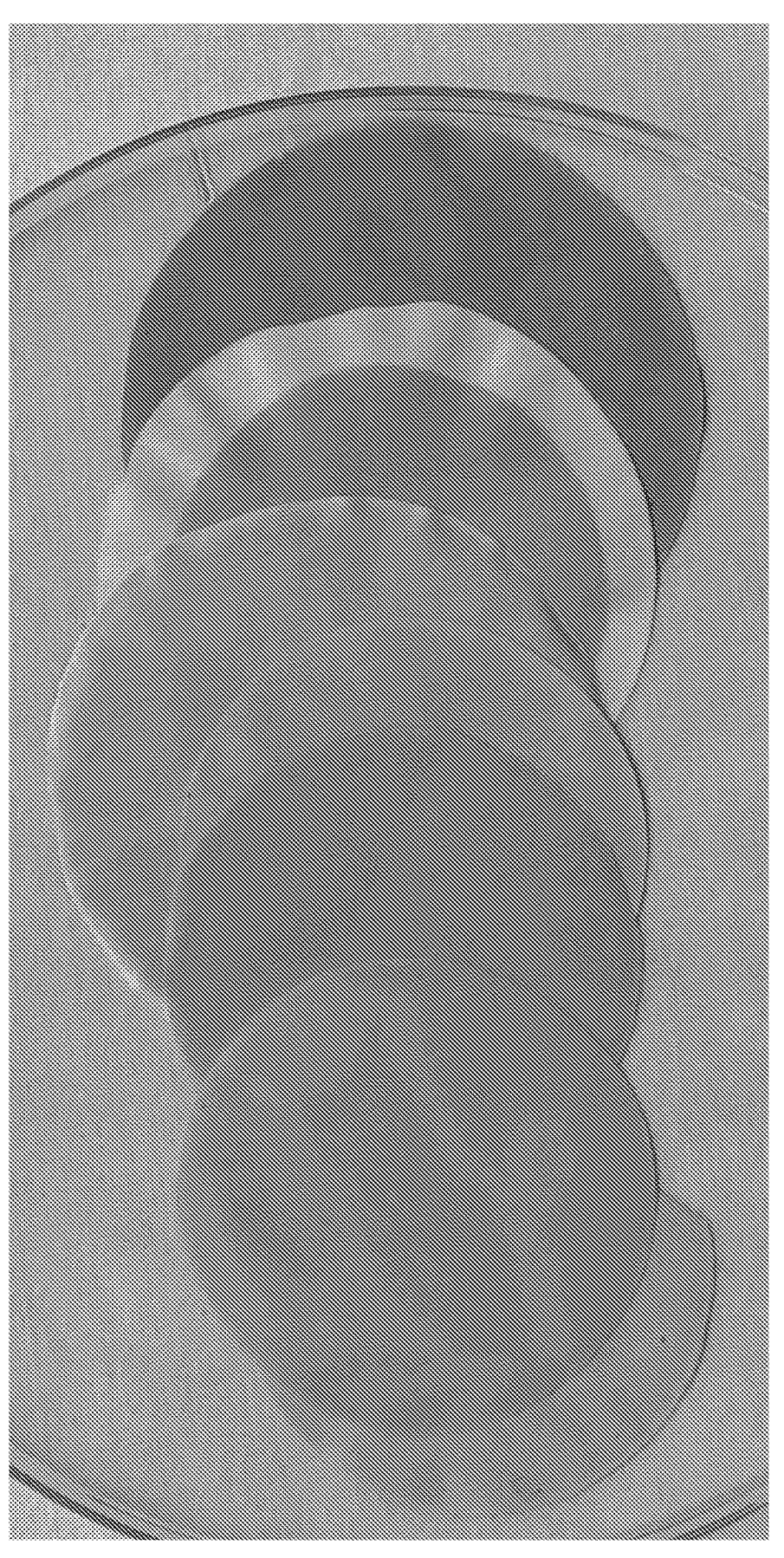
FIG. 14 depicts round-shaped catechol modified chitosan dressing that are (pre-cut) 2.5 inches by 2 inches in diameter and compressed to near 50 microns. The coloration of these catechol modified chitosan dressing, starting from left to right, ranges from light pinkish brown (first dressing), 2 dressings of darker pinkish brown, 2 tan brown colored dressings (no pink), 1 brown dressing and lastly 1 darker brown dressing. Catechol chitosan dressings 5 and 6 are formed from 2.5 inch and 2 inch molds and they are backed with unmodified chitosan dressings both from 2.5 inch molds and the unmodified chitosan can be seen clearly as the white halo (no brown or pink color) in dressing 6. The catechol chitosan and unmodified chitosan dressings were adhered together during compression to a final shared density >0.4 g/cm$^3$. The pink coloration is associated with unoxidized catechol while the brown color is associated with the oxidized catechol (o-quinone). The lighter browns and lighter pinks are associated with lower degree of substitution of the chitosan with catechol (nearer to 10%) while the darker colorations (pinkish brown and brown) are associated with higher degree of substitution of the chitosan with catechol (nearer to 20%).

Ex-Vivo Flow Testing of 10 mm×10 mm Dressing Adhered Over 3 mm Diameter Perforation in SIS Test dressings that performed well in vitro (dressing types B and C, N=10 each)—see FIGS. 12A, 12B and 15) were adhered under balloon pressure near 7 psi for about 3 minutes to porcine small intestine submucosa (SIS) centrally over a 3 mm diameter hole in the SIS supported in an Adams and Chittenden custom manufactured glass test cell (see FIG. 10). The test cell containing the dressing adhered to the SIS sealing the defect was connected to the flow system depicted in FIG. 11. A Fisher Scientific FH100M multichannel peristaltic pump with 13-310-911 flow cassettes was used to provide a controlled rate of flow near 20 ml/min. Synthetic urine near 34° C. to 37° C. and fully filling the volume of the cell was flowed through the cell at close to 20 ml per minute for 6 to 20 hours. The purpose of the testing was to demonstrate ability of the dressings to remain adhered to mucosa under flowing urine without tearing or loss of particles or larger pieces from the dressing.

In the case of dressing Type C (dressing Lots 75 and 80), one test was performed for 20 hours. At the conclusion of the testing, an external pressure of 1:250 v/v blood in standard saline near 20 mmHg was applied through the jacketed circuit of the glass test cell to test the adherence of the test dressing to the tissue. The application of pressure was applied 4 times and the dressing successfully remained adhered over the 3 mm diameter hole to the internal SIS surface resisting the external application of fluid pressure on all 4 pressure applications. This 20 hour tested dressing was also examined for loss of mass (by gravimetric comparison of dry weight before and after testing). The gravimetric testing of type C dressing after 20 hours showed that material loss of catechol modified chitosan (most likely by dissolution) was ≤15% by dry weight of the original dressing. All other tests for the type C dressings were performed for 6 hours without application of the external pressure stress. In the case of the type C dressings, there was no significant visible dissolution of dressing or any loss of material from the dressings. All dressings remained adhered to the SIS at the end of testing. The adhesion (to SIS mucosa) and cohesion of the dressings were rated as moderate.

In the case of dressing Lot Type B (dressing Lots 78 and 83) one test was performed for 24 hours. This 24 hour tested dressing was examined for loss of mass (by gravimetric comparison of dry weight before and after testing). The gravimetric testing of type B dressing after 24 hours showed that material loss of catechol modified chitosan (most likely by dissolution) was significant at 39.4% by dry weight of the original dressing. All other tests for the type B dressings were performed for 6 hours. In the case of the type B dressings, there were visible indications of significant dissolution of dressing (gelling) and loss of material (visible pieces being released from dressing) from the dressings. The adhesion (to SIS mucosa) and cohesion of the dressings were rated as moderate to low.

Example 4

Foldability and Deployment Testing of Dressing

All dressing Lots (N ≥3) were tested for foldability because this is an important characteristic for ability to attach, furl and deploy the dressing formed from the material of the invention against prostatic and bladder neck injury sites. Fold testing involved folding the horizontally planar final compressed circular dressing through 180° edge over edge, first in an anticlockwise direction, holding the edges together and compressing firmly in the middle of the dressing to create a single linear fold axis (or crease) in the dressing. The folded dressing is then opened and the edge to edge fold is reproduced in the new fold axis but with the folding in the opposite clockwise direction. Foldability success is rated as no tears or cracks being visible along the fold axis and no significant loss in tensile properties of the dressing (determined by gentle pulling across the fold of the dressing). Results of the foldability testing are provided in column 4 of FIG. 15.

Deployment testing (N=5) was performed with preferred chitosan backed dressing types A, B and C using a 250-milliliter volumetric flask filled with normal saline as a model of a urine filled bladder neck. A fully assembled device with CEHD dressing, sheath covering and balloon catheter (distal and proximal balloons) was submerged in the normal saline below the neck of the volumetric flask. The CEHD application was initiated by inflating the distal balloon to break the protective waterproof sheath at its distal end, followed by manual complete and intact removal of the torn sheath by pulling on its dry free end outside the flask, swift positioning of the distal balloon at the bladder neck followed quickly by smooth and rapid inflation of the proximal balloon to open and adhere the dressing against the flask neck. All dressing types (A, B and C) were delivered successfully with good adhesion to the glass vessel neck.

Example 5

Biocompatibility of Dressing Types

ISO 10993-1 biocompatibility testing of finished, packaged, sterile (terminal gamma irradiation at 25 kGy) devices was conducted according to testing requirements for external communicating devices with indirect blood path contact for limited contact. The tested included cytotoxicity, dermal irritation and acute systemic toxicity (in triplicate for each test).

Dressing types A and C passed all the biocompatibility testing while dressing type B failed the acute systemic toxicity testing. It is suspected that gamma irradiation produced a cytotoxic thiol residue in the type B dressing.

Example 6

Acute In Vivo Bladder Neck and Swine Splenic Capsular Stripping Models of Hemostasis Acute in vivo testing was performed in six domestic female Yorkshire swine, body weight 40-50 Kg (Oak Hill Genetics, CA) and the delivery device was assembled with the three CEHD prototypes (Dressing A: n=6; Dressing B: n=9; Dressing C: n=10). The experiment was designed as a blinded randomized study of efficacy of individual prototypes vs controls in acute swine bladder neck and splenic parenchyma bleeding injury models.

TABLE 2

| | | STUDY RESULTS ACUTE IN VIVO | | |
|---|---|---|---|---|
| Conditions | Dressing A | Dressing B | Dressing C* | Control |
| Adherence score in vivo (0-4)‡ | 1.75 ± 0.29 | 1.58 ± 0.91 | 1.7 ± 0.97 | |
| Initial bleeding rate at 5 min (ml/min) in bladder neck injury | 0.035 ± .007 | 0.032 ± .027 | 0.039 ± .031 | |
| Bleeding rate after applied CEHD at 2 hrs in bladder neck injury (ml/min) | 0.0045 ± .0029 | 0.0042 ± .0034 | 0.0034 ± .0011 | |
| Hemostasis at 30 sec in splenic injury mode (ratio) | 1/12 | 3/12 | 5/12 | 0/12† |
| Hemostasis at 3 min in splenic injury mode (ratio) | 6/12 | 7/12 | 4/12 | 6/12† |

*Dressing C was selected to advance to a seven day survival study.
‡0, 1, 2, 3 and 4 = no (material does not adhere), low (adheres but is easily dislodged), moderate (can be removed by probing at edge), moderate to strong (resists removal by probing edge), and strong (probe cannot dislodge edge) adherence respectively.
†Surgical gauze was used as negative control for splenic injury model.

Examples 7-11

Examples 7-11 are drawn to CGHD chitosan dressings. The following materials were used in the CGHD development:

Chitosan A: Primex ChitoClear 65010, TM 4375, MW=250-300 kDa, Brookfield viscosity in 1.0% w/w chitosan solution in 1.0% acetic acid at 25° C. and spindle LV1=390 cPs, DDA=80% (by colloidal titration).

Chitosan B: Primex ChitoClear 43000, TM 4167, MW=110-150 kDa, Brookfield viscosity in 1.0% w/w chitosan solution in 1.0% acetic acid at 25° C. and spindle LV1=9 cPs, DDA=95% (by colloidal titration).

Glacial acetic acid: Fisher Scientific, Catalog No. A38-212.

Hydrochloric acid: 1.0 M aqueous solution Sigma Aldrich, Catalog No. H9892.

L-Lactic acid: JT Baker, Catalog No. 0196-01.

Glycolic acid: JT Baker, Catalog No. M821-05.

Sodium hydroxide: 5.0 M NaOH aqueous solution Sigma Aldrich, Catalog No. S8263-150 ml.

Potassium hydroxide: 0.1 M KOH in methanol (BDH).

Ethanol: 2000 Proof Sigma Aldrich, Catalog No. 459844-1L.

Microfiber chitin: ~10 micron diameter of aspect ratio ~100/1 of 100% acetylated. Weifang Centrifugal spun chitosan nanofiber Lot G01 of basis weight 12 g/m²

Tricol Medical Grade non-woven microfiber.

De-ionized water: Ricca ACS Reagent Grade deionized water, Catalog No. 9152-5.

Acetic anhydride: ACS reagent grade obtained from Sigman Aldrich, Catalog No. 320102-1L.

3,4-dihydroxyhydrocinnamic acid (Mw=182.17 g/mo): 98% Sigma Aldrich, Catalog No. 102601.

1-ethyl-3-(-3-dimethylamino-propyl)-carbodiimide: (alternatively N-(3-dimethylaminopropyl)-N'-ethylcarbodiimide hydrochloride with common acronym EDC) Sigma Aldrich, Cat. #E7750.

Sodium Chloride: Sigma Aldrich, Catalog No. 793566-500g.

Synthetic gastric solution: Pepsin—Sigma Aldrich P7000-25G, NaCl—Sigma Aldrich 793566-500G, H2O ACS Reagent grade, NaOH—Sigma Aldrich, Catalog No. S8263-150 ml.

Tissue: fresh swine bladder mucosa, fresh swine stomach mucosa from Animal Biotech Industries Inc.

Citrated bovine whole blood: Lampire Biological Laboratory Bovine CPD, Catalog No. 7720010.

Cynaoacrylate: Permabond 910 Tissue Adhesive, Catalog No. 72590.

Dialysis Tubing: 3,500 Da MWCO Snakeskin Dialysis Tubing (Fisher Scientific), Cat. #PI88244.

Pectin: MP Biomedicals LLC, Catalog No. 102587.

Glycerol: Sigma Aldrich, Catalog No. G-8773.

Polyethylene glycol: Spectrum, Catalog No. P0108.

Polyethylene oxide: Mw 400,000 da, Sigma Aldrich Catalog No. 372773-500G.

Poloxamer 407: Spectrum, Catalog No. P1166.

Guar: Sigma Aldrich, Catalog No. G4129.

Cellulose (microcrystalline powder): Sigma Aldrich, Catalog No. 435236.

Polyacrylic acid: Mv 1,250,000 Sigma Aldrich, Catalog No. 306215-100G.

HemCon Patch® Pro, highly effective commercial chitosan hemostatic dressings, were used as positive control dressing in acute hemostatic studies.

Standard surgical gauze was used as a negative control in acute hemostatic studies.

Example 7

Preparation of Catechol Chitosan and Characterization

Approach 1.

Chitosan A (9.0 g) was dissolved in deionized water (148 g) and HCl (28 ml, 1.0 M HCl). A 1:1 (150 ml) solution of water:ethanol was prepared. 3,4-dihydroxyhydrocinnamic acid (25.9 mmol) and N-(3-dimethylaminopropyl)-N'-ethylcarbodiimide hydrochloride (51.8 mmol) were dissolved in the water/alcohol solution. The water/alcohol solution was added to the chitosan solution. The solutions were vigorously mixed. The reaction mixture was controlled to pH 5.4 using dropwise addition of 0.1 M HCl and 0.1 NaOH solution and left to react with overhead stirring for at least 12 hours. Following this, the chitosan solution (~300 ml) was dialyzed against 5 liters of water acidified with 1 drop of 1.0 M HCl solution for six days and against non-acidified water for at least 3 hours. Dialysate was changed at ~24 hour intervals throughout the duration of the dialysis with at least 5 changes of water.

Approach 2

Chitosan A (1.5 g) was dissolved in water (140 g) and HCl (5 ml, 1.0M HCl). A 1:1 solution (145 ml) of water: ethanol was prepared. 3,4-dihydroxyhydrocinnamic acid (10.5 mmol) and N-(3-dimethylaminopropyl)-N'-ethylcarbodiimide hydrochloride (13.0 mmol) were dissolved in the water/alcohol solution. The water/alcohol solution was slowly added to the chitosan solution and the reaction mixture was stirred with an overhead mechanical stirrer at low stirrer speed. The reaction mixture was controlled to pH 5.5 using dropwise addition of 0.1 M NaOH and 0.1 M NaOH solution and left to react for ~12 hours under stirring. After the reaction process, the solution was dialyzed as described in approach 1.

Approach 3

Chitosan A (9.0 g) was dissolved in water (126 g) acidified with HCl (30 ml, 1.0M). A 1:1 solution (150 ml) of water: ethanol was prepared with N-(3-dimethylaminopropyl)-N'-ethylcarbodiimide hydrochloride (31.3 mmol) dissolved in the water/alcohol solution. Following this, 3,4-dihydroxyhydrocinnamic acid (15.7 mmol) was dissolved in 15 ml of water and this solution was added slowly to the chitosan solution under moderate overhead mechanically stirring. The water/alcohol solution containing the N-(3-dimethylaminopropyl)-N'-ethylcarbodiimide hydrochloride was slowly added to the chitosan solution and the reaction mixture was stirred with an overhead mechanical stirrer at low stirrer speed. The reaction mixture was controlled to pH 5.5 using dropwise addition of 0.1 M KOH (in methanol solution) and 0.1 M HCl solution and left to react for ~12 hours under stirring. After the reaction process, the solution was dialyzed as described in approach 1.

Approach 4

Chitosan A (9.0 g) was dissolved in water (126 g) acidified with HCl (30 ml, 1.0M). The solution was then adjusted to near pH 5.1 using 0.1 M HCl and 0.1 M NaOH aqueous solution. A 1:1 solution (150 ml) of water: ethanol was prepared with N-(3-dimethylaminopropyl)-N'-ethylcarbodiimide hydrochloride (31.3 mmol) dissolved in the water/alcohol solution. Following this, 3,4-dihydroxyhydrocinnamic acid (15.7 mmol) was dissolved in 15 ml of water and this solution was added slowly to the chitosan solution under moderate overhead mechanically stirring. The water/alcohol solution containing the N-(3-dimethylaminopropyl)-N'-ethylcarbodiimide hydrochloride was slowly added to the chitosan solution and the reaction mixture was stirred with an overhead mechanical stirrer at low stirrer speed. The reaction mixture was controlled to pH 5.0 using dropwise addition of 0.1 M KOH (in methanol solution) and 0.1 M HCl solution and left to react for ~12 hours under stirring. After the reaction process, the solution was dialyzed as described in approach 1.

Degree of Substitution of Catechol Chitosan

Quartz UV test cells, 1 cm path length, ×2 (HACH Co., cat #48228-00) were used in acquiring UV/vis spectra. The UV/Vis spectrophotometer was a Varian Cary Bio 100.

Standard solutions of 3,4-dihydroxyhydrocinnamic acid were prepared in water and absorbance at 280 nm was plotted against concentration. The extinction coefficient E in the Beer Lambert relationship shown below for absorbance in dilute solution $$A = \varepsilon \cdot c \cdot l$$

A is absorbance (dimensionless) and l is the path length (Absorbance <0.5) was determined as 2,540±50 liter/(mol·cm). This value was used to determine degree of substitution in the modified chitosan in dilute aqueous solution of known mass of modified chitosan, known volume of solution and measured peak absorbance at 280 nm.

The chitosan catechol solution is diluted so that its absorbance at 280 nm is less than 0.5 (usually about 1:50 or 1:100). The absorbance, the weight of the solution used in the dilution, and the percent solids (CS-catechol) were used to find the fractional degree of substitution ($f_{DS}$) of the HCA with respect to free amines on the chitosan backbone according to the equations:—

$$f_{DS} = \frac{n_{HCA}}{f_{DDA} \cdot n_{total\ Chitosan\ mers}}$$

$$f_{DS} = \frac{A \cdot V \cdot \{(f_{DDa} \cdot 161) + (1 - f_{DDA} \cdot 203)\}}{\varepsilon \cdot l \cdot \left\{m_{cc} - \left(\frac{A \cdot V}{\varepsilon \cdot l} \cdot 165.17\right)\right\} \cdot f_{DDA}}$$

where A is UV/vis absorbance at 280 nm of the modified chitosan; V is the volume (liters) of the modified chitosan solution taken to dry to constant dry mass; $m_{cc}$ is the measured dry mass (g) of the catechol modified chitosan; $f_{DDA}$ is the fractional degree of deacetylation of the chitosan.

Results

The chitosan-catechol syntheses yielded 50-300 mL of chitosan catechol solution that ranged from milky to clear, light pink to brown, and with viscosity ranging from thin liquid consistency (e.g., water near 1 cps viscosity) to thick liquid consistency (e.g., honey: viscosity >100,000 cps). The synthetic results (see Table 1) were dependent on the initial concentration of chitosan, avoidance of precipitation of chitosan in the pH adjustment step from near pH 2 to pH 5, maintenance of pH near 5.0 to 5.5 during reaction, and thorough removal of low molecular weight components in the dialysis washing step.

TABLE 3

SUMMARY OF
CHARACTERIZATION RESULTS

| Cs-Cat Approach | Percent Solids (w/w)¶ | Percent Substitution |
|---|---|---|
| 1 | 0.72 ± 0.1 | 17.2 ± 2 |
| 2 | 0.42 ± 0.1 | 132* |
| 3 concentrated† | 0.63 ± 0.1 | 29.0 ± 3 |
| 4 concentrated† | 1.80 ± 0.1 | 26.4 ± 3 |

¶Percentage dry solid in the solution was determined gravimetrically
*Synthesis in approach 2 resulted in excessive Uv/vis absorbance in determination of degree of substitution
†Catechol chitosan was concentrated by heat assisted drying removal of water from the solution suspended within its dialysis membrane.

Example 8

Freeze Phase Separated Hydrophilic Polymer Dressings

Hydrophilic polymer aqueous solutions were prepared inside 500 ml, 1000 ml or 2000 ml Nalgene LDPE bottles or polypropylene beakers by addition of components including, but not limited to, pre-prepared solution, hydrophilic polymer, water, acid, and additional components. FIGS. 17A-17C list formulation approaches, hydrophilic polymers, and % w/w of solution hydrophilic polymer components. Some of the formulations in FIGS. 17A-17C do not contain chitosan. Formulation strategies are listed in FIGS. 17A-17C as A, B, C, D, E, F, and G. Strategy A was primarily as a control of materials such as chitosan which were expected not to resist dissolution in the stomach as tested by in vitro simulated gastrointestinal fluid. Reacetylation (Strategy B) was one of the proposed strategies to reduce rate of dissolution/degradation until in vitro simulated gastrointestinal fluid testing in the presence of pepsin demonstrated faster rate of degradation and dissolution of chitosan with lower degree of deacetylation. Strategy C was investigation of compositions of known polysaccharides (guar, pectin and starch) without chitosan which resist in vitro simulated gastrointestinal fluid digestion. Strategy D was strategy C with chitosan and possibly other hydrophilic polymers. Strategy E was use of catechol modified chitosan as the only hydrophilic polymer. Strategy F was use of catechol modified chitosan with other hydrophilic polymers. Strategy G was use of a centrifugal spun chitosan fiber.

The main problems experienced when formulating for the gastrointestinal hemostatic dressing application were: (1) unexpected and rapid (<10 mins) pepsin promoted degradation of chitin and chitosan in synthetic gastric fluid, wherein pepsin promoted a rate of chitosan degradation at increasing rates corresponding with lower degrees of deacetylation; (2) unexpected interference from blood in achieving adherence with the pure catechol modified chitosans; (3) susceptibility in dressing cracking and tearing when making changes to formulations to address other problems.

The final hydrophilic polymer solution % w/w was between 0.1% to 4% polymer. Capped bottles and their contents were mixed continuously at room temperature over 12 to 24 hours to achieve full solution homogeneity using IKA KS260 orbital shaker or a Wheaton bench top bottle roller. Beaker solutions were mixed on a magnetic stirrer plate with magnetic stirrer bead at room temperature for 12 to 24 hours to achieve solution homogeneity. Parafilm was used to close the beaker from the external environment during mixing. The solutions prepared for freeze phase separation were substantially homogeneous and clear when suspension conditions were not present (exceptions with A06, B02, B04 and C05). The catechol chitosan solutions demonstrated some haze and milky appearance indicating presence of some dispersed fine catechol chitosan globular particles.

Except in the case of Strategy G, chitosan solutions were prepared as freeze phase separated dressings with final solution % weight of hydrophilic polymer in the range 0.25% to 4% w/w aqueous solution. Freeze phase separation was performed in Teflon coated aluminum mold wells with horizontal flat bases. The solutions were poured into the wells to a height from the mold base of preferably not more than about 10 mm, more preferably 2.5 mm and most preferably 5.0 mm. The solutions initially at a temperature in the molds before freezing between 15° C. and 30° C. were then frozen by application of cooling through the base of the molds. Although other cooling temperatures may be applied to achieve suitable freeze phase separated structure, preferably the applied cooling temperature of the shelf was −40° C., more preferably the cooling temperature was −55° C. and most preferably the cooling temperature was −45° C. After the solution achieved freezing phase separation and the temperature of the frozen solution equilibrated at the freezing temperature, the system was allowed to further freeze phase separate and equilibrate for at least an additional hour before drying. In a modified freezing and mold filling method to accommodate layers of different freeze phase separated solutions, a first layer was added to the mold to a preferred depth and frozen, a second layer was then added and frozen, a multi-layered freeze phase separated dressing could be prepared in this manner. Care was needed to ensure there was no frost between an (n-1)th frozen and nth poured solution and differences in layer frozen structure could result in cracking. The discovery of the successful method of layering and adhering of single layer previously freeze dried hydrophilic polymer matrices to a single co-adhered compressed multilayered composite sheet during this investigation was an unexpected and significant finding. It is also possible to combine separately prepared freeze dried compositions using compression.

A 24 square foot shelf Virtis Benchmark 2000 pilot scale freeze dryer was used for sublimation freeze drying of the freeze phase separated frozen solution plaques. In the primary freeze drying (removal of ice not hydrogen bonded to the hydrophilic polymers), the equilibrated frozen plaques in their molds were subjected to reduction in pressure ≤300 mTorr within the freeze dryer, the freeze dryer condenser was set to ≤−65° C. and the freeze dryer shelves were heated to promote sublimation of the ice from the freeze separated plaques without increasing plaque temperature above −15° C. After removal of substantially all the non-bonded ice, the shelf temperature was raised to near 25° C. for removal of the hydrogen bonded ice and reduction of moisture content in the dried dressing to not more than about 4% residual water in the dried dressing. Final dried matrices conformed to the original shape of the filled mold with close to 5% shrinkage in length and width and density between 0.005 g/cm³ and 0.04 g/cm³. They contained void space of more than 95% and they were interconnected porous structure (e.g., 20-300 micron) with fine polymer lamella (e.g., submicron to 5 micron thickness) and pore spacing between adjacent lamella of, for example, 20 microns to 300 microns.

After freeze phase separation and drying, the dried matrices were compressed from their original thicknesses (10 mm to 2.5 mm) to a final thickness preferably near 50 microns. If two uncompressed dressings were compressed one on top of the other then they would be permanently bonded together at the conclusion of the compression process. Calibrated uniform thickness thin shims may be used in the compression to achieve a desired thickness of compressed dressing substantially the same thickness as the shim. There are a number of ways to achieve this compression with a desired compression set near 50 microns. The preferred compression method used in the investigation was compression of the whole dried uncompressed dressing (dimensions typically close to 100 mm long×100 mm wide×2.5 mm high or 50 mm diameter×2.5 mm high) with uniaxial compression rate at ≤10 mm/min, or about ≤0.5 mm/min, to ≤100 microns thickness between aligned platens. While lower compression rates lead to better mechanical properties of the final dressings, dressings prepared with initial compression rates near, for example, about 10 mm/min are acceptable. The platens (Teflon coated Mic 6 Aluminum 300 mm×300 mm×90 mm) were machined to flat planar faces (≤5 microns in 300 mm). The temperature of platens during compression was maintained preferably near 80° C. over 3 to 5 minutes of uniaxial compression. Compression was achieved by screw loading at the four corners of the platens at up to four tonnes (tonnes meaning 1000 kilograms) loading at each corner. Compression was held for at least 2 minutes before release of load. The novel compressed hydrophilic polymer matrices were measured for compression thickness and weight. Final densities were between 0.35 and 0.55 g/cm³. After compression, the dressings were further processed. This additional processing included die cutting into 2.5 cm diameter test pieces and in some cases thermal annealing heat treatment (heated in a convection oven at 60° C. to 150° C. for 5-30 minutes). At the conclusion of processing the dressings were placed in foil pouches with thermal sealing. Packaged dressings intended for animal and biocompatibility testing were gamma-irradiated at 25 kGy.

Example 9

In Vitro Testing of Gastrointestinal Hemostatic Dressing Prototypes

Synthetic Gastric fluid preparation: Pepsin (1.6 g), NaCl (1 g), water (500 ml) was added to a Nalgene LDPE 1000 ml bottle and mixed. The acidity was adjusted to be between pH 3 to 4 using Millipore pH 0-14 universal indicator strips and dropwise addition of 3.0 M HCl. Dropwise addition of 1.0 M NaOH was used to raise the pH if required.

1. Test Tube Method

For rapid screening of test article resistance to dissolution/fragmentation in synthetic gastric fluid, a 0.5 cm×0.5 cm piece of test article sheet was added to the base of a labeled 15 ml Falcon tube and 5 ml of gastric fluid was added to the tube before capping and placing upright in an incubator at 37° C. with gentle shaking. The tube was monitored until demonstrable dissolution/fragmentation of the sample was observed and the time to dissolution/fragmentation was recorded. The results of test tube testing are provided in FIGS. 16A-16C.

2. Beaker Method

For materials showing resistance in the test tube test, a modified test method was developed whereby a 38 mm×38 mm piece of fresh stomach mucosa was adhered inside a polystyrene beaker (250 ml, Fisher Catalog No. 08-732-124) at its base using a thin layer of cyanoacrylate adhesive applied using a cotton swab. The mucosa surface prior to gluing was dabbed dry using Texwipe tissue. The adhesive was allowed to dry over 2-5 minutes. After becoming fully adhered to the beaker, the top exposed tissue surface was wetted drop-wise (generally 2 drops) with citrated whole bovine blood, and a 20 mm×20 mm piece from a test article sheet was adhered to the blood covered mucosa surface by application of 500 g of load applied orthogonally to the mucosa surface for 1 minute through a 25 mm diameter PVC flat head probe. Synthetic gastric fluid at room (~90 ml) was added to the beaker. Parafilm was used to seal the beaker and the beaker was placed upright on an IKA KS260 orbital shaker in an incubator at 37° C. under mild shaking (130 rpm). The inside of the beaker was monitored at minutes and then hourly until demonstrable separation from mucosa and/or dissolution/fragmentation of the sample was observed and the time to separation/dissolution/fragmentation was recorded.

During test method development, the load applied (up to 5 kg) and time of application for attachment was up to 5 minutes. In comparison to minimally invasive in vivo application the gastrointestinal surgery team advised that an application not be more than 300 g load applied uniformly over a 2.5 cm diameter dressing for not more than 30 seconds. The original conditions of 5 kg and 120 seconds were modified to 500 g for 1 minute. The application of 300 g load for 30 seconds application is now applied. Results of beaker testing are provided in FIGS. 16A-16C.

3. Mechanical Fold Testing

Sample sheets were folded 1800 along length and width axes and the crease line was compressed. Dry test sheets (25 mm×25 mm) were folded and unfolded and observation of resistance to tearing and cracking was recorded. Results of fold testing are provided in FIGS. 16A-16C.

4. Mechanical Tissue Adherence

A uniaxial mechanical tester (Instron Model 5844) with 10 N load cell was used to investigate wet adhesion to mucosa. Adhesion testing was performed using ASTM F2258-03 "Standard Test Method for Strength: Properties of Tissue Adhesives in Tension". Testing was performed with a testing configuration with lower and upper PVC probes uni-axially aligned in the z vertical direction so that the edges of their x-y horizontal, 15.2 mm diameter faces would accurately (±0.2 mm) coincide with each other with uniaxial lowering of the top probe which was supported on the upper, movable Instron crosshead in chuck fixture. The lower PVC probe was supported in a stationary, bottom, chuck fixture. The bottom PVC horizontal surface was used to support a 10 mm×10 mm mucosal tissue sample adhered at least 5 minutes before testing by cyanoacrylate glue to the PVC surface. The top PVC horizontal surface was used to support a 10 mm×10 mm CGHD test piece that was adhered by a 3M double side tape at least 5 minutes before testing. The square tissue piece was wetted with 0.25 ml of the de-citrated bovine whole blood CPD prior to lowering the probe onto the test surface. The probe was lowered at 10 mm/min until a maximum load of 0.98 N was reached. At contact, the test and tissue pieces contacted accurately (±0.2 mm) and were mutually co-planar. The uniaxial probe load at 0.98 N was maintained for 30 seconds after which the probe was removed at 10 mm/min and maximum failure stress was recorded. The results of adherence testing are shown in Table 4.

TABLE 4

| | PROBE ADHERENCE RESULTS | | |
|---|---|---|---|
| | G01-Nanospun CS (6-layer) (kPa) | F11-25% CS-cat, 22-1 conc'd/2% CS AcOH soln (kPa) | PVC Probe (No Dressing) (kPa) |
| 1 | 0.86 | 2.07 | 0.30 |
| 2 | 1.47 | 3.53 | 0.26 |
| 3 | 2.13 | 4.46 | 0.08 |
| 4 | 1.82 | 6.82 | 0.25 |
| 5 | 0.92 | 3.69 | |
| Mean | 1.44 | 4.11 | 0.22 |
| Std. Dev. | 0.55 | 1.74 | 0.10 |

Example 10

In Vivo (Swine Model of Upper Gastrointestinal Bleeding) Screening Study

Animals

A total of 4 crossbred adult domestic swine, body weight from 40 to 50 kilograms, were used in this study.

All experiments were performed in accordance with the 2011 National Research Council, "Guide for the Care and Use of Laboratory Animal" and applicable federal regulations. The protocol for the animal is in accordance with the NIH Guidelines for the Care and Use of Laboratory Animals and was approved by the Institutional Animal Care and Use Committee. All procedures and care of the animals were performed at the approved animal research facility.

Veterinary staff inspected all of the animals to ensure baseline health. Animals were removed from all bedding 72 hours prior to the procedure and not permitted food 24 hours prior to surgery. Animals were allowed to drink water ad libitum. Twenty minutes prior to the procedure, the animals were given 500 mg of intravenous Cefotetan and a 250 ml fluid bolus of Ringer's Lactate. After premedication with glycopyrrolate and a combination of tiletamine HCl and zolazepam HCl (Telazol®, Fort Dodge Laboratories, Fort Dodge, IA), anesthesia was induced by mask using 5% isoflurane. The swine was intubated, placed on a ventilator, and maintained with 2-3% isoflurane with endotracheal intubation. The right femoral artery was surgically isolated and cannulated with a 6 Fr catheter to facilitate continuous blood pressure monitoring and retrieval of blood for laboratory studies. To induce a state of coagulopathy, 5000 units of heparin, was given intravenously (IV). A continuous infusion of heparin of 50 units/kg was used during the procedure to maintain anticoagulation. An activated clotting time (ACT) level was tested after 10 minutes and then every 20 minutes during the procedure with additional heparin (50% of the original dose, 2500 units) given IV as needed to maintain ACT >250 seconds anticoagulation. ECG, blood pressure, and oxygen saturation were monitored during surgery and recovery. Vitals including blood pressure, % isoflurane, 02 flow, respiratory rate, heart rate, SpO2, capillary refill time, blood pressure and mean arterial pressure, and body temperature were recorded every 15 minutes.

At the completion of the experiment, while under anesthesia, the animals were euthanized with IV administration of Euthasol (1 mg/10 lbs). Death was confirmed by flat-wave ECG and absence of heart beat by stethoscope.

Gastric Bleeding Model

The swine were prepared using Chlorhexadine and draped in a sterile fashion. A midline laparotomy was performed to expose the stomach. A 5-cm segment of the gastroepiploic vessels were dissected free from the gastric wall. For each segment, a 1-cm gastrotomy was made adjacent to the free but intact blood vessels. The artery was then pushed through the gastrotomy and positioned so that it is exposed to the gastric lumen. The gastric incision was then closed in a standard manner along with the abdominal wall. An upper endoscopy (GIF Type Q180, Olympus) was performed to identify the gastric wound site in the stomach. The wound site and gastric vessels were then located and incised with an endoscopic biopsy forceps to create a pulsatile bleeding.

The chitosan gastrointestinal hemostatic dressings (CGHD) identified in Table 5, below, were applied with manual application by hand. In brief, an approximate 12 cm incision was made on anterior gastric wall to expose gastric cavity and to apply the CGHD prototype dressing (20 mm×20 mm) on the gastric bleeding site. Before dressing application, bleed rate was determined using dry pre-weighed folded gauze sponges to absorb any blood from the wound over a 15 second period and weighed, multiplied×4 to calculate bleed rate (weight of blood) per minute. The CGHD dressing was placed over the wound with a gauze sponge on top. Manual pressure is applied evenly with light pressure near 200-300 g over the patch for 30 seconds. At 30 seconds the gauze was removed and the area was observed for initial hemostasis and followed for signs of rebleeding for up to 10 minutes. At completion of application, the CGHD dressing was removed and dressing tissue adherence was ranked according to an adherence score in accordance to how the dressing adhered to tissue surface using the Adherence Score System (Table 5).

TABLE 5

ADHERENCE SCORE

| Score | Description |
|---|---|
| 0 | No adherence |
| 1 | Little adherence |
| 2 | Moderate adherence |
| 3 | Moderate to strong adherence |
| 4 | Strong adherence |

Results

| Type of Dressing | Code# | Gastric Vascular Injury | | |
|---|---|---|---|---|
| | | Bleed rate (g/min) | Hemostasis Rate (%) | Adhesion score |
| 4Ch01.Pect | D24 | 8 | 70% | 2 |
| ChCatechol | E1 and E2 | NA | 29% | 2.5 |
| 0.25Cat1.5Ch | F11 | NA | 63% | 2 |
| 0.75Cat0.5Ch | F12 | NA | 50% | 1.5 |
| Nanofiber 12GSM | G01 | 5 | 67% | 1 |
| Patch Pro | H01 | NA | 100% | 3.5 |
| Gauze | H02 | 13 | 33% | 0 |

Three CGHD family prototypes (D24, F11, and G01) demonstrated good hemostatic properties in terms of immediate hemostasis and acceptable adhesion scores in the gastric vascular injury model. Slow wound tissue adherence for pure catechol modified chitosan was addressed by combination of unmodified chitosan with the catechol chitosan. Final heat treatment of these compressed freeze phase separated dressings for 15 minutes to 30 minutes at close to 80° C. resulted in dressings with good immediate tissue adherence and thus promising hemostatic performance in rapidly controlling pulsatile hemorrhagic gastrointestinal bleeding with short (30 seconds) low pressure applications. It is noted that the Patch Pro is not suitable for use in the gastroscope delivery as it cannot be folded as required and is too thick. Also, the Patch Pro is formed of standard chitosan which is degraded in about 15 minutes or less in the upper GI.

Example 11

In Vivo (Swine Model of Upper Gastrointestinal Bleeding) 3 Hour Study

Animals

A total of 4 crossbred adult domestic swine, body weight from 40 to 50 kilograms, were used in this study.

Animal preparation, surgical preparations, animal anesthesia and animal sacrifice were the same as presented in Example 4.

Gastric Bleeding Model

Figure 2:
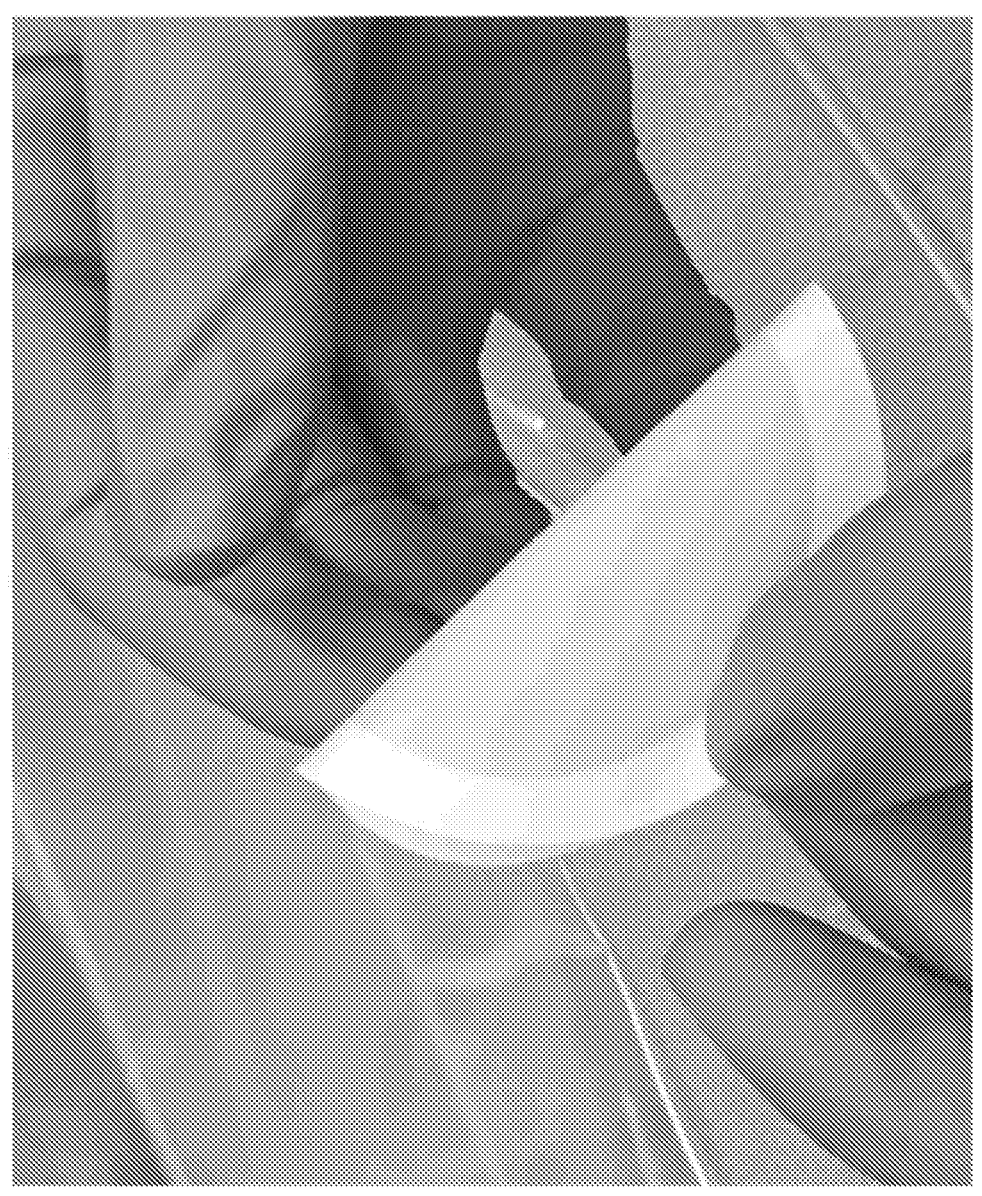
FIG. 2 depicts a digital image of gloved hands holding folded two-sided dressing formed from the material of the invention with darker side being the tissue adhesive catechol modified chitosan side and the lighter side and other edge area being the unmodified chitosan dressing side (the unmodified dressing surface diameter is 2.5 inches while the modified catechol dressing surface diameter is 2 inches).
Figure 3A:
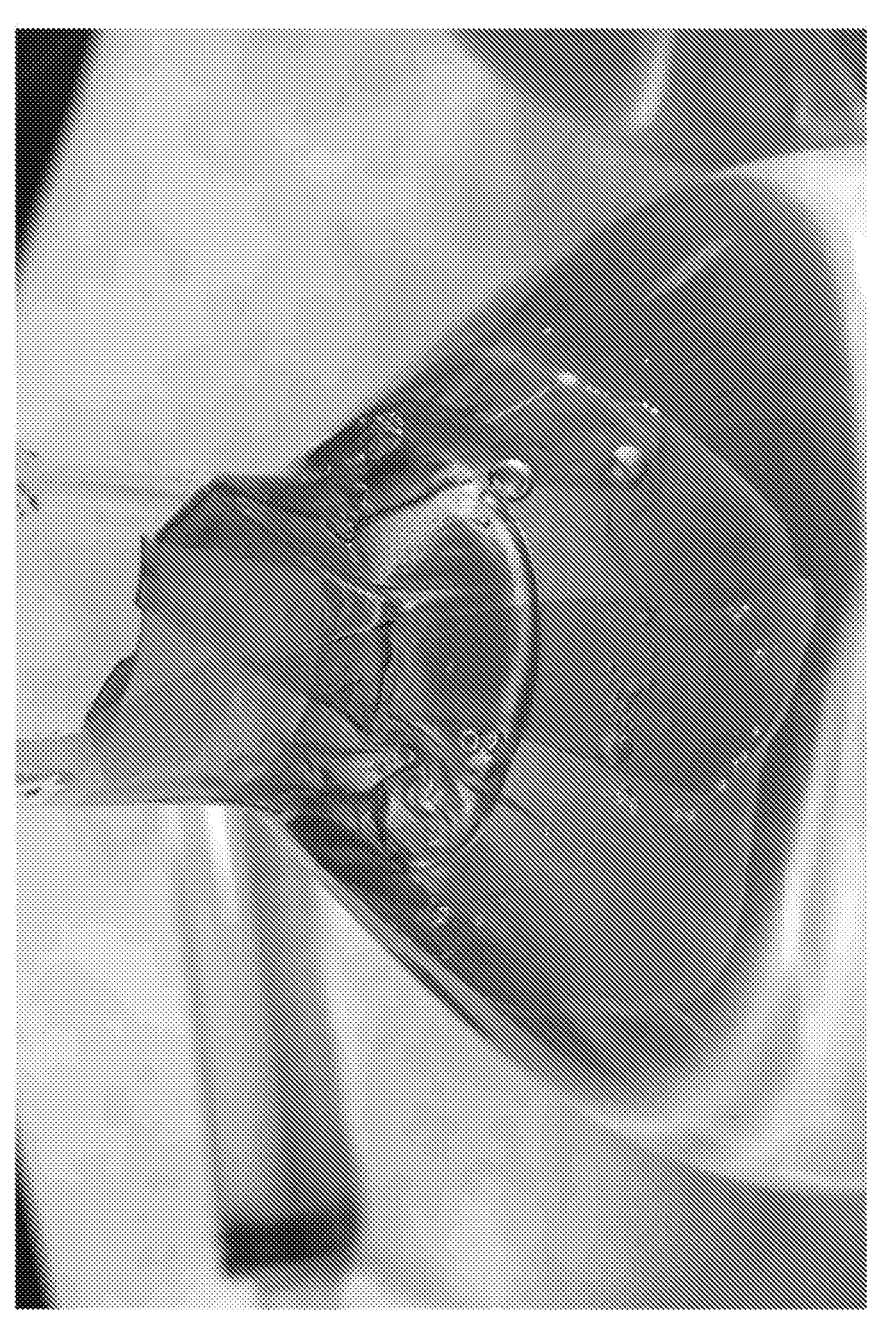
FIG. 3A and FIG. 3B depict digital images of the two-sided catechol modified chitosan dressing formed from the material of the invention adhered to the wall of a 250 ml volumetric cylinder by balloon catheter application for 2 hours submerged in 0.9% w/w physiological aqueous saline solution at 25±3° C. at close to 48 hours after initial attachment. Note that there is no trace of the original unmodified chitosan dressing at 48 hours.
Figure 3B:
Figure 4:
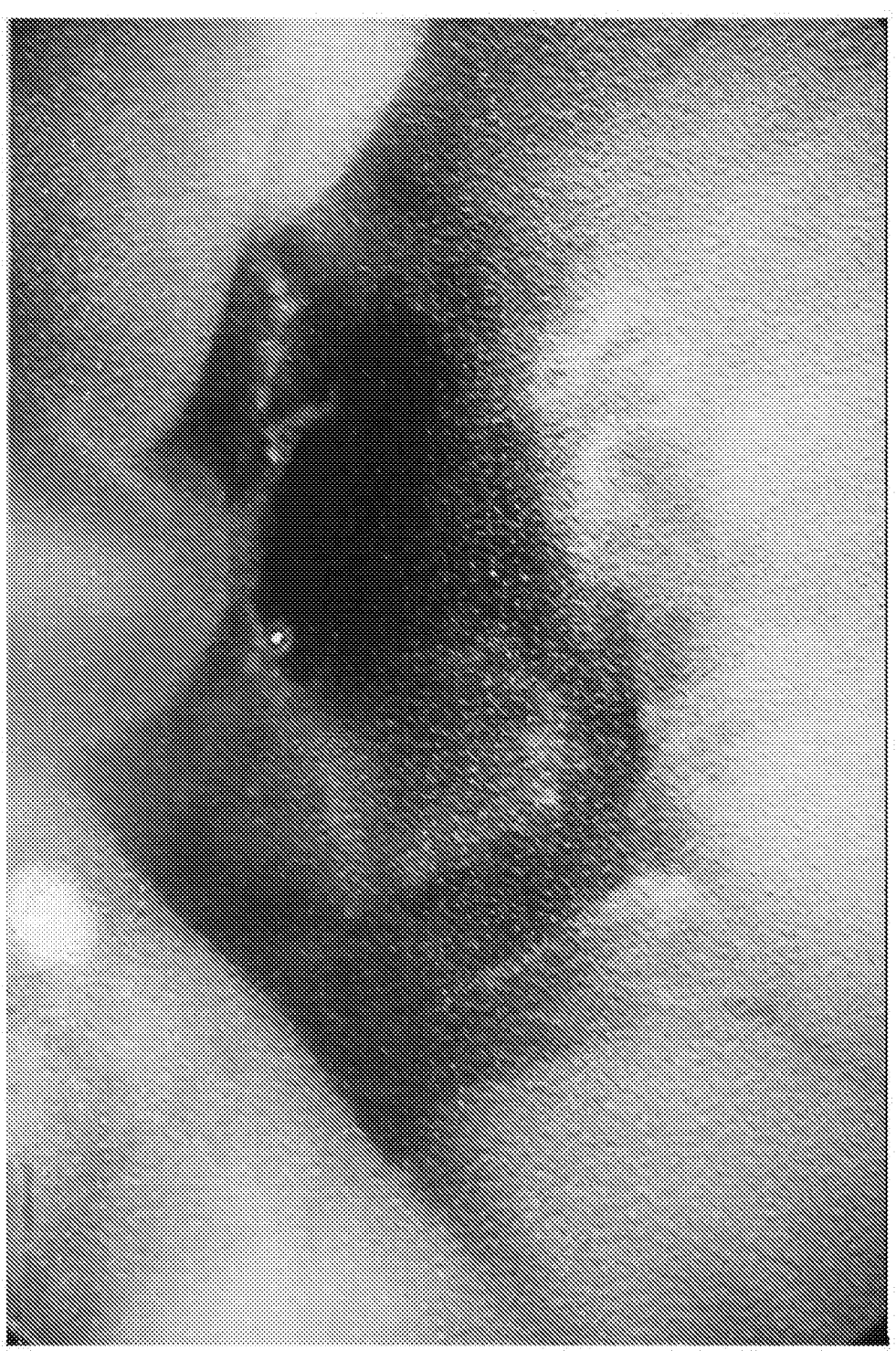
FIG. 4 depicts a digital endoscopic image of the catechol chitosan dressing formed from the material of the invention within 30 minutes attached uniformly to the bladder neck and lumen of urethra of a close to 100 lbs female swine. The bladder is swollen by urine and saline injected to aid in the viewing. The image was taken by trocar delivery of an endoscope through the wall of the swine bladder and with the endoscope viewport directed at the swine bladder neck and entrance to the urethra. The image demonstrates a patent urethra, a wispy rapidly degrading non-modified chitosan backing, and a modified catechol dressing intimately adhered to the bladder neck and lumen of urethra.
Figure 5A:
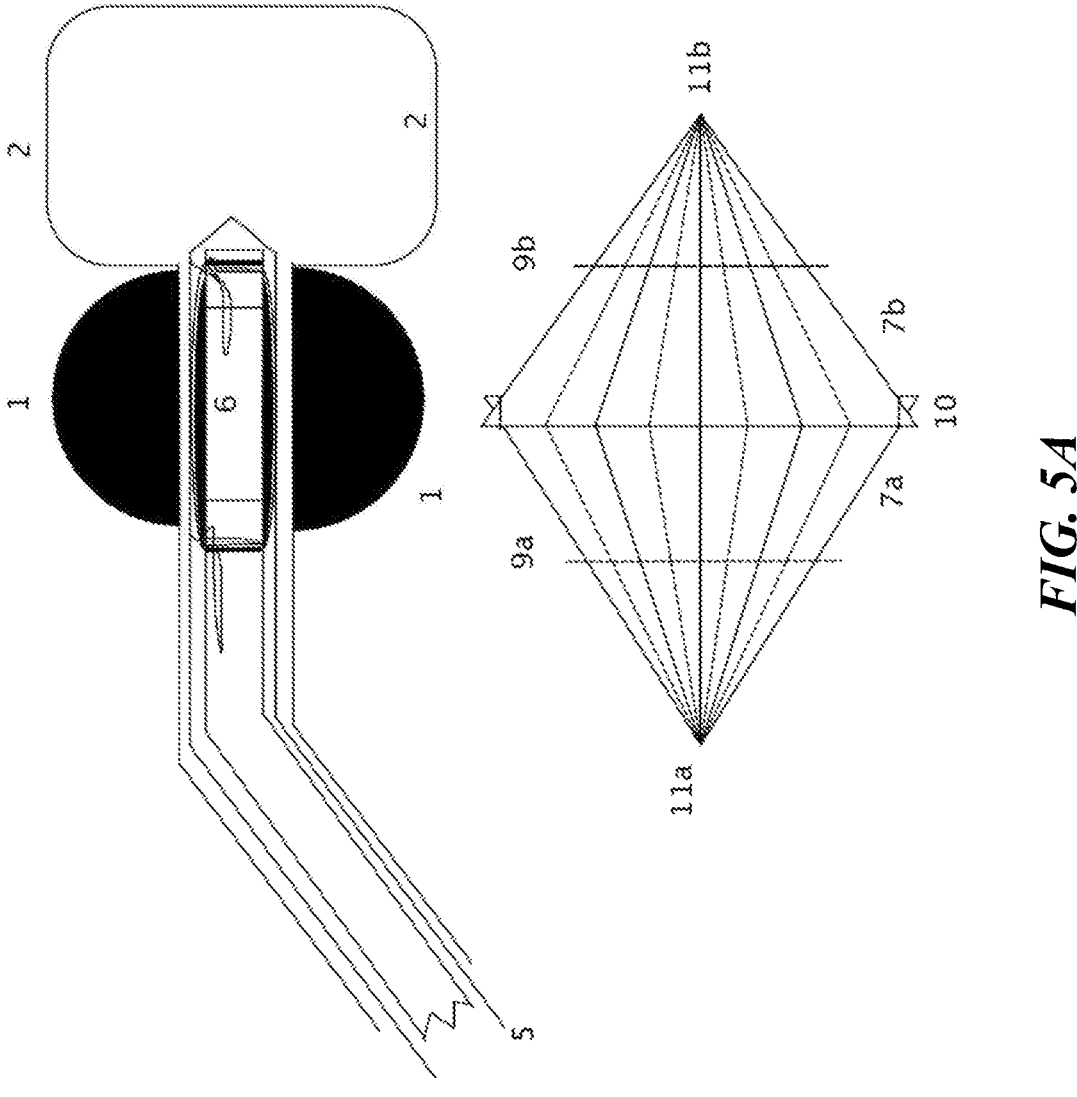

The swine are prepared using Chlorhexadine and draped in a sterile fashion. A midline laparotomy was performed to expose the stomach. Two 5-cm segment of the gastroepiploic vessels were dissected free from the gastric wall. For each segment, a 1-cm gastrotomy was made adjacent to the free but intact blood vessels. The artery was then pushed through the gastrotomy and positioned so that it is exposed to the gastric lumen. The gastric incision was then closed in a standard manner along with the abdominal wall (FIG. 2). An approximate 12 cm incision was made on anterior gastric wall to expose gastric cavity. The wound site and gastric vessels were then located and incised with a forceps to create a pulsatile bleeding. Before applied, the dressing bleed rate was determined using premeasured folded gauze sponges to absorb any blood from the wound over a 15 second period and weighed, multiplied×4 to calculate bleed rate. The CGHD dressing was then placed over the bleed wound with a gauze sponge on top. Manual pressure is applied evenly over the patch for 30 seconds. At 30 seconds the gauze was removed and the area was observed for hemostasis initially and for up to 10 minutes. After 10-minutes observation, if achieved hemostasis, the gastric incision was closed in a layer fashion, i.e., wherein the surgeon sutures incised layers together consecutively. Then the abdominal wall was closed for 3-hours observation. At completion of 3-hours application, an upper endoscopy (GIF Type Q180, Olympus) was performed to identify the wound dressings for a visual examination. Then the incisions of abdomen and stomach were reopened for gross examination of the dressings. The CGHD dressings were removed and gave an adhesion score in accordance to how the dressing adhered to tissue surface using the Adherence Score System (Table 5).

At completion of these procedures, the wound sites were re-prepared by removal of old clots and residual of wound dressing to re-applied second sets of dressing as described above. Each wound site was used to test 2 dressings in this study phase.

Bleed Rate

Metzenbaum scissors were used to make a semi-transected vascular injury at gastric vessels to create a pulsatile bleeding. Bleed rate was measured with a pre-weighed gauze and recorded in g/min. Bleed rate for each injury was determined and recorded prior to dressing application.

Test Pieces were 20 mm×20 mm.

Eight dressings were tested from each type of Nanospun Chitosan (G01) and Chitosan Catechol Blend (F11).

Application of Test Pieces

The 30-second timer was started as the test piece was applied centrally over the injury and with sufficient pressure from fingers to stop bleeding. One piece of 50 mm×50 mm gauze was folded into two and applied over the 20 mm×20 mm test piece. Any subsequent pooled blood was suctioned from the site. After 30 seconds of light digital pressure (near 300 g load), fingers were removed and the test dressing observed for any sign of bleeding. If bleeding was observed, pressure was re-applied for 30 seconds. If hemostasis was achieved upon the release of the pressure, dressing was observed for 10 minutes. If there is no bleeding recurrence, the stomach wall was closed and observed through GI scope for 3 hours. If there was no bleeding recurrence after 3 hours, the dressing test piece was considered successful. If bleeding recurred within 5 minutes, the dressing was removed and a new dressing applied. Up to two reapplications were utilized.

TABLE 6

BELOW SUMMARIZES THE RESULT OF THE STUDY.

| Dressing Code# | # of dressing passed | | | # of dressings tested | % success |
|---|---|---|---|---|---|
| | 1st app | 2nd app | 3rd app | | |
| F11 | 3 | 1 | 2* | 13 | 46 |
| G01 | 0 | 3** | 1* | 12 | 31 |

*1 dressing from each group had extra dressing to stop oozing after 3$^{rd}$ pressure application
**1 dressing was held for extra 30 seconds Nanospun chitosan dressing (GO1) had 4 successful application out of 12 dressings applied. While the 25% catechol/75% 2% chitosan dressing (F11) had 6 successful application out of 13 dressings tested. Two deviations were noted for the dressing applications: one dressing from each group had extra dressing to stop oozing that did not stop on swine #4; and one of nanospun chitosan dressing was held for extra 30 seconds.

On all applications, an endoscope was inserted to evaluate if the dressing was still present and hemostatic. In all cases, all dressings were confirmed as present, hemostatic and visible through the scope. After more than 3 hours of dressing application, the stomach was opened to allow the injury sites and dressings to be examined. All dressings were intact. Clot formation was observed on all wounds. It was noted in all cases of initial dressing success that there was no subsequent bleeding observed from the wounds at the 3 hour timepoint.

The final best dressing prototypes identified through testing in Examples 3, 4, and 5 demonstrated prolonged efficacy once they were adhered under light manual pressure with short duration application hold necessary for delivery through a standard gastroscope delivery port. The best dressings that were developed were amenable in a folded (or furled) configuration to be delivered through a standard diameter 2.8 mm diameter delivery channel from a standard gastroscope.

All CGHD dressings that achieved successful hemostasis (complete cessation of bleeding) in the first 10 minutes of application with no more than 3×30 second hold applications remained fully hemostatic through the 3 hour test period inside the closed porcine stomach. Success was achieved for 31% of G01 prototype applications and for 46% of the F11 prototype applications. The challenging nature of this study made success near 50% (i.e., F11 prototype) relevant to clinical application especially when it is noted that all initial successful mucoadhesive applications resulted in 100% success in the longer term. The mixed chitosan and catechol chitosan dressings provide for substantial resistance to digestive fluid digestion, are able to be folded/furled into the most complex and compact forms, and provide for good adhesive properties in conjunction with mixing with unmodified chitosan.

The invention claimed is:

1. A modified chitosan material, wherein the chitosan has a degree of polymerization of greater than 60 and is modified with a compound comprising a catechol group selected from a group consisting of at least one of a 3,4-dihydroxyhydrocinnamic acid; 3,4-dihydroxycinnamic acid; trans-3,4-dihydroxycinnamic acid; and a 3,4-dihydroxyphenylacetic acid;

wherein at least a portion of the catechol groups is oxidized to o-quinone and cross-linked to form at least one of compound (A)

or (B), wherein 'm' represents o-quinone modified chitosan polymer and 'l' represents chitosan cross-linked with the o-quinone modified chitosan polymer, wherein the modified chitosan has a catechol group degree of substitution of from 7% to 29%; and wherein the material is in a dry solid form that comprises an acid salt content of from about 2% to about 15% (w/w) and that is resistant to dissolution in water, saline solution, blood, gastrointestinal (GI) fluid or urine at about 37° C. for at least about 6 hours and adherent to wet tissue.

2. The modified chitosan material according to claim 1, wherein the material has at least one of:

(i) a thickness that is 500 microns or less;

(ii) a density that is in the range of from about 0.03 g/cm$^3$ to about 0.7 g/cm$^3$;

(iii) is compressed;

(iv) is square shaped, rectangular shaped, circular shaped, or circular petal shaped; and (a) measures for each of the length and width for a square or rectangular shape may range from about 10 mm to about 70 mm; and (b) diameter measures for each of the circular or circular petal shape range from about 10 mm to about 70 mm;

(v) has a moisture content of 15% or less by weight (w/w);

(vi) has an adhesive side and a non-adhesive side and, optionally, wherein the adhesive side is provided on a first layer and the non-adhesive side is provided on a second layer, or wherein the adhesive side adheres to a tissue surface when the material is wet, or wherein the non-adhesive side does not adhere to a delivery device when the material is wet;

(vii) adheres to a gastrointestinal mucosa in 1 minute or less, or adheres to a bladder mucosa in 3 minutes or less, or both;

(viii) forms a quaternary ammonium cation at the chitosan glucosamine C-2 amine at a tissue site;

(ix) has a coloration of: 1) a brown coloration including a dark brown coloration; or 2) a pink to pinkish brown coloration.

3. The modified chitosan material according to claim 1, wherein said material is freeze-dried in the form of a lamella and, optionally, wherein the freeze-dried structure has a thickness of 100 microns or less, or wherein the freeze-dried structure comprises more than one freeze-dried layer.

4. The modified chitosan material according to claim 1, further comprising spun fibers.

5. The modified chitosan material according to claim 1, further comprising a porous surface providing one or more of: (i) an absorbent surface; or (ii) channels to redirect moisture away from a target tissue surface site.

6. The modified chitosan material according to claim 1, wherein the material adherence strength is greater than or equal to about 1 kPa.

7. The modified chitosan material according to claim 1, wherein the material: (i) when folded or furled does not crack or tear; (ii) when, in an open, unfurled, or unfolded condition, has an outward facing surface area that may range from about four to about eight times greater than the outward facing surface area of that same material when it is in a closed, furled, or folded condition; (iii) has a ratio of the outward facing surface area of an open, unfurled, or unfolded condition relative to a closed, furled, or folded condition that may range from about 15:1 to about 2:1; or (iv) when punctured or sewn does not crack or tear.

8. The modified chitosan material according to claim 1, wherein the material is deliverable intact by a balloon device, a wire device, or an endoscopic device and, optionally, wherein the balloon device or the wire device, or the endoscopic device comprises a working channel having a diameter of 7.0 mm or less, and wherein the material is delivered through the working channel, and wherein the material when wet adheres intact to either gastric mucosa in less than 30 seconds with application of a pressure of 50 kPa or less, or to bladder mucosa in less than three minutes.

9. The modified chitosan material of claim 8, wherein the pressure is from about 20 kPa to about 30 kPa, or the material adheres intact to bladder mucosa in less than two minutes, or both.

10. The modified chitosan material according to claim 1, wherein the material: (i) removes hydrophilic and hydrophobic biological fluids that interfere with adhesion; or (ii) stays in place intact and stops moderate to oozing bleeding ranging from about 1 ml/min to about 150 ml/min, and wherein the material readily detaches from a delivery device after adherence to a target tissue site.

11. The modified chitosan material according to claim 1, wherein the material resists dissolution for at least six hours after adhering to an injury site in presence of corrosive enzymes and acid environment of about pH 3, or in presence of urine, or both; or wherein the material seals and protects a target tissue site for at least 12 hours; or wherein the material achieves a controlled, slow dissolution from the attachment site over a period of time not exceeding seven (7) days; or wherein the material is folded and unfolded; or wherein the material is able to be furled and unfurled; or wherein the material does not dissolve fully at pH from about 4.5 to 8 at about 37° C. for at least 12 hours following application.

12. The modified chitosan material according to claim 1, wherein the material does not dissolve fully in water, saline solution, blood, or GI fluid or bladder fluid, or urine at 37° C. for at least 12 hours following an application.

13. The modified chitosan material according to claim 2, wherein the material does not adhere to a delivery device; does not increase or decrease in size by more than about 25% in length and width, or more than about 50% in thickness in the presence of water, saline solution, blood, or GI fluid or bladder fluid, or urine at about 37° C.; comprises an adhesive side that interacts with an injury site, and wherein the chitosan material comprises a non-adhesive side that interacts with one of a delivery device or the adhesive side when the material is in a dry and folded or a dry and furled condition; is sterilized without affecting material characteristics; and is stored under controlled conditions over time without affecting material characteristics.

14. The modified chitosan material according to claim 1 for use in a treatment of an injury by directly adhering the material at an injury site upon wetting, and applying pressure to the material for about 30 seconds and allowing the material to remain at the injury site for at least 24 hours.

15. The modified chitosan material according to claim 14 for use in a treatment of an injury, wherein the material dissolves completely from the injury site without human intervention in seven days or less.

16. The modified chitosan material according to claim 1 for use in combination with transurethral resection of a prostate by directly adhering the material to an injury site.

17. The modified chitosan material according to claim 1, wherein the dry solid form is selected from the group consisting of a powder, a matrix, a membrane, a thin foil, a pleget, a fiber, or a coating.

* * * * *